US005702916A

United States Patent [19]

Molin et al.

[11] Patent Number: 5,702,916
[45] Date of Patent: *Dec. 30, 1997

[54] BIOLOGICAL CONTAINMENT

[75] Inventors: Søren Molin, Holte; Poul Kirketerp Andersson, Frederiksberg; Kenn Axo Gerdes, Virum; Per Klemm, Frederiksberg, all of Denmark

[73] Assignee: GX Biosystems A/S, Copenhagen, Denmark

[*] Notice: The term of this patent shall not extend beyond the expiration date of Pat. No. 5,670,370.

[21] Appl. No.: 449,958

[22] Filed: May 25, 1995

Related U.S. Application Data

[63] Continuation of Ser. No. 205,824, Mar. 4, 1994, abandoned, which is a continuation of Ser. No. 947,910, Sep. 21, 1992, abandoned, which is a continuation of Ser. No. 132,942, filed as PCT/DK87/00031, Mar. 25, 1987, abandoned, which is a continuation-in-part of Ser. No. 29,760, filed as PCT/DK86/00070, Jun. 18, 1986, abandoned, and Ser. No. 610,985, filed as PCT/DK83/00086, Sep. 15, 1983, Pat. No. 4,760,022, said Ser. No. 947,910, is a continuation-in-part of Ser. No. 406,880, Sep. 13, 1989, Pat. No. 5,545,541, which is a continuation of Ser. No. 29,760.

[30] Foreign Application Priority Data

Mar. 26, 1986 [DK] Denmark .................. 1455/86
Dec. 23, 1986 [DK] Denmark .................. 6294/86

[51] Int. Cl.⁶ ............... C12P 21/00; C12N 1/21; C12N 15/63
[52] U.S. Cl. .............. 435/69.1; 935/252.3; 935/320.1
[58] Field of Search ............... 435/69.1, 172.3, 435/245, 252.3, 252.31, 252.33, 252.34, 320.1; 536/23.1, 23.7

[56] References Cited

U.S. PATENT DOCUMENTS

| | | | |
|---|---|---|---|
| 4,436,815 | 3/1984 | Hershbergor et al. | 435/34 |
| 4,634,678 | 1/1987 | Solstrom et al. | 435/320.1 |
| 4,767,708 | 8/1988 | Minkley et al. | 435/194 |

FOREIGN PATENT DOCUMENTS

| | | |
|---|---|---|
| 0109150 | 4/1984 | European Pat. Off. |
| 84/01171 | 3/1984 | WIPO |
| 84/01172 | 3/1984 | WIPO |

OTHER PUBLICATIONS

Klemm, 1985, Fimbriae adhesions of *Escherichia coli*, Rev. Infect. Dis. 7, 321–339.
Molin, Soren; "Containment Scenarios" Manuscript (1990).
Contreras, et al., Conditional–Suicide Containment System for Bacteria which Mineralize Aromatics, Applied & Environ. Microbiol., 57:1504 (1991).
Poulsen et al.; The gef Gene from *E. coli* is Regulated at the Level of Translation; Mol Microbiol, 5, 1639–1648 (1991).
Klemm, et al.; Fimbriae of *Escherichia coli* as carriers of heterologous antigenic sequences, Res. Microbiol., 141, 1013–1017 (1990).
Cuskey, S.M.; Use of the RK2 *kila* Gene for Biological Containment of Microoganisms Released to the Environment; To be submitted to: Applied & Env. Microbiol.; Cont. No. 657; Env. Res. Lab., U.S.E EPA.
"Fox, Contemplating Suicide Genes in the Environment", ASM News, 55:259 (1989).
Poulsen et al., A Family of Genes Encoding a Cell–Killing Function may be Conserved in all Gram–Negative Bacteria; Mol. Microbiol., 1989, 3, 1463–1472 (1989).
Molin, Soren, Untitled Manuscript Relating to Suicide Systems (ref. IX).
Knudsen and Karlstrom, "Development of Efficient Suicide Mechanisms for Biological Containment of Bacteria Applied & Environ. Microbiol.," 57:85–92 (1991).
"Bej. et al., Model Suicide Vector for Containment of Genetically Engineered Microorganisms", Applied & Environ. Microbiol., 54:2472 (1988).
Steffan et al.; Inducible Systems for the Containment of Genetically Improved Gram Negative Bacteria; EERO Workshop, Konigslutter, Germany, Apr. 28 –May 1, 1990.
Hill et al., in Drlica et al. (eds) The Bacterial Chromosome, American Society for Microbiology, Washington D.C., pp. 335–340 (1990).
Mahan et al. in Drlica et al. (eds) The Bacterial Chromosome, American Society for Microbiology, Washington D.C., pp. 341–349 (1990).
Smith, Mechanism and Control of Homologous Recombination in E. coli; Ann. Rev. Genet. 21:179–201 (1987).
Watt, et al., Homology Requirement for Recombination in E. coli; PNAS (USA), 82:4768–72 1985).
Mizuno, et al., A Unique Mechanism Regulatin Gene Experssion; Translational Inhibition by a Complementary RNA Transcript (micRNA); PNAS (USA), 81:1966–70 (1984).
Old and Primrose, Principles of Gene Manipulation, vol. 2, pp. 153–162 (Blackwell Scientific Publication 4th ed., 1989).

(List continued on next page.)

*Primary Examiner*—David Guzo
*Assistant Examiner*—Robert Schwartzman
*Attorney, Agent, or Firm*—Iver P. Cooper

[57] ABSTRACT

A replicon, in which a nucleotide sequence encoding a cell killing function is regulatably expressed when the replicon is harbored in one type of host cell (primary host cell), so that cells harboring the replicon are killed under conditions under which the cell killing function is expressed, and the nucleotide sequence encoding the cell killing function is regulatably or constitutively expressed when the replicon is harbored in another type of host cell (secondary host cell), so that cells harboring the replicon are invariably killed or killed under conditions under which the cell killing function is expressed, may be used in a method of active biological containment of cells under defined environmental conditions. The biological containment principle may be utilized in the industrial production of a biosynthetic product by recombinant DNA techniques, when deliberately releasing a genetically engineered microorganism to the natural environment or in the preparation of a live vaccine. The expression of the cell killing function may be regulated by means of a promoter.

69 Claims, 31 Drawing Sheets

OTHER PUBLICATIONS

Jorgensen, et al.; In vivo Genetic Engineering: Homologous Recombination as a Tool for Plasmid Construction Gene, 96:37–41 (1990).

Agterberg, et al.; Use of Outer Membrane Protein PhoE as Carrier for the Transport of a Foreign antigenic Determinant to the Cell Surface of E. coli K-12; Gene, 59:145–150 (1987).

Wu, et al.; Expression of Immunogenic Epitopes of Hepatitis B Surface Antigen with Hybrid Flagellin Protein by a Vaccine Strain of Salmonella; PNAS (USA), 86:4726–30 (1989).

Izant and Weintraub; Constitutive and Conditional Suppression of Exogenous and Endogenous Genes by Anti-Sense RNA; Science, 229:345–352 (1985).

Travers; Regulation by Anti-Sense RNA; Nature, 311–:416 (1984).

R.H.A. Plasterk et al., *Proc. Natl. Acad. Sci. USA 80*, 1983, pp. 5355–5358; "DNA inversions in the chromosome of *Escherichia coli* and in bacteriopgage Mu: Relationship to other site-specific recombination systems."

G. Mertens et al., *EMBO J. 3*, No. 10, 1984, pp.2415–2421; "Gin-mediated site-specific recombination in bacteriophage Mu DNA: overproduction of the protein and inversion *in vitro*."

J. Zieg and M.I. Simon, *Proc. Natl. Acad. Sci. USA 77*, No. 7, 1980, pp. 4196–4200; "Analysis of the nucleotide sequence of an invertible controlling element."

P. Klemm, *EMBO J. 5*, 1986, pp. 1389–1393; "Two regulatory *fim* genes, *fimB* and *fimE*, control the phase variation of type 1 fimbriae in *Escherichia coli*."

Maniatis et al., *Molecular Cloning: A Laboratory Manual*, Cold Spring Harbor, 1982 (whole textbook) Attached are: pp. 280–281, p.388, p.256; (pages taken are from three different articles.)

Bagdasarian et al., *Gene 16*, 1981, pp. 237–247; "Specific-purpose plasmid cloning vectors. II. Broad host range, high copy number, RSF1010-derived vectors, and a host-vector system for gene cloning in *Pseudononas*."

Lovett and Keggins, *Meth. in Enzymol.* 68, 1979, pp. 342–357; "*Bacillus subtilis* as a Host for Molecular Cloning."

Bech et al., *The EMBO Journal 4*, 1985, pp. 1059–1066; "Sequence of the *relB* transcription unit from *Escherichia coli* and identification of the *relb* gene."

Clark and Maaloe, *J. Mol. Biol. 23*, 1967, pp. 99–112; "DNA Replication and the Division Cycle in *Escherichia coli*."

Clewell and Helinski, *Proc. Natl. Acad. Sci. USA 62*, 1969, pp. 1159–1166; "Supercoiled Circular DNA-Protein Complex in Escherichia coli: Purification and Induced Conversion to an Open Circular DNA Form."

Birnboim et al., *Nucl. Acids Res. 7*, 1979, pp. 1513–1523; "A rapid alkaline extraction procedure for screening recombinant plasmid DNA."

Stougaard and Molin, *Anal. Biochem. 118*, 1981, pp. 191–193; "Vertical Dye-Buoyant Density Gradients for Rapid Analysis and Preparation of Plasmid DNA."

R. Simon, *Biotechnology*, Nov. 1983, pp. 784–791; "A Broad Host Range Mobilization System for In Vivo Genetic Engineering: Transposon Mutagenesis in Gram Negative Bacteria."

G. Skogam, J. Nilsson, P. Gustafsson, *Gene 23*, 1983, pp. 105–115; "The Use of a partition Locus to increase stability of tryptophan-operon-bearing plasmids in *Escherichia coli*."

Yansura and Henner, *Proc. Natl. Acad. Sci. 81*, 1984, pp. 439–443 —(Identical With Ref. No. AL2 Below); "Use of the *Escherichia coli lac* repressor and operator to control gene expression in *Bacillus subtilis*."

Bonner, T.I. et al., *J. Mol. Biol. 81*, 1973, pp. 123–135; "Reduction in the Rate of DNA Reassociation by Sequence Divergence."

Beltz, G.A. et al., *Meth Enzymol. 100*, 1983, pp.266–285; "Isolation of Multigene Families and Determination of Homologies by Filter Hybridization Methods."

Gerdes et al., *J. Bacteriol. 161*, 1985, pp.292–298; "Stable Inheritance of Plasmid R1 Requires Two Different Loci."

Prentki et al., *Gene 17*, 1982, pp. 189–196; "A modified pBR322 vector with improved properties for the cloning, recovery, and sequencing of blunt-ended DNA fragments."

Miki et al., *J. Bacteriol.* 141(1), 1980, pp. 87–99.

Sharp et al., *J. Mol. Biol. 75*, 1973, pp. 235–255; "Electron Microscope Heteroduplex Studies of Sequence Relations among Plasmids of *Escherichia coli*."

Ogura & Hirago, *Proc. Natl. Acad. Sci. USA 80*, 1983, pp. 4784–4788; "Mini-F plasmid genes that couple host cell division to plasmid proliferation."

Yanzura and Henner, *Proc. Natl. Acad. Sci. USA 81*, Jan. 1984, pp. 439–443 — ★★★Identical With Ref. No. AD2 Above★★★.

Klemm et al., *Mol. Gen. Genet. 199*, 1985, pp.410–414; "The *fim* genes responsible for synthesis of type 1 fimbriae in *Escherichia coli*, cloning and genetic organization."

Gerdes et al., *Proc. Natl. Acad. Sci. USA 83*, 1986, pp. 3116–3120; "Unique type of plasmid maintenance function: Postsegregational killing of plasmid-free cells."

Coleman et al., *Nature*, 315, 1985, pp. 601–603; "A novel immune system against bacteriophage infection using complementary RNA (micRNA)."

Abraham et al., 1985, Chemical Abstracts, vol. 103, Abstr. No. 155047o.

Klemm et al., 1985, Chemical Abstracts, vol. 103, Abstr. No. 65870y.

Tacon et al., 1980, Chemical Abstracts, vol. 92, Abstr. No. 177271q.

```
301       .         .         .         .         .         400
    GCCATGAAACTACCACGAAGTTCCCTTCTGTCTGTCTGTTGATATTCACTTATCTCACACGAAAATCGCTGTCGGAGA
    CGGTACTTTGATGGTGCTTCAAGGGAACACAGACACACAACTAGCACAGACTGTGACAACTATAAGTGAATAGACTGTGCTTTTAGCGACACGCTCT
            fMetLysLeuProArgSerSerLeuValTrpCysValLeuIleValCysLeuThrLeuLeuIlePheThrTyrLeuThrArgLysSerLeuCysGluIle
            Hok protein                                                               IV 401       .         .         .         .         .         500
    TTCGTTACAGAGACGGACACAGGCAGGTGGC GCTTTCATGGCTTACGAATCCGGTAAGTAGCAACTAGAGGCGGGCCAGGCCCGGCCCTTTCAGGACT
    AAGCAATGTCTCTGCCTGTGTCCGTCCACGGCCTCCACGGCCGAACCGAATGCTTAGGCCATTCATCGTTGGATCTCCCCCCGGATCTCCCCGGGCCGGGAAAGTCCTGA
           ArgTyrArgAspGlyIleArgGluValAlaAlaPheMetAlaTyrGluSerGlyLysTer 501       .         .         .         .         580
    CATGCTCGGTCTGACTACTGAACCCCCTTTATAAAGGGGCTGCTTGCCCGGTAGCCCCGGTACCCCCCTTTCTCCTTGCTGCTGATGTTGT
    CTACGACCAGACTGATGACTTCCGCGAAATATTTCCCCGACGACTTCGGGAACGGGCCATGCGGACCAAGCGGGAAAGAGGAACGACTACAACA
```

Fig. 3b parB-6K
Met Lys Leu Pro Arg Ser Ser Leu Val Trp Cys Val Leu Ile Val Cys Leu Thr Leu Leu
Met Lys Gln Gln Lys Ala Met Leu Ile Ala Leu Ile Cys Leu Thr Val Ile
Gen3-6K Ile Phe Thr Tyr Leu Thr Arg Lys Ser Leu Cys Glu Ile Arg Tyr Arg Asp Gly His Arg
Val Thr Ala Leu Val Thr Arg Lys Asp Leu Cys Glu Val Arg Ile Arg Thr Asp Gln Thr Glu Val Ala Ala Phe Met Ala Tyr Glu Ser Gly Lys Lys-COOH
Glu Val Ala Val Phe Thr Ala Tyr Glu Pro Glu Glu Glu-COOH

Fig. 7a

```
251                                                                                    320
    TAGTCCACATCAGGATAGCCCTCTTACCGGCTTTGCGCAAGGAGAAGAAGGCCATGAAACTACCACGAAG
     -  - - -  ::  - :::     - :::::::: :::: :::::  -  :  - :: :: - ::
    TGTTTCGCACCGAAGGTGACACTTCTGCTTTGCGTTGACAGGAGAAGCAGGCTATGAAGCAGCAGCAAAA
    (1037)                                                  SD      Met 321                                                                                    390
    TTCCCTTGTCTGTGTGTGTTGATCGTGTGTGTCTCACACTGTTGATATATTCACTTATCTGACACGAAAATCG
     -  - ::: - :: - -  :  - :::   ::  - :: - -  -  - :: -  -  :  - :: - :::
    GATGTTAATCGCCCTGATCGTCATC       TGTTTAACCGTCATAGTGACGGGCACTGGTAACGAGGAAAGAC
                                                              Met 391                                                                                    460
    CTGTGCGAGATTCGTTACAGAGAGACGGACACAGGGAGGTGGCGGGCTTTCATGGCTTACGAATCCGGTAAGT
    ::  - ::::::  -  :  - ::  -  -  :  - ::::::: - ::::  ::::::::  -  -  :::
    CTCTGCGAGGTACGAATCCGAACGGACCAGAACCGACGGAGGTCGCTGTCTTCACAGCTTACGAACCTGAGGAGT 461                                                                                    530
    AGCAACCTAGAGGCGGGGCGGGGAGCCCGCCAGGGCCCGCCCTTTCAGGACTGATGCTGGTCTGACTACTGAAGCGCCTTTA
     -  - -   -  - :::  -  -  -  :: - -  -  - :::  -  -  :: - ::  -  - ::: - :
    AAGAGACCCGGCGGGGGAGAAATCCCTCGCCACCTCTGATGTGGCAGGCATCCTCAACGCACCCGCACTT
    Ter 531                                         580
    TAAAGGGGCTGCTGGTTCGCCGGTAGCCCCCTTTCTCCCTTGCTGATGTTGT
     -  - ::: - :: -  - - :::  -  -   -    ::: ::  - 
    AACCCGCTTCGGGCGGGTTTTGTTTTTATTTTCAACGCGTTTGAAGTTCT (1363)
```

Fig. 7b pPKL8

BIOLOGICAL CONTAINMENT

This application is a continuation of Ser. No. 08/205,824, filed Mar. 4, 1994, now abandoned, which is a continuation of Ser. No. 07/947,910, filed Sep. 21, 1992, now abandoned, which is a continuation of Ser. No. 07/132,942, filed Nov. 6, 1987, now abandoned, (a) which is the national stage of Serial No. PCT/DK87/00031, filed Mar. 25, 1987, now abandoned, (b) which is a continuation-in-part of Ser. No. 07/029,760, filed Feb. 13, 1987, now abandoned, which is the national stage of PCT/DK86/00070, filed Jun. 18, 1986, now abandoned, and (c) which is also a continuation-in-part of Ser. No. 06/610,985, filed May 15, 1984, U.S. Pat. No. 4,760,022, which is the national stage PCT/DK83/00086, filed Sep. 15, 1983, now abandoned. Also, 07/947,910 is a continuation-in-part of 07/406,880, filed Sep. 13, 1989, U.S. Pat. No. 5,545,541, which is a continuation of 07/029,760, supra.

The present invention relates to a method of biologically containing an organism or a replicon under certain conditions, and a replicon used in the method, as well as a cell containing said replicon.

TECHNICAL BACKGROUND

The techniques employing the in vitro recombination of DNA molecules which techniques are popularly termed "genetic engineering" have made it possible to isolate specific genes and express such genes in a variety of host cells, including host cells in which the genes in question are not found or expressed in nature. A recombinant DNA molecule typically consists of a vector which is able to replicate autonomously in the host cells harbouring it or which is integrated into the host cell genome, one or more genes coding for one or more desired biosynthetic products and DNA sequences required for expression of the gene or genes in the host cell. The recombinant DNA techniques have become important for industrial applications such as large-scale fermentation of genetically engineered organisms such as bacteria, yeasts or animal cells, to produce one or more desired biosynthetic products such as peptide hormones, e.g. insulin and growth hormone, or enzymes such as plasminogen activators; another important area of application is the controlled release of genetically engineered microorganisms or viruses into the environment, for instance bacteria or viruses capable of killing larvae of insects which are harmful to certain plants, bacteria degrading certain pollutants, such as oil, or bacteria which reduce the cold sensitivity of certain crops.

From the earliest stage of development of recombinant DNA techniques in the 1970s, the scientific community has been highly aware of the possible biological hazards associated with genetic engineering. As a result, the National Institutes of Health, Bethesda, USA, proposed a set of "Guidelines for Recombinant DNA Research" which set the standard for most other countries. Since 1978, the Guidelines have been revised regularly on the basis of accumulated experimental evidence concerning the possible biological hazards associated with recombinant DNA work.

Despite a tendency to relax the NIH regulations, public opinion remains greatly concerned about the possible biological hazards associated with genetic engineering. Public concern has mainly been directed towards possible effects of experiments involving the controlled release of genetically engineered organisms to the environment. However, in many countries the large-scale production of biosynthetic substances to be used in connection with therapy and the like has also been questioned with respect to its safety, especially with respect to the effect of the accidental release of the recombinant organisms producing such substances from the fermentors to the environment. Therefore, it is not possible to exploit the industrial potential of genetic engineering fully, before the safety aspects have been resolved.

In order to avoid or at least reduce the risks associated with experiments or large-scale applications of genetic engineering, such as the release of recombinant organisms to the environment, measures have been taken to limit the number of such organisms released under ordinary operating conditions as well as in the case of certain types of accident by means of a suitable physical design of laboratories and production facilities.

Such measures are termed "physical containment" by which is meant any design feature of laboratories or production facilities which is intended to confine the recombinant organisms to a specific, predetermined, restricted area. Different levels of physical containment are required for different types of recombinant DNA work according to NIH regulations. Thus, work with potential pathogens requires stricter physical conditions in the laboratory or production facility where the work is carried out.

Physical containment measures are feasible within a laboratory or production facility, while no such measures are possible in the case of applications involving controlled release of genetically engineered microorganisms to the environment.

Alternatively or concomitantly, the continued survival of accidentally released recombinant organisms or the spread of recombinant DNA molecules in the environment may be limited by "biological containment". This term is meant to indicate any feature of the host cell or replicon employed in the production of a specific biosynthetic product or employed for its ability to bring about a desired event, which feature serves to limit the growth potential of the host cell outside a specific, restricted environment where specific conditions prevail (in the following termed "defined environment") and/or any feature of a replicon harboured in the host cell, which feature serves to limit the spread of the replicon (as well as any inserted foreign nucleotide sequence, i.e. a nucleotide sequence which is not naturally related to the replicon in question) to other organisms than those for which it has been intended. Biological containment may also be obtained through a combination of specific features of both host cell and replicon, which features limit the survival of the cell. In the present context, such organisms which are provided with specific genetic information in the form of a replicon carrying this information to exhibit specific phenotypical traits, are termed "primary boat cells".

One conventional way of ensuring the biological containment of a specific organism harbouring a recombinant DNA molecule is to limit its ability to propagate outside a defined environment. Typically, host organisms are used which have been attenuated by introducing a number of independent mutations resulting in well-defined requirements for one or more growth factors which are not usually found in the natural environment (defined as the environment outside the defined environment of for instance a laboratory or production facility [in the following occasionally termed the "outside environment"); the term "natural environment" is intended to include the intestinal tract] and/or a generally decreased competitiveness relative to wild-type organisms of the same species. For instance, E. coli K-12 is an attenuated bacterial strain which is commonly used in experiments and productions involving genetic engineering as this attenuated strain is unable to propagate and establish itself outside the defined conditions of the laboratory or production facility in which it is employed. Furthermore, this E. coli strain is unable to adhere to the epithelial cells of the mammalian intestinal tract which is the normal environment of E. coli which means that colonization of the natural habitat of E. coli by genetically engineered E. coli K-12 is highly unlikely to take place.

It should be noted, however, that even though E. coli K-12 is unable to compete with natural organisms, it will still survive for a period of time in a natural environment.

When the experiment or actual production involves the controlled release of a genetically engineered organism to the natural environment (as defined above), it is not feasible to obtain biological containment by using an attenuated host cell as described above. Obviously, microorganisms which are released to the environment in order to function there have to be able to compete favourably with the wild-type organisms in the same environment either of the same species or other species in order to establish themselves, at least transiently, in a suitable ecological niche.

Another area of biological containment is concerned with limiting the spread of genetic information present on a replicon (optionally including inserted foreign DNA), which replicon may for instance be a bacterial plasmid, from a primary host cell used for experimentation or industrial production to other cells of either the same species but lacking the attenuating mutations of the primary host cells imposed as a part of a biological containment system or to cells of a different species which are able to propagate outside the defined environment required for the growth of the primary host cells, which defined environment is part of a biological containment system.

Genetic information can be transmitted among organisms by several means. In the case of bacteria and bacterial plasmids, these may be transferred by bacterial conjugation, where a physical bridge is formed between two mating bacteria so that the plasmid passes from one bacterium to another via this bridge. Bacteria of different species may exchange plasmids by conjugation, and certain plasmids are in fact transmissible between such distantly related gram-negative bacteria as E. coli and Pseudomonas spp. As the ability of bacteria to conjugate and the ability of plasmids to be transferred are properties which are associated with plasmid-borne DNA sequences, it is required that vectors to be used in industrial production involving genetically engineered bacteria lack the DNA sequences responsible for bacterial conjugation and plasmid transfer. This requirement constitutes the major biological containment measure taken with respect to bacterial plasmids.

However, genetic information, which may for instance be present on a bacterial plasmid, may also be spread by other means which are not counteracted by the removal of said genetic information coding for bacterial conjugation and plasmid transfer.

Primary host cells (attenuated by the proper mutations to ensure long-term survival under defined environmental conditions only) harbouring a recombinant DNA plasmid may occasionally be infected by one or more naturally occurring bacteriophages. Some bacteriophages are known to possess the ability to take up plasmids or other DNA molecules at random and transmit them to secondary host cells (cells not intended for the production of biosynthetic products or other purposes, i.e. typically wild-type strains found in the natural environment) which have not been attenuated and which are therefore capable of propagating outside the defined environment employed for growing the primary host cells.

A similar situation may occur if a bacterium harbouring one of the naturally occurring plasmids coding for bacterial conjugation and capable of being transferred on conjugation, conjugates with a primary host cell already harbouring a recombinant plasmid. Homologous recombination may then take place between the two plasmids resulting in the transfer of the recombinant plasmid to another host cell.

A further way of spreading genetic information to cells which lack the attenuating mutations performed on primary host cells is the passive uptake of free DNA by the cells, the so-called transformation. Many naturally occurring microorganisms are able to take up free DNA. The DNA may then be integrated into the chromosome of the novel, secondary host cell or may replicate autonomously in the host cells which, due to the absence of attenuating mutations, may multiply and establish themselves outside the defined environment of the laboratory or production facility. There is some evidence to suggest that substantial amounts of bacterial plasmid DNA are released in biologically active form from, for instance, E. coli cells during growth in a fermentor. This would indicate that the fermentation medium from which the cells have been harvested presents a major source of plasmid DNA which may potentially be taken up by a secondary host cell by transformation, albeit at a low frequency, if the fermentation medium is released to the environment. The currently employed methods of biological containment do not propose any solution to this problem.

In case of experiments or practical applications involving the controlled release of genetically engineered microorganisms to the natural environment (as defined above), the spread of the replicon (optionally including inserted foreign nucleotide sequence(s)) by conjugation may be limited if the genes or nucleotide sequences responsible for conjugation are not located in the vector, cf. the discussion above. However, this method of biological containment does not suggest any measures against the spread of, for instance, a bacterial plasmid to novel, secondary host cells by transduction, by recombination with transmissible plasmids or by transformation of recombinant DNA released from lysed recombinant organisms.

Although attempts have been made to design strains with increased biological containment properties, most if not all of these suffer from the disadvantage that they considerably affect the growth properties of the cells even under preferential conditions in the laboratory or production facility, and most often growth inhibition rather than cell killing is obtained outside the defined environment.

The outline given above of the problems concerning the containment of recombinant organisms has mainly been concerned with bacteria; it should be emphasized that similar arguments apply to eucaryotic organisms and viruses.

DISCLOSURE OF THE INVENTION

The present invention presents a novel approach to the concept of biological containment by making use of an active containment factor, namely a cell killing function which is expressed if primary host cells harbouring a recombinant DNA molecule are subjected to novel environmental conditions or as a result of a random event, or if a secondary host cell receives the recombinant DNA molecule originally harboured in the primary host cell. In some cases, the secondary host cell is only killed under conditions inducing the expression of the cell killing function.

Thus, the present invention relates to a replicon in which a nucleotide sequence encoding a cell killing function is regulatably expressed when the replicon is harboured in one type of host cell (primary host cell), so that cells harbouring the replicon are killed under conditions under which the cell killing function is expressed, and the nucleotide sequence encoding the cell killing function is regulatably or constitutively expressed when the replicon is harboured in another type of host cell (secondary host cell), so that these cells harbouring the replicon are invariably killed or killed under conditions under which the cell killing function is expressed. In the present context, the term "replicon" denotes a segment of nucleic acid, e.g a bacterial plasmid, a bacterial chromosome, a procaryotic virus, a eucaryotic plasmid, a eucaryotic virus, a eucaryotic chromosome, eucaryotic mitochondria or eucaryotic chloroplasts.

In the present context, the term "cell" is intended to indicate bacteria and eucaryotic organisms such as unicellular organisms, e.g. yeasts or fungi, as well as multicellular organisms such as plants, animals or fungi, and cells derived from the tissues of multicellular eucaryotic organisms such as plants, animals or fungi.

It should be noted that the replicon may be so designed that it is able to bring about containment of primary host cells inside a defined environment as well as of the replicon itself. When the replicon is harboured in one type of host cell, namely the primary host cells, the nucleotide sequence encoding the cell killing function should be regulatably expressed; this implies that when the primary host cell is subjected to certain conditions, e.g. as present within a defined environment where its presence is desired either for reasons involving the production of a specific product or because it has other functions such as degradation of a pollutant, the nucleotide sequence encoding the cell killing function is not expressed, and the host cells remain viable and able to fulfil their function. However, when the primary host cells are subjected to a specific change in environmental conditions, the cell killing function is expressed to kill the primary host cells harbouring the replicon.

It may also be possible, as part of the process of manufacturing a specific product, deliberately to kill the primary host cells present in, e.g., a fermentation vessel, by providing conditions under which the cell killing function is expressed. This procedure would be in accordance with the requirements stipulated by certain health authorities that genetically engineered organisms must be killed before leaving the fermentation vessel.

The principle of the present invention of obtaining biological containment by introducing a replicon carrying a nucleotide sequence encoding a cell killing function in a primary host cell may make it possible to use a wild-type strain as the primary host cells, e.g. cells used in the industrial production of a biosynthetic product. This has the important advantage over the use of mutated, attenuated strains which have hitherto been employed as a safety precaution as indicated above that it is not necessary to use specific growth conditions such as specific media containing one or more particular growth factors required by the mutated organism for growth, thus reducing the cost of the media employed and allowing a wider range of media components to be employed. Furthermore, the wild-type organisms may be better suited for genetic manipulations or show improved fermentation properties, or they may be ones which produce a specific, desired biosynthetic product, but which have hitherto not been permitted for use in large-scale production.

Should the replicon become taken up by another type of host cell, the secondary host cell, which is usually a wild-type organism found in the natural environment to which the primary host cells or optionally a medium in which the primary host cells have been grown are released, the nucleotide sequence encoding the cell killing function may be regulatably or constitutively expressed; in either case, the secondary host cell will be killed when expression of the cell killing function is no longer repressed or inhibited.

In some cases, the size of the DNA fragment comprising the nucleotide sequence coding for the cell killing function is not significant for its use according to the invention. However, it is often preferred that the nucleotide sequence coding for the cell killing function is present on a small DNA fragment which is advantageous in view of the fact that the copy number of the replicon usually becomes lower when the total size of the replicon is increased. Accordingly, insertion of the DNA fragment coding for the cell killing function with the purpose of obtaining a biological containment does not lead to any substantial decrease in the yield of a desired biosynthetic product also encoded by the replicon when the DNA fragment encoding the cell killing function only comprises a short sequence. Advantageous nucleotide sequences coding for a cell killing function have a size of 1500 nucleotides or less, preferably 1000 nucleotides or less, such as 500–200 nucleotides or less.

One way according to the invention in which the expression of the cell killing function may be regulated is by providing a replicon in which the expression of the cell killing function is regulated at the level of transcription. The regulation at the level of transcription may be carried out in various ways, but the regulation preferably takes place by means of a promoter regulated by one or more factors. These factors may either be ones which by their presence ensure expression of the nucleotide sequence encoding the cell killing function or may, alternatively, be ones which suppress the expression of said nucleotide sequence so that their absence causes the cell killing function to be expressed. Thus, when a primary host cell is released to the surrounding environment or when a recombinant DNA molecule is taken up by a secondary host cell, i.e. outside the defined environment of experiment or production or a specific restricted environment to which an organism has been released for a specific purpose, the promoter and optionally its associated regulatory sequence is activated by the presence or absence of one or more of these factors to effect transcription of the nucleotide sequence encoding the cell killing function whereby a cell killing product is produced and the host cells are killed.

Factors regulating promoter activity may be selected from a wide variety of factors. Principally, the expression of the gene encoding the cell killing function may be determined by the environmental conditions or the physiological state of the cells, or by a cyclical or stochastic event. In the present context, the term "cyclical event" is understood to mean a cyclically recurring event causing changes in certain factors known to be factors useful in influencing the expression of the cell killing function such as temperature conditions, changes in light intensity or hormonal changes. The term "physiological state of the cells" denotes factors such as cell density or growth phase of the cells.

Advantageous factors according to the invention, since these are most easily regulatable, are the presence or absence of a certain chemical in the environment or the physical conditions in the environment such as the temperature prevailing in the environment or other physical characteristics (e.g. the intensity of the light in the environment). Thus, it is possible to envisage containment systems in which the nucleotide sequence coding for the cell killing function is expressed when a certain chemical present in the fermentation medium of the primary host organism is not present in the environment to which the primary host cell is released, i.e. when primary host cells are accidentally released from, e.g., fermentation tanks to the surrounding environment, a factor required for the growth or survival of the cells is no longer present, or the factor may be exhausted from the medium with the same effect. The promoter regulating the transcription of the nucleotide sequence coding for the cell killing function may also be activated by a chemical which is not present in the fermentation medium of the primary host organism, but which is present in the environment in sufficient quantities to activate the promoter. Similarly, the promoter may be one which is activated by a shift in temperature, which, in the containment principle involving the replicons of the invention, usually implies a shift from a higher temperature in a fermentation vessel or the intestinal tract to a lower temperature prevailing in the outside environment, or the intensity of light in that the promoter may be a promoter which is activated in the presence of light of a sufficient intensity, but inactive in the darkness prevailing in the fermentation vessel which is the defined environment of the primary host.

Where primary host organisms are ones which are released to the natural environment in a controlled fashion, e.g. to a restricted area of land or to the intestinal tract of an animal, the regulatable promoter may be one which is regulated by chemical means, i.e. by the presence or absence of a certain chemical in the environment of the cells, but is most advantageously a promoter which is activated cyclically, e.g. by changes in temperature, or by a stochastic event. The term "stochastic event" is intended to indicate an event which occurs at random with a certain frequency per cell per generation or frequency per time unit which, according to the invention, results in the killing of the cells in which the activation of expression of the killing function occurs. The stochastic event may be occasioned by periodic inversions of the region carrying the promoter or excision of a sequence carrying a negative regulatory element. The effect of establishing cell killing by stochastic events is that the population of host cells will have a decreased competitiveness compared to populations of naturally occurring organisms.

It should be noted that the promoter used to initiate transcription of the nucleotide sequence coding for the cell killing function is preferably a promoter which is able to cause expression of the nucleotide sequence coding for the cell killing function in a wide range of host organisms in order to ensure a general applicability of the principle of the invention.

In case of a regulatable transcription of the cell killing function, the regulatory sequences may, for instance, be isolated from the bacterial operons involved in the biosynthesis of amino acids or from bacterial genes, the transcription of which is activated late in the stationary growth phase or from bacterial genes involved in the synthesis of surface structures (fimbriae). Examples of suitable promoters are *E. coli* trp which is activated in the absence of tryptophan, the bacteriophage λ $P_R$ and $P_L$ promoters controlled by temperature-sensitive regulating factors, the *B. subtilis* sporulation gene promoters which are activated during sporulation, and the *E. coli* and Salmonella fimbriae gene promoters which are activated stochastically.

In case of chemically regulatable promoters, the chemical, the presence or absence of which determines the activation of the promoter, may suitably be selected from carbon or nitrogen sources, metabolites, amino acids, nucleosides, purine or pyrimidine bases or metal ions. When the chemical is one which, when present, suppresses promoter activity, it should preferably be one which rarely occurs in the natural environment in such concentrations that the promoter would not be activated when the host organisms are released to the natural environment. One example of a suitable promoter in, e.g., an organism such as *E. coli* is the trp promoter which is repressed in the presence of a sufficient concentration of tryptophan in the cell environment, but which is derepressed in the absence of sufficient quantities of tryptophan in the environment. A containment system using the trp promoter might therefore comprise a quantity of tryptophan in, e.g., a fermentation vessel to repress the promoter which is derepressed when the host organisms are released from the fermentation vessel to the environment which usually contains very low concentrations or no tryptophan at all.

Promoters which are activated stochastically, by periodic inversions of the promoter region (in the present context, this is also termed an "invertible promoter" and "inversional switch promoter") and which are useful for the purposes of the present invention, also include the hin, cin and gin promoters (R. H. A. Plasterk et al., *Proc. Natl. Acad. Sci. USA* 80, 1983, pp. 5355–5358; G. Mertens et al., *EMBO J.* 3, 1984, pp. 2415–2421; J. Zieg and M. I. Simon, *Proc. Natl. Acad. Sci. USA* 77, 1980, pp. 4196–4200). One invertible promoter which has been found to be particularly useful due to its relatively small size is the fimA promoter which is one *E. coli* fimbriae gene promoter having the following sequence:

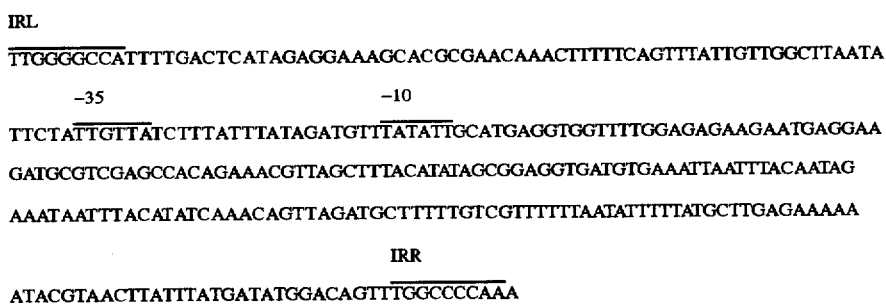

where the direction of transcription is from left to right and the proposed promoter consensus sequences are indicated at −35 and −10 (P. Klemm, *EMBO J.* 5, 1986, pp. 1389–1393).

The activation (inversional switch) of this promoter is regulated by the gene products of two genes which for the present purposes have been termed the "on" gene and the "off" gene, the on gene product inducing a switch from off (inactive) to on (active), and the off gene product inducing a switch from on to off. In a wild-type *E. coli* cell where the fimA gene and its associated promoter is present in one copy on the chromosome, the inversional switch occurs with a switching frequency of one cell/1000 cells/generation. It is, however, possible to regulate the frequency of the inversional switch (substantially) according to need/as required by regulating the dosage of expression of the on and off genes. This may, for instance, be effected by means of suitable promoters inserted to transcribe into the on and off genes. The frequency of transcription initiation by these promoters will then determine the relative dosage levels of the on and off genes formed. Thus, when relatively large amounts of the off gene product are formed, the frequency of the inversional switch to the "on" position is lower than when relatively larger amounts of the on gene product are formed.

An alternative way of obtaining host cell containment according to the invention is to regulate the expression of the nucleotide sequence coding for the cell killing function at the level of translation. This may be done by providing an antisense RNA which inhibits the translation of the messenger RNA (mRNA) specifying the cell killing function in the primary host cell. The expression of the nucleotide sequence coding for the antisense RNA may be either constitutive or regulated, for instance to allow for an increase in the copy number of the replicon carrying the cell killing function, the only requirement being that the strength of the promoter is such that sufficient quantities of antisense RNA are produced per unit time to completely inhibit the translation in the primary host cell of the mRNA specifying the cell killing function. When such a replicon is transferred to any type of secondary host cell in which the nucleotide sequence coding for the cell killing function is transcribed and in which the product of that nucleotide sequence exerts a cell killing function, the absence in the secondary host cell of the nucleotide sequence coding for the inhibitory antisense RNA results in translation of the mRNA specifying the cell killing function which in turn causes the death of the secondary host cell. For all practical purposes, this means that the expression of the nucleotide sequence coding for the cell killing function is regulated by the presence of the antisense RNA, the gene sequence of which is suitably present on another replicon in the primary host cell.

In accordance with the invention, the expression of the antisense RNA may be regulated as described above for the promoter initiating transcription of the nucleotide sequence coding for the cell killing function by a defined environmental factor influencing the activity of the promoter from which the nucleotide sequence coding for the antisense RNA is transcribed. These environmental factors may be the same as those mentioned above, and comprise the presence or absence of a certain chemical in the environment, the temperature of the environment or the intensity of light in the environment of the primary host cell. Suitable promoters may, for instance, be isolated from bacterial operons involved in various catabolic pathways, in osmo-regulation or in heavy metal resistance. Suitable promoters activated by a chemical are the lac, ara and deo promoters which are activated by the presence of lactose, arabinose and pyrimidine nucleosides, respectively, and osrA which is induced in the presence of high concentrations of $K^+$, and the promoter for the mercury resistance gene of Tn501 which is induced by heavy metal ions. When the antisense RNA is present in the primary host cell, translation of the mRNA specifying the cell killing function is inhibited through interaction between the two RNA species. However, if the primary host cell is released from its intended environment, the environmental conditions determining the promoter activity will be changed so that the nucleotide sequence coding for the antisense RNA which has been designed to be expressed in a certain environment, will no longer be expressed, and the primary host cells will die. Similarly, if the recombinant DNA molecule carrying the nucleotide sequence coding for the cell killing function is taken up by a secondary host mechanism, no antisense RNA will be present to prevent production of the cell killing product, and the secondary host cells will also die.

If the nucleotide sequence encoding all or part of the antisense RNA is inserted between directly repeated nucleotide sequences of a sufficient size, recombination between the repeats will occur in recombinationally proficient cells with a frequency which to some extent can be experimentally determined by varying the lengths of the repeats and/or the distance between the repeats, leading to death of the cell when recombinational excision of the negatively acting regulatory element takes place. Apart from this, expression of the antisense RNA may also be regulated stochastically, for instance from an invertible promoter to bring about an inversional switch so that the antisense RNA is no longer expressed. This promoter may advantageously be the *E. coli* fimA promoter.

Nucleotide sequences encoding a cell killing function to be inserted in a replicon of the invention may be derived from a wide variety of sources such as bacterial plasmids, bacterial chromosomes, procaryotic viruses, eucaryotic plasmids, eucaryotic chromosomes, eucaryotic viruses, eucaryotic mitochondria or eucaryotic chloroplasts; they may also be produced synthetically according to standard procedures. One example of a nucleotide sequence expressing a cell killing function is the hok gene from the parB region of the plasmid R1, a region which has previously been shown to be involved in the stable maintenance of R1 within a bacterial population, cf. the disclosure of International Patent Application No. PCT/DK83/00086, Publication No. WO 84/01172. An important feature of plasmid stabilization by parB has been found to be the toxic effect of the hok gene product which is exerted if the translation of hok mRNA transcribed from the parB region of R1 is no longer suppressed by a hok mRNA hybridizing antisense RNA, sok, which is also transcribed from the parB region. Loss of the R1 plasmid from a bacterial cell presumably leads to a change in the ratio between hok mRNA and sok RNA in the plasmid-free cell, presumably due to differences in the half-life of the two RNA species, and ultimately to translation of hok mRNA when insufficient concentrations of the inhibitory sok RNA are present in the cell, which causes the death of the plasmid-free cell.

The nucleotide sequence coding for a cell killing function may be combined with promoter sequences such as those described above or combined within the primary host cell with a sequence coding for an antisense RNA as described above. These sequences may be derived from natural sources such as those mentioned above for the cell killing function, or may be produced synthetically.

This natural system is utilized in accordance with the principles of the present invention to design a system of biological containment utilizing the hok gene from R1 to confine recombinant organisms to a defined environment such as a fermentation vessel, to confine recombinant DNA molecules or viruses to specific host cells or host cells in a defined environment and finally to confine, in time and space, environmentally released recombinant organisms or vectors carrying recombinant genetic information.

In accordance with the present invention, host cell containment, such as containment of an *E. coli* host containing a recombinant DNA molecule such as a bacterial plasmid, may be obtained if the hok gene is inserted by standard recombinant DNA techniques together with DNA sequences containing a suitable promoter/regulatory region in such a way that the transcription of the hok gene is, at least partially, controlled by the promoter/regulatory sequences; if specific environmental conditions determined by the nature of the promoter/regulatory sequences used are not met, the promoter/regulatory region is derepressed, resulting in transcription of the hok gene which in turn leads to cell death. Alternatively, it may be possible to use another form of regulation, for instance translational control as described above by using an antisense RNA inhibition of hok mRNA translation. Such a system may be devised so that the hok gene is constitutively expressed from the plasmid-borne gene while the translation of hok mRNA is counteracted by the synthesis of a properly designed antisense RNA, the gene coding for which is expressed from a regulated promoter as described above whose activity depends on the presence of one or more specific environmental factors. When these factors are no longer present, the promoter will no longer be active, and therefore antisense RNA will no longer be expressed and no longer inhibit the translation of hok mRNA so that the toxic product is formed and the host cells are killed.

As described above, the presence of the parB region (containing the hok and sok genes) on a plasmid stabilizes plasmid inheritance. This basic stabilization principle may be utilized according to the present invention by inserting a regulatable, preferably strong promoter upstream of the hok and sok genes in such a way that transcription from the promoter results in synthesis of the Hok protein, because the hok mRNA is expressed in excess relative to the inhibitory sok antisense RNA. Thus, under conditions where no transcription from the inserted promoter takes place, the plasmids are stably maintained in the growing population of cells, while under different conditions, e.g. in the outside environment or in a secondary host cell, transcription of the inserted promoter takes place, and the cells are killed.

In accordance with the present invention, it is contemplated, in host organisms in which the R1 hok gene product will not be toxic, to employ sequences which are homologous to or related to the R1 hok gene from other organisms which will be active in those organisms according to the same principles as those established for the R1 hok gene product. The term "homology" is used here to denote the presence of any degree of complementarity between a given probe and the nucleic acid species being analyzed. The "degree of homology" is expressed as the fraction of complementary bases in a duplex nucleic acid molecule formed between a given probe and the nucleic acid species being analyzed. The minimum degree of homology which is detectable is a function of the experimental conditions employed during hybridization and of characteristics of the probe and the nucleic acid species being analyzed. Such homologous sequences have been found within the chromosomal DNA of a large number of bacterial species (including gram-positive bacteria), within the mitochondrial DNA of the yeast, *Tetrahymena pyriformis* and within human cells as well as within pea chloroplast DNA, all of which have a DNA sequence related to the R1 parB sequence as determined by DNA/DNA hybridization. Thus, the invention also relates to replicons which carry a nucleotide sequence which is homologous to the hok gene.

The present invention also relates to a primary host cell which harbours a replicon as described above. The cell may also comprise a nucleotide sequence coding for an antisense RNA inserted in the cell genome as described above. The primary host cell may be selected from a wide variety of cells such as bacteria or eucaryotic organisms such as unicellular organisms, e.g. yeasts or fungi, cells derived from the tissues of multicellular organisms such as plants, animals or fungi.

In a further aspect, the present invention relates to a nucleotide sequence which encodes a cell killing function. The nucleotide sequence may further comprise a sequence regulating the transcription of a sequence encoding the cell killing function. The regulatory sequence may be a promoter with the features and the functions described above.

The invention further relates to a nucleotide sequence which encodes an antisense RNA capable of inhibiting the translation of an mRNA specifying a cell killing function. As described above, this nucleotide sequence is preferably inserted into the cell on another replicon. The nucleotide sequence coding for the antisense RNA may either be expressed constitutively, or its transcription may be regulated from another nucleotide sequence which, for instance, may be a promoter regulated by one or more factors as described above.

In an important aspect, the present invention relates to a method of containing a biological system, which comprises introducing into the biological system a nucleotide sequence encoding a cell killing function which sequence is regulatably expressed under certain conditions, and which is regulatably or constitutively expressed under different conditions under which the biological system is maintained.

In the present context, the term "biological system" refers to any structured biological material capable of reproduction such as nucleic acid (DNA or RNA) sequences, infectious agents such as viruses, bacteria or unicellular eucaryotic organisms, e.g. yeasts or fungi, or multicellular organisms such as plants, insects, etc., as well as cells derived from the tissues of multicellular organisms. The term "containment" indicates that the spread of the biological system from a specific restricted environment where specific conditions prevail and where its presence is desired, is limited or that the existence of the biological system is limited to a certain period of time.

The containment is performed by maintaining the biological systems under certain conditions which ensure that the cell killing function is not expressed. These conditions may be intra- or extracellular, and may comprise the phenotype and physiological state of the host organisms, host-vector relationships, the environmental conditions prevailing for the biological system, or a cyclical event. When any one of these conditions is changed, the cell killing function may be regulatably or constitutively expressed so as to kill the host organism carrying the nucleotide sequence encoding the cell killing function. Additionally, the conditions comprise stochastic events.

When the biological system comprises cells, these may be contained under defined environmental conditions by inserting into the cells a nucleotide sequence containing a sequence encoding a cell killing function and a sequence regulating the transcription of the sequence coding for the cell killing function, or, separately, a nucleotide sequence encoding a cell killing function and a nucleotide sequence encoding an antisense RNA inhibiting, when expressed, the translation of the mRNA specifying the cell killing function, as described above.

In accordance with the principles of the present invention, the nucleotide sequence coding for the cell killing function is preferably carried on a replicon. The nucleotide sequence coding for the antisense RNA may be inserted in the cell on another replicon. The cells contained according to the method of the invention may be selected from bacteria or eukaryotic organisms.

Apart from providing containment of host organisms to exist only under defined conditions, the containment method according to the present invention also provides containment of a replicon to a primary host cell by inserting into the replicon a nucleotide sequence encoding a cell killing function, the nucleotide sequence being regulatably transcribed from a regulatory sequence which is regulated by one or more factors, at least one of which is encoded by a nucleotide sequence present exclusively in the genome of the primary host cell.

Alternatively, the replicon may be contained to a primary host cell by inserting into a replicon a DNA fragment from which is constitutively expressed an mRNA encoding a cell killing function, the translation of which is inhibited by an antisense RNA transcribed from another nucleotide sequence inserted into the primary host cell, the nucleotide sequence coding for the antisense RNA being constitutively expressed or expressed from a promoter regulated by one or more factors such as one of the factors described above. The replicon may also be so designed that, apart from being contained to a primary host cell, it is also contained to cells of the same species and a definable range of secondary host cells, i.e. cells in which the factors responsible for regulating the expression of the cell killing function are also present.

As will be apparent from the above disclosure, the biological containment method of the present invention is a highly versatile method which is applicable to a wide range of host cells and replicons to allow an active biological containment not only of attenuated organisms but also of wild-type strains intended either for production of a specific biosynthetic product or for release to the natural environment (the outside environment or the intestinal tract of an animal); furthermore, by the present method, active containment of a given replicon to a specific host is obtained.

It is further contemplated that the principle of the present invention involving a replicon carrying a nucleotide sequence encoding a cell killing function which is expressed under certain predefined conditions, may be utilized in the preparation of live vaccines. Such vaccines, based on non-pathogenic (e.g. attenuated) strains of otherwise pathogenic microorganisms or viruses have been known for a long time. Prominent examples of agents used in live vaccines are the vaccinia virus, the attenuated poliovirus (derived by Jonas Salk) and the Bacille Calmette-Guerin (attenuated *Mycobacterium tuberculosis*). Live vaccines are advantageous in that they confer a prolonged, if not lifelong, immunity against the pathogenic agent in question. Furthermore, they are generally cheaper and easier to administer than vaccines based on inactivated (killed) pathogens or purified proteins.

However, the use of live vaccines has been limited since it is often difficult to obtain the right combination of attenuation, viability and relevant immune response. Furthermore, the deliberate release of genetically engineered bacteria to the environment, whether external or internal, is currently not allowed in any country for reasons of public concern as to the possible long-term environmental impact, especially the risk of permanent establishment of the genetically engineered bacteria in the environment.

The present invention has made it possible to circumvent the problems associated with the use of live vaccines by introducing in a suitable host organism (a primary host cell as defined above) a nucleotide sequence encoding a cell killing function, the expression of which is determined by a stochastic event; a nucleotide sequence encoding a desired epitope for immunization (antigenic determinant) from a pathogenic agent; as well as means for transporting the epitope, when expressed, to the outer surface of the cell, i.e. translocating it across the cellular membrane systems. The nucleotide sequence encoding the cell killing function and the nucleotide sequence encoding the epitope may be present on the same replicon or on separate replicons. In this connection, the cell killing function may be any one of those indicated above. A currently preferred cell killing function is the one encoded by the R1 hok gene.

The host cell may be any organism which is suited for being administered to a mammal, e.g. a human being, to be immunized by the vaccine. Conveniently, the host cell is provided with genetic information for the expression of adhesins, for instance a bacterium which, in nature, expresses adhesins by means of which they adhere to the surface of epithelial tissue. (An adhesin may be defined as a structure responsible for adhesion of the bacteria to receptors present on epithelial surfaces.) This is an important property of the host cell since it enables it to establish itself in a specific environment particularly advantageous for immunization purposes, e.g. where the type of the immune response is optimal, i.e. secretory IgG and IgA, thus providing a superior protection of epithelial surfaces. It should be noted that, in this context, the term "environment" defined above as a specific, restricted environment where specific conditions prevail should be understood to include tissues and epithelial surfaces in the body as well as cavities defined by such surfaces, such as the gastrointestinal tract, oral and nasal cavities, respiratory tract, urinary tract and reproductive organs. It is interesting to note that these areas coincide with those first exposed to infectious (pathogenic) agents. It is at present contemplated that the vaccine may most conveniently be administered as an oral vaccine, and consequently the host cell should in this case be one which is able to establish itself in the intestines and compete successfully with the numerous organisms already present in it.

Thus, examples of suitable primary host cells may be selected from Enterobacteriaceae, e.g. *E. coli*, or lactic acid bacteria, e.g. *Lactobacillus acidophilus*, Vibrionaceae and Pseudomonades. The organism, however, need not necessarily be one which is inherently capable of establishing itself in the intestines. One may also select a host organism according to other criteria such as its suitability for being subjected to recombination techniques or fermentation procedures, and provide it, by standard DNA recombination techniques, with genes expressing adhesins, should the organism so selected lack such functions enabling it to adhere to epithelial tissue.

The epitope for immunization may be introduced in the primary host cells by inserting a nucleotide sequence encoding the epitope into a replicon in accordance with standard recombination techniques which are well known in the art (as described in e.g. Maniatis et al., *Molecular Cloning: A Laboratory Manual*, Cold Spring Harbor, 1982). Thus, the replicon carrying the nucleotide sequence which codes for the epitope should further be provided with a suitable promoter, ribosomal binding site, translational initiation codon (ATG), to ensure expression of the epitope on the surface of the host cell. An essential feature of the vaccine according to the present invention is that the epitope should be presented on the surface of the host cell in order to provoke an appropriate immune response in the mammal to be immunized. If the epitope is not naturally transported to the surface of the host cell, the nucleotide sequence encoding the epitope may be inserted into a gene coding for a naturally occurring cell surface protein, such as a fimbrillin (the structural subunit of fimbriae), to express a fusion protein which is translocated to the cell surface.

As indicated above, expression of the cell killing function is, in the case of a vaccine according to the invention, determined by a stochastic event which, as explained above, will typically be brought about by a periodic inversional switch of a promoter to transcribe into the nucleotide sequence encoding the cell killing function, i.e. a promoter subjected to an inversional switch from inactive to active with a frequency which may, for instance, be regulated by the respective levels of expression of an on and off gene, as explained above with reference to the fimA promoter. It may be expected that similar promoters are regulated by similar mechanisms. This makes it possible to adjust the frequency of the inversional switch so as to cause maintenance of a sufficient dosage level of the epitope in question for the period of time required to obtain a satisfactory immunization of the animal to which the vaccine is administered. Alternatively, the stochastic event may be brought about by a periodic inversional switch of a promoter transcribing a nucleotide sequence encoding an antisense RNA inhibiting the translation of the mRNA specifying the cell killing function, as explained above. A currently preferred promoter is the *E. coli* fimA promoter. Apart from this, expression of the cell killing function may be achieved by recombinational excision of the antisense RNA, as explained above. The genes encoding the stochastic transcription mechanism (i.e. the promoter and optionally the on and off genes) of the cell killing function are conveniently inserted in the host cell chromosome rather than on a plasmid, for instance by means of bacteriophages, in order to avoid loss of said genes as a result of loss of the plasmid from the cell. By regulating the frequency of the inversional switch, a certain predetermined percentage of the host cells will be killed in each generation. This ensures that the cell population cannot compete with the natural bacterial flora of, e.g., the intestines over a longer period of time.

By allowing the organism to become established in the intestinal environment for such a predetermined period of time before the cell killing function is expressed, it is possible to ensure that the dosage of the epitope to which the body to be immunized is exposed will be sufficiently large and last for a sufficient period of time to provide an adequate immunization. It is estimated that a satisfactory immunization may be obtained if the host cells are present in sufficient amounts in the defined environment for a period in the range of 15–30 days, dependent on the nature and activity of the epitope expressed from the host cell.

In principle, the epitope expressed by the primary host cell may be an epitope from any pathogenic agent against which it is desired to obtain immunity. Such pathogenic agents comprise viruses, bacteria or eukaryotic organisms such as fungi or protozoans. Examples of viruses from which epitopes to be used in connection with the live vaccine of the invention may be obtained, are viruses belonging to the families adenoviruses, herpetoviruses, papovaviruses, myxoviruses, orthomyxoviruses, paramyxoviruses, poxviruses, rhabdoviruses, arboviruses, or reoviruses. Other virus families of interest in this connection are the picornaviruses and retroviruses. Specific examples of viruses are influenza virus, parainfluenza virus, measles virus, mumps virus, rubella virus, rhinovirus, rabies virus, HTLV I and II virus, HIV viruses, hepatitis B virus and other viruses causing hepatitis, poliovirus, rotavirus, reovirus, Epstein-Barr virus, Herpes simplex I and II virus, cytomegalovirus, human papilloma viruses of various types, etc.

Examples of bacteria from which epitopes to be used in connection with the live vaccine of the invention may be derived, are enteric bacteria, e.g. pathogenic strains of *Escherichia coli*, *Salmonella spp.* such as *S. typhimurium*, *S. typhi*, *S. schottmülleri* and *S. choleraesuis*, *Vibrio cholerae*, *Shigella dysenteriae*; *Corynebacterium diphteriae*; *Mycobacterium tuberculosis*; *Neisseria spp.* such as *N. gonorrhoeae*, *N. meningiditis* and *N. catarrhalis*; *Pseudomonas spp.* such as *P. aeruginosa*; *Yersinia spp.* such as *Y. pestis*; *Moraxella spp.* such as *M. bovis*; *Staphylococcus spp.* such as *S. aureus*; *Streptococcus spp.* such as *S. pneumoniae* and *S. pyogenes*; *Bordetella spp.* such as *B. pertussis* and *B. bronchiseptica*; *Hemophilus influenzae*; *Treponema pallidum*; and *Clostridium spp.* such as *C. botulinum* and *C. tetani*.

Examples of pathogenic eukaryotic organisms, epitopes of which may be used in connection with the live vaccine of the invention, are fungi, e.g. *Blastomyces dermatitidis*, *Histoplasma capsulatum*, *Coccidioides immitis*, *Cryptococcus neoformans* and *Candida albicans*; protozoans, e.g. *Giardia lamblia*; *Trypanosoma spp.* such as *T. gambiense*, *T. rhodesiense* and *T. cruzi*; *Leishmania spp.* such as *L. donovani* and *L. tropica*; *Entamoeba histolytica*; *Naegleria spp.*; *Plasmodium spp.* such as *P. falciparum*, *P. vivax*, *P. malariae* and *P. ovale*; and *Isospora spp.* such as *I. belli* and *I. huminis*.

It is further contemplated that it will be possible to provide a combination vaccine against a variety of pathogenic agents by introducing, in the host cell, two or more nucleotide sequences encoding epitopes from different pathogenic agents in such a way that the epitopes are expressed as fusion proteins together with a fimbrillin, substantially as described above or transported to the cell surface by other means, e.g. due to the presence of a signal peptide, to provide a combination vaccine. In this case, too, the epitopes will be exposed on the surface of the host cell as parts of different fimbriae. An important advantage of this embodiment of the invention is that immunization may be effected simultaneously against a variety of pathogens, only a single administration of the vaccine being required.

In order to avoid any risk of contaminating the outside environment (i.e. the environment outside the animal to be immunized with the vaccine of the invention) with live primary host cells which pass from the defined environment in the animal in question where their presence is desired to the outside environment, for instance with the faeces in case of an oral vaccine, it should be possible to kill the host cells once they have passed into the outside environment. This may be accomplished by inserting an additional promoter (apart from the stochastic promoter) into the host cell, which promoter, when activated, transcribes into a nucleotide sequence encoding a cell killing function, thereby causing death of the host cell or any other cell (secondary host cell) which comes to harbour a replicon carrying the nucleotide sequence which codes for the cell killing function. In one embodiment, the additional promoter, when activated, transcribes into the same nucleotide sequence encoding a cell killing function as the one the expression of which is determined by a stochastic event. It would also be possible to insert this additional promoter to transcribe, when activated, into another nucleotide sequence encoding a second cell killing function (which may be identical to the first one) inserted on the same or another replicon as the nucleotide sequence coding for the first cell killing function. Activation of this additional promoter advantageously occurs as a result of, for instance, a decrease in temperature to below body temperature (about 37° C.) or by chemical induction, as explained above.

In this way, the non-viability in the outside environment of genetically engineered bacteria used in the live vaccine of the invention is ensured. In cases where the nucleotide sequence encoding the cell killing function and the gene coding for the epitope are present on the same replicon, the accidental spread of the recombinant replicon to secondary host cells, in this case usually wild-type organisms found in the outside environment, is substantially prevented. The presence of the nucleotide sequence coding for the cell killing function and the gene encoding the epitope on the same replicon therefore constitutes a preferred embodiment of the vaccine of the invention.

Apart from being useful in the preparation of live vaccines as described above, the principle of the present invention is further contemplated to be applicable to the development of vaccines based on killed pathogens. Until now, such vaccines (in the following also termed "killed vaccines") have been known to be less efficient than live vaccines. Without wishing to be limited to any particular theory, the present inventors believe that the diminished efficiency of killed vaccines may be ascribable to the way in which the pathogenic agents used in the vaccines are inactivated, which is usually by heat treatment or chemical inactivation with formaldehyde. This is thought to denature the antigen structures of the pathogen in question, giving rise to a less adequate immune response when the vaccine is administered and hence a less thorough immunization.

This problem may be circumvented by utilizing the measures of the present invention. Accordingly, it may become possible to produce a killed vaccine which comprises a pathogenic agent carrying one or more nucleotide sequences encoding a cell killing function, which pathogenic agent has been killed by the expression of one or more of said nucleotide sequences. In this way, the antigen structures of the pathogen will remain intact so that, theoretically, a more efficient immunization of the mammal to which the killed vaccine is administered will be obtained. The pathogen employed in the killed vaccine may be any one (or a combination) of those listed above as providing the genes coding for epitopes to be introduced in live non-pathogenic host cells for use as live vaccines.

Because of a low but definite risk of mutations affecting the killing function, this type of vaccine may only be of practical relevance in the field of veterinary medicine.

The expression of the cell killing function may be regulated at the level of transcription, e.g. by means of a regulatable promoter. Any one of the promoters discussed above may be employed. Alternatively, the expression of the cell killing function may be regulated at the level of translation as discussed above, e.g. by means of an antisense RNA inhibiting the translation of the mRNA specifying the cell killing function.

In a specific embodiment of the killed vaccine of the invention, the vaccine, when administered, comprises live pathogenic agents into which has been inserted a cell killing function which is activated in the body as a result of the environmental changes to which the pathogens are subjected, e.g. changes in temperature, pH or the presence of certain chemicals.

The vaccines of the invention (live or killed) may be formulated for oral or parenteral administration in accordance with usual practice in the field of human and veterinary medicine together with a pharmaceutically or veterinarily acceptable carrier or vehicle.

For oral administration of a live vaccine, it is preferred to protect the host cells against the gastric environment which tends to be detrimental to the viability of, e.g., many bacteria contemplated to be useful for the present purpose. This protection may, for instance, be provided in the form of an enteric coating.

1. Gramnegative and grampositive bacteria

Suitable replicons for genetic engineering in bacterial host cells may for example be plasmids capable of replicating in Enterobacteriaceae, e.g. pBR322 or R1 runaway replication plasmids (European Patent Application No. 83305438.0, Publication No. 0 109 150), or capable of replicating in gramnegative bacteria in general, e.g. plasmids derived from RSF1010 (Bagdasarian et al., *Gene* 16, 1981, pp. 237–242), or plasmids capable of replicating in grampositive bacteria such as *B. subtilis*, e.g pC194 and pUB110 (Lovett and Keggins, *Meth. in Enzymol.* 68, 1979, pp. 342–357). In order to biologically contain such bacterial plasmids or cells containing such plasmids according to the invention, the DNA fragment or DNA fragments comprising the R1 hok region can be inserted into the replicon in such a way that the R1 hok expression is governed by regulatable promoter(s) known to be recognized in the host cell in question, such promoters being either natural promoters or synthetic promoters, such as the *E. coli* trp promoter or the *B. subtilis* promoters governing expression of certain genes in stationary phase cells. As shown in the Examples, the R1 hok gene product is toxic in a wide range of gramnegative bacteria as well as in *B. subtilis* (cf. Example 16) and hence probably in all grampositive bacteria. If the R1 hok gene product is not lethal to the host cell in question—a definite requirement in order to establish the biological containment system—an R1 hok homologous sequence can be isolated from either the genome of the host cell in question (or a closely related bacterial species), from a plasmid naturally occurring in the host cell in question (or a closely related bacterial species), or from a bacterial virus and subsequently tested for hok-like activity in a manner similar to that described in the Examples for one *E. coli* chromosomal homologue of R1 hok.

Establishment of a biological containment system for, e.g., fermentation purposes involving the use of R1 hok or a nucleotide sequence homologous to the hok in bacteria thus Includes: selection of replicon and host cell; insertion into the replicon of the proper sequence comprising R1 hok or a nucleotide sequence homologous to the hok which is not expressed in the selected host cell under defined conditions; insertion into the replicon of a gene or genes encoding the useful product(s) to be produced in large quantities; introduction of the recombinant replicon into the bacterial host cell by standard techniques of bacterial transformation; cultivation of the replicon-containing host cells in a culture medium supplemented with the necessary nutrients including any exogeneous factor required for the containment system in question for the number of generations required to reach the desired cell concentration; and finally, harvesting of the cells and the medium from either of which the product in question can be isolated. If the cells are accidentally released to the outside environment, the promoter regulating the transcription of the hok or hok-like sequence will be activated, and the cells will be killed as a result of the expression of the hok or hok-like product or the promoter regulating the transcription of the antisense RNA is inactivated. Similarly, if DNA from the cells is transferred to other cells (secondary hosts), the promoter regulating the transcription of the hok or hok-like sequence is activated, and the cells are killed, which is also the case when the hok or hok-like sequence is regulated by an antisense RNA, in cells lacking a nucleotide sequence coding for the antisense RNA.

2. Yeast cells

The technical exploitation of recombinant DNA techniques in eucaryotic systems may be desired to obtain such post-translational modifications (specific proteolytic cleavages, glycosylation, etc.) of primary (eucaryotic) gene products that are not carried out in bacteria or are, at best carried out in a suboptimal manner. A widely used eucaryotic organism is the yeast *Saccharomyces cerevisiae* in which a naturally occurring plasmid, the 2µ replicon, has been adapted as a vector for expression of genes not naturally related to the 2µ replicon in *S. cerevisiae*. As described above, it is possible to isolate or construct a sequence to be inserted into a yeast replicon, e.g. the 2µ replicon, utilizing the principle of the R1 hok biological containment mechanism for containing yeast cells and plasmids.

Although the native promoters of R1 hok are not likely to be utilized in *S. cerevisiae* cells, the conservation of hok-like sequences in organisms which are only distantly related and the toxicity of R1 Hok to grampositive as well as gramnegative bacteria makes it reasonable to assume that the product of the R1 hok gene and of genes related to R1 hok (e.g. relB-orf3 or parl or other genes originating from bacterial genomes which show a homology at the sequence and functional level to R1 hok or similar genes isolated from bacterial plasmids) should be tested for their ability to kill yeast cells, such as *S. cerevisiae*. In practice, this will entail isolating the coding region of the hok gene or hok-like gene and linking the coding region to a suitable regulatable yeast cell promoter, the resulting replicon being finally introduced, by standard methods, into yeast cells, and the effect of expression of the hok or hok-like gene is investigated. If cell death ensues, a usable hok or hok-like gene has been identified.

Alternatively, sequences identified in DNA from yeast cells with homology to parB or relB-orf3 can be isolated, linked to a proper yeast cell promoter, inserted into the 2µ replicon and following introduction of the recombinant replicon into *S. cerevisiae*, tested for their ability to kill the cell. From a hok gene or a hok-like gene shown to be toxic upon expression for e.g. *S. cerevisiae*, a biological containment system identical to or analogous with the R1 hok system can be generated by imposing a regulatory loop (a regulatable promoter or a gene encoding an antisense RNA regulated by a proper yeast promoter) as previously discussed in the description of the general strategy. The resulting regulatable yeast hok sequence or hok-like sequence can be inserted in any yeast replicon, e.g. the 2µ replicon or derivatives thereof into which genes not naturally related to 2µ have been inserted with the intention of obtaining expression of the inserted genes, with the purpose of biologically containing cells and/or recombinant replicons. The replicon can be introduced into yeast cells, e.g. *S. cerevisiae* cells, by transformation or protoplast fusion, and following selection of cells carrying the replicon, these can be further grown into a large-scale culture in the appropriate culture medium supplemented with the necessary nutrients as well as any exogeneous factor(s) required for the containment system in question. The culture of cells harbouring the replicon in question is then harvested, and any useful product expresed from the replicon can be isolated from either the yeast cells or the culture medium, depending on the gene and the gene product in question. If the cells are accidentally released to the outside environment, the promoter regulating the transcription of the hok or hok-like sequence will be activated, and the cells will be killed as a result of the expression of the hok or hok-like product or the promoter regulating the transcription of the antisense RNA is inactivated. Similarly, if DNA from the cells is transferred to other cells (secondary hosts), the promoter regulating the transcription of the hok or hok-like sequence is activated, and the cells are killed, which is also the case when the hok or hok-like sequence is regulated by an antisense RNA, in cells lacking a nucleotide sequence coding for the antisense RNA.

3. Mammalian cells

The requirement for specific post-translational modifications may necessitate the expression of certain eucaryotic genes in mammalian cells, i.e. of human or animal origin, rather than in bacteria or yeast cells. Replicons that can be used as cloning vectors in eucaryotic cells are derived from chromosomes (ars replicons) from DNA viruses, e.g. SV40 and bovine papilloma virus, or from RNA viruses, e.g. retroviruses. The two DNA viruses mentioned can be maintained in a plasmid state in infected cells while most retroviruses (RNA-containing viruses) need to be genetically modified in order to exist as freely replicating DNA molecules rather than as chromosomally integrated copies of the viral DNA genome. It may be anticipated that large-scale cultures of cells containing the above-mentioned replicons into which a gene or genes not naturally related to the replicon has been inserted with the aim of obtaining expression of a useful product, will need to be contained as discussed in the section on procaryotic vectors.

In a manner similar to that described under the yeast cell system, a sequence containing a regulatably expresed R1 hok gene or a nucleotide sequence homologous to hok can be constructed, once a gene has been identified that exerts a hok or a hok-like effect in the host cell in question. A first step would thus be to insert the coding sequence of known hok or hok-like genes, irrespective of their origin, from bacterial plasmids, bacterial genomes or yeast cell genomes, into a replicon capable of replicating in the host cell in question in such a way that expression of the hok gene is obtained upon induction of expression, i.e. supplemented with all necessary regulatory sequences as is required for expression of a gene in the host cell in question. A promoter sequence suitable for insertion upstream of the hok or hok-like gene would be the mouse mammary tumor virus LTR (long terminal repeat sequence) which is inducible with steroid hormones or the region controlling the expression of the metallothionein gene which is inducible with metal ions. If cell death ensues upon induction of transcription, a hok gene or a hok-like gene has been identified for the host cell in question, and from this hok or hok-like gene, a replicon biological containment system can be constructed by a regulatory loop at the transcriptional/translational level as described above.

If none of the available hok or hok-like genes of bacterial or yeast origin exert a toxic effect in the mammalian host cells in question, novel hok-like sequences may be isolated from a mammalian genome (e.g. the sequences discovered in Tetrahymena mitochondrial DNA and in human cellular DNA) and subsequently tested for hok-like activity when properly expressed. The recommended strategy for the detection of novel hok-like sequences has been outlined above.

The use of the hok-like containment mechanism in mammalian cells will thus include: selection of replicon, e.g. a retroviral vector and selection of host cells which will depend upon the actual sequences governing the expression of the inserted hok-like nucleotide sequences; insertion into the replicon of such foreign genes which code for the useful product(s) to be produced into the replicon; introduction of the recombinant replicon into the mammalian cell type in question by standard techniques of DNA transfection or micro-injection; selection of cells containing the replicon in question; growth of the cells in a culture medium adapted for the cell type in question by the addition of necessary nutrients and growth factors as well as any exogeneous factor required for the containment system in question with the intention of obtaining a large-scale culture of cells expressing the gene encoding the useful product; and, finally, the culture can be harvested and the useful product isolated. If the cells are accidentally released to the outside environment, the promoter regulating the transcription of the hok or hok-like sequence will be activated, and the cells will be killed as a result of the expression of the hok or hok-like product or the promoter regulating the transcription of the antisense RNA is inactivated. Similarly, if DNA from the cells is transferred to other cells (secondary hosts), the promoter regulating the transcription of the hok or hok-like sequence is activated, and the cells are killed, which is also the case when the hok or hok-like sequence is regulated by an antisense RNA, in cells lacking a nucleotide sequence coding for the antisense RNA.

While particular types of replicons adapted for particular types of cells have been discussed in the detailed sections above, the general principle of utilizing the containment mechanism of the invention is the same, irrespective of the type of replicon and cell harbouring the replicon: the establishment of a host killing function and a regulatory function adapted to regulate the expression of the cell killing function in cells harbouring the replicon so that, under conditions where the cell killing function is expressed, the host cell is killed.

DESCRIPTION OF THE DRAWINGS

Reference is now made to the drawings, where

FIGS. 3a and 3b shows the nucleotide sequence of the parB$^+$ region. The 5' end of the upper DNA strand is positioned at right. The numbering of the bases are in accordance with the coordinates of the parB$^+$ region in FIG. 1. Ter denotes the stop codons of the only three open reading frames present in the nucleotide sequence consisting of more than 50 codons. fMet corresponds to the start codons of the same three open reading frames. The amino acid sequence of the hok gene product, starting at position +304, is shown below the DNA sequence—amino acid abbreviations are standard nomenclature. The underlined sequences designated "−10" and "−35" is the promoter structure for the sok gene.

FIG. 7a is a comparison of the amino acid sequences of the hok gene product and the relB-orf3 gene product. Conserved amino acids are with bold face types; amino acids representing conservative changes are underlined.

FIG. 7b shows the alignment of the nucleotide sequences of parB and orf3 of the E. coli relB operon (Bech et al., The EMBO Journal 4, 1985, pp. 1059–1066). The parB sequence is the upper strand, relB-orf3 the lower, coordinates as in FIG. 3. Vertical bars indicate conserved nucleotides. Numbers in brackets are coordinates of the relB nucleotide sequence as given by Bech et al. The two sequences are aligned so that the start codons of the two reading frames are at the same position—this is indicated with Met at position +304. The termination codons of the two reading frames are indicated with Ter at position +460.

*Escherichia coli*; lane 7: *Bacillus subtilis*; lane 8: *Bacillus circulans* PL236. Sizes of radioactively labelled marker (λ restricted with HindIII) are given in kilobases.

Figure 10:
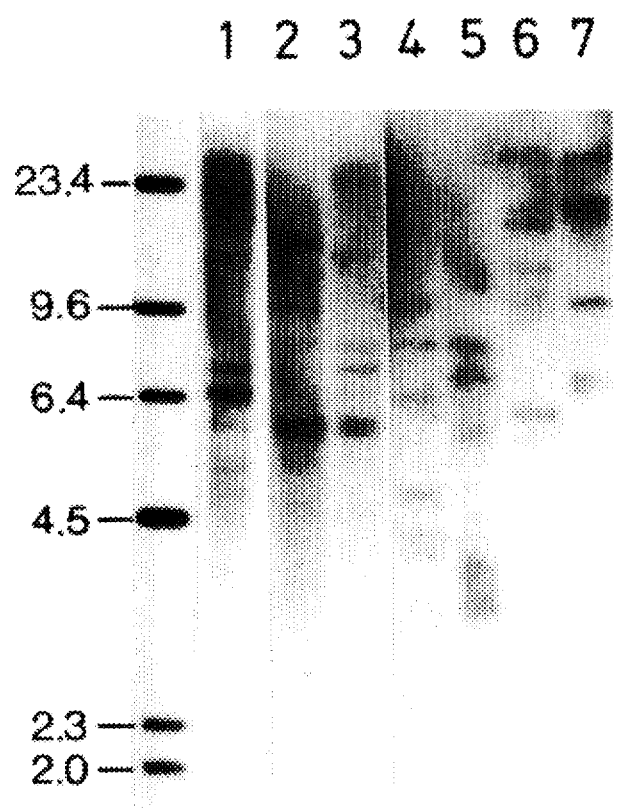

FIG. 10 shows 0.5–0.75 μg of EcoRI-restricted total DNA from various bacteria analyzed by filter hybridization using the relB-orf3 probe. The autoradiogram was exposed for 17 hours (lane 19) and 72 hours (lanes 2–7). Lane 1: *Serratia marcescens*; lane 2: *Pseudomonas fluorescens*; lane 3: *Pseudomonas putida*; lane 4: *Bacillus subtilis*; lane 5: *Bacillus circulans* PL236; lanes 6, 7: Lactobacillus. Sizes of radioactively labelled marker (λ restricted with HindIII) are given in kilobases.

Figure 11:
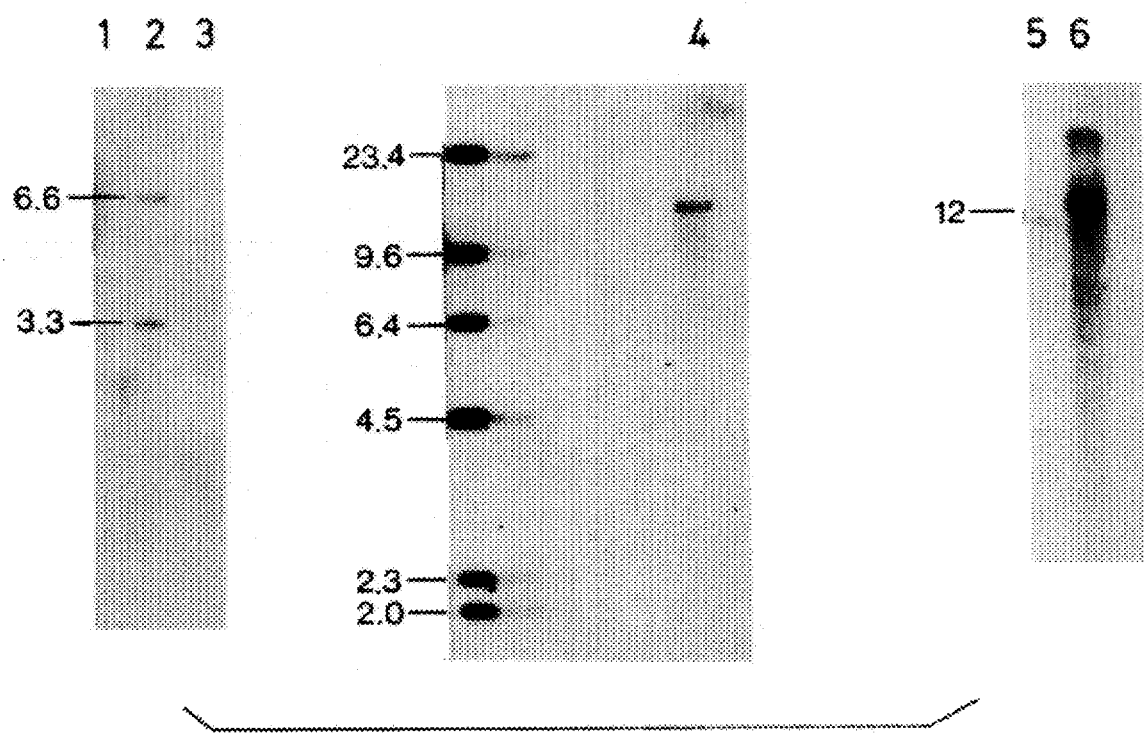

FIG. 11 shows filter hybridization analyses of DNA from eucaryotic cells using the relB-orf3 probe (lanes 1–4) as well as the R1 parB probe (lanes 5–6). The DNA was cleaved with EcoRI (lanes 1–3 and 5–6) or with PstI (lane 4). Lane 1: 5 μg of macronuclear DNA from *Tetrahymena thermophila*; lane 2: 5 μg of total DNA from *Tetrahymena thermophila*; lane 3: 0.25 μg of chloroplast DNA from *Pisum sativum*; lane 5: 5 μg of total cellular DNA from neuroblastoma; lane 6: 10 μg of total cellular DNA from embryonic liver. Sizes of fragments are given in kilobases.

Figure 12:
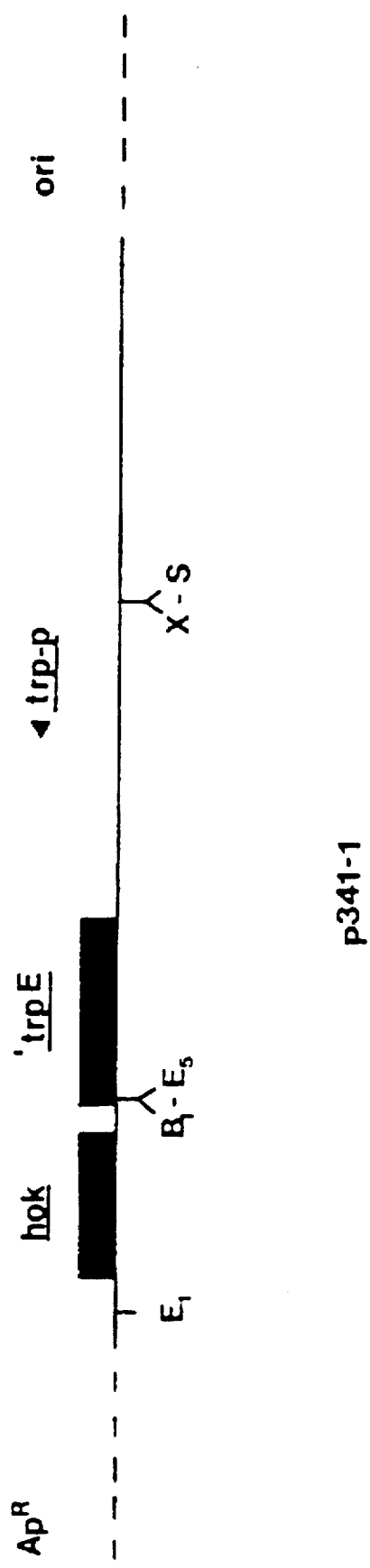

FIG. 12 shows a partial map of plasmid p341-1. The region presented here is the fusion between the hok gene and the promoter region from the trp operon of *E. coli* K-12 (obtained from plasmid pSGS8). In addition to the trp promoter (indicated by the arrow), the $NH_2$ terminal end of the trpE gene is also present (indicated as trpE). The broken lines represent pBR322 sequences from which the $Ap^R$ gene and the origin of replication are indicated. Restriction enzyme sites are shown as $E_1$ (EcoRI), $B_1$-$E_5$ (fusion of BamHI (filled in by DNA polymerase I) with EcoRV) and X-S (fusion of XhoI and SalI).

Figure 13:
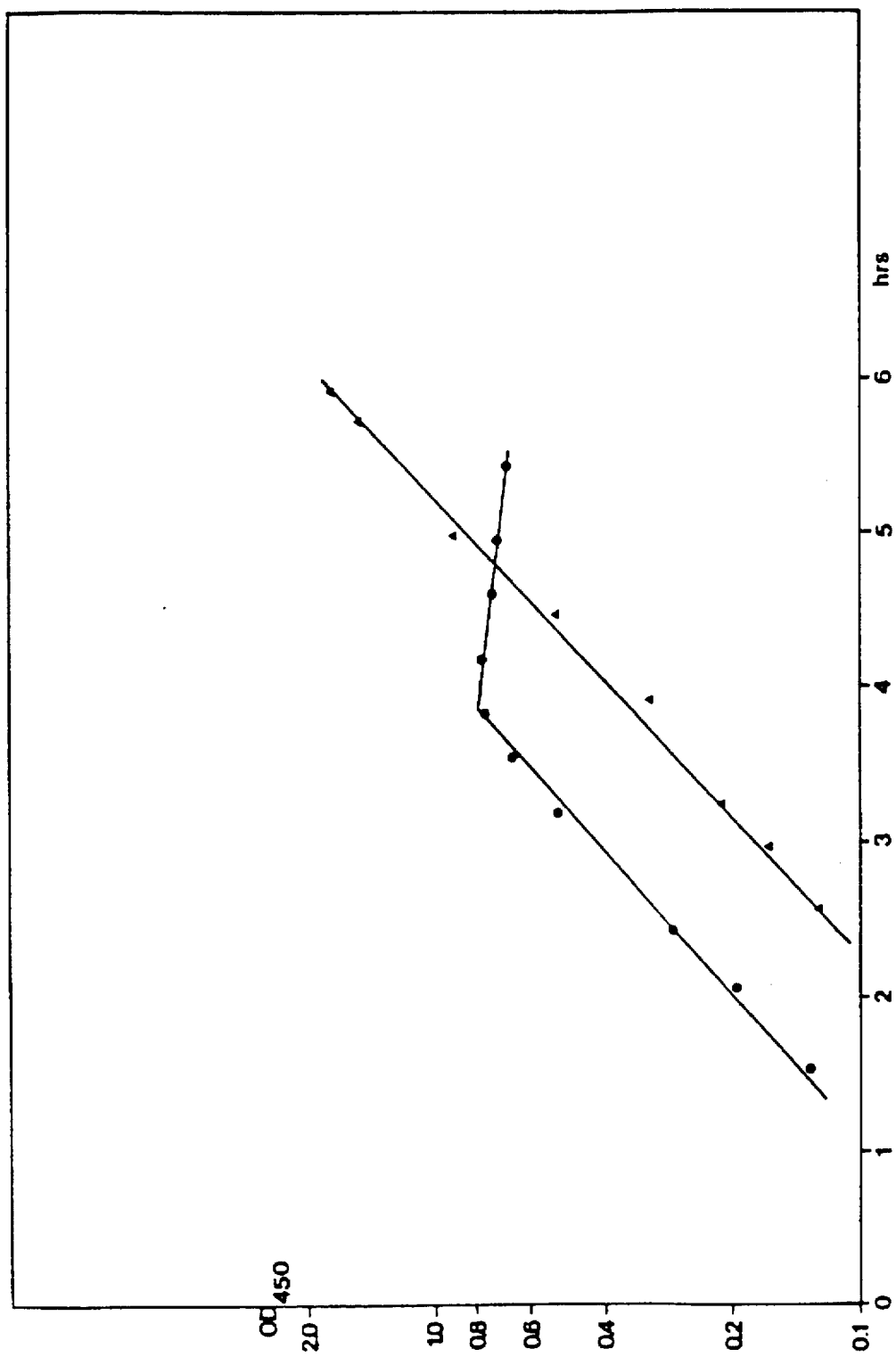

FIG. 13 shows growth curves for MC1000 (p341-1) (circles) and MC1000 (triangles) grown in A+B minimal medium supplemented with 0.2% glucose and 1% casamino acids at 37° C. The cell density is measured spectrophotometrically as $OD_{450}$.

Figure 14:
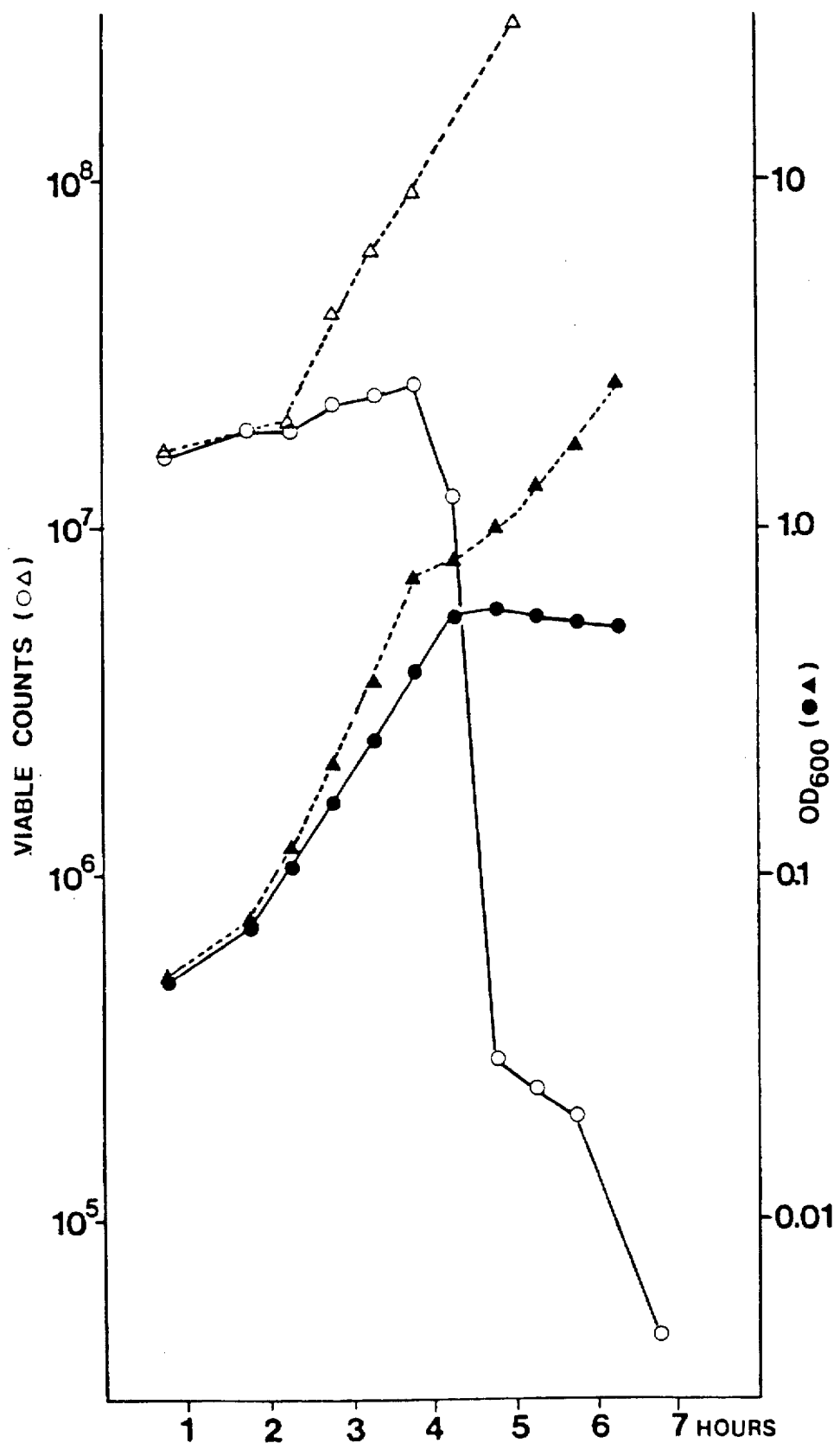

FIG. 14 is a graph showing viable counts ($OD_{600}$) of *E. coli* HB101 harbouring pNL7 (circles) or pBR322 (triangles), as a function of time. No exogenous tryptophan was added to the MA+B culture medium.

Figure 15:
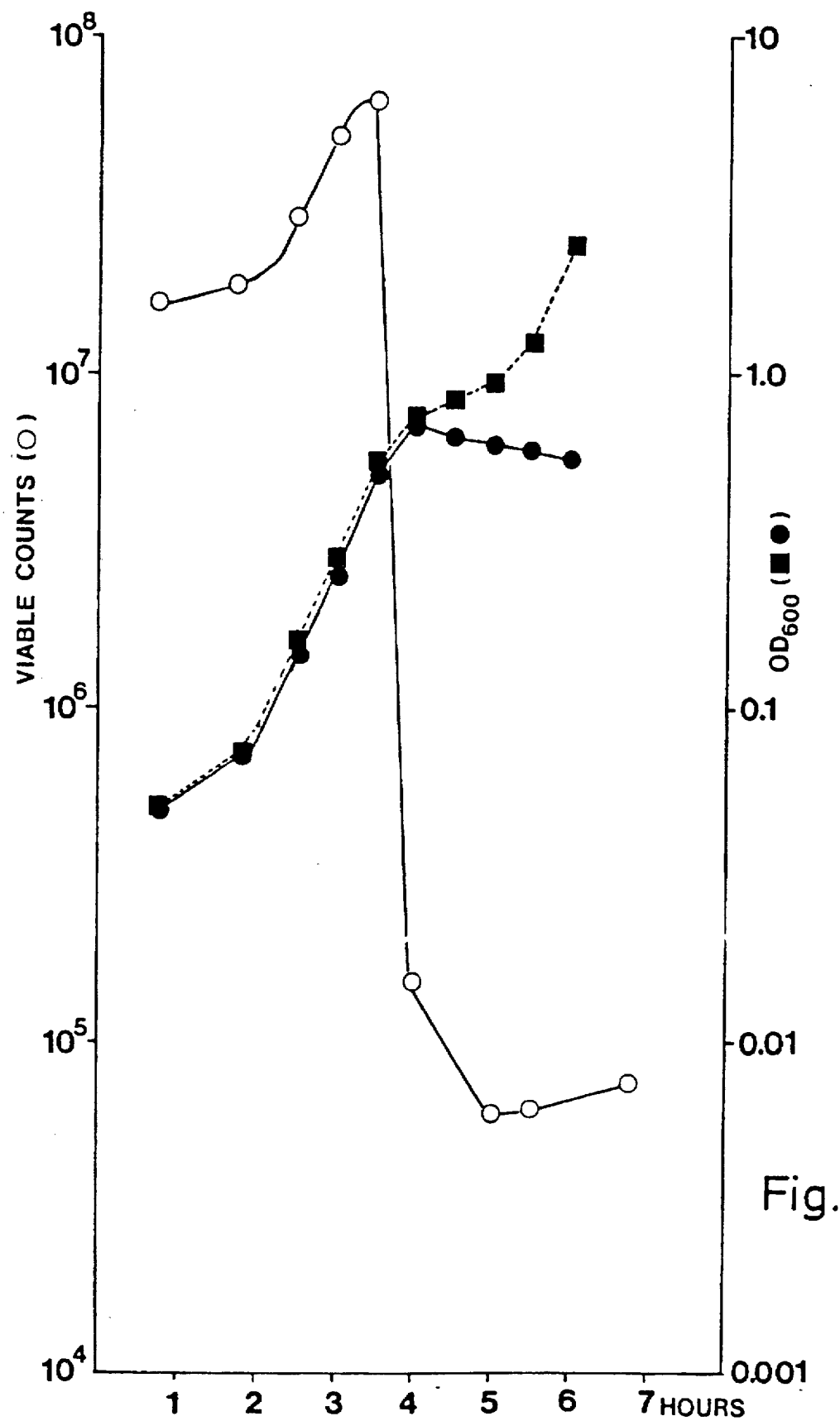

FIG. 15 is a graph showing viable counts ($OD_{600}$) of *E. coli* HB101 harbouring pNL7 (circles) and pBR322 (squares), as a function of time. 5 μg/ml tryptophan was added to the MA+B culture medium.

Figure 16A:
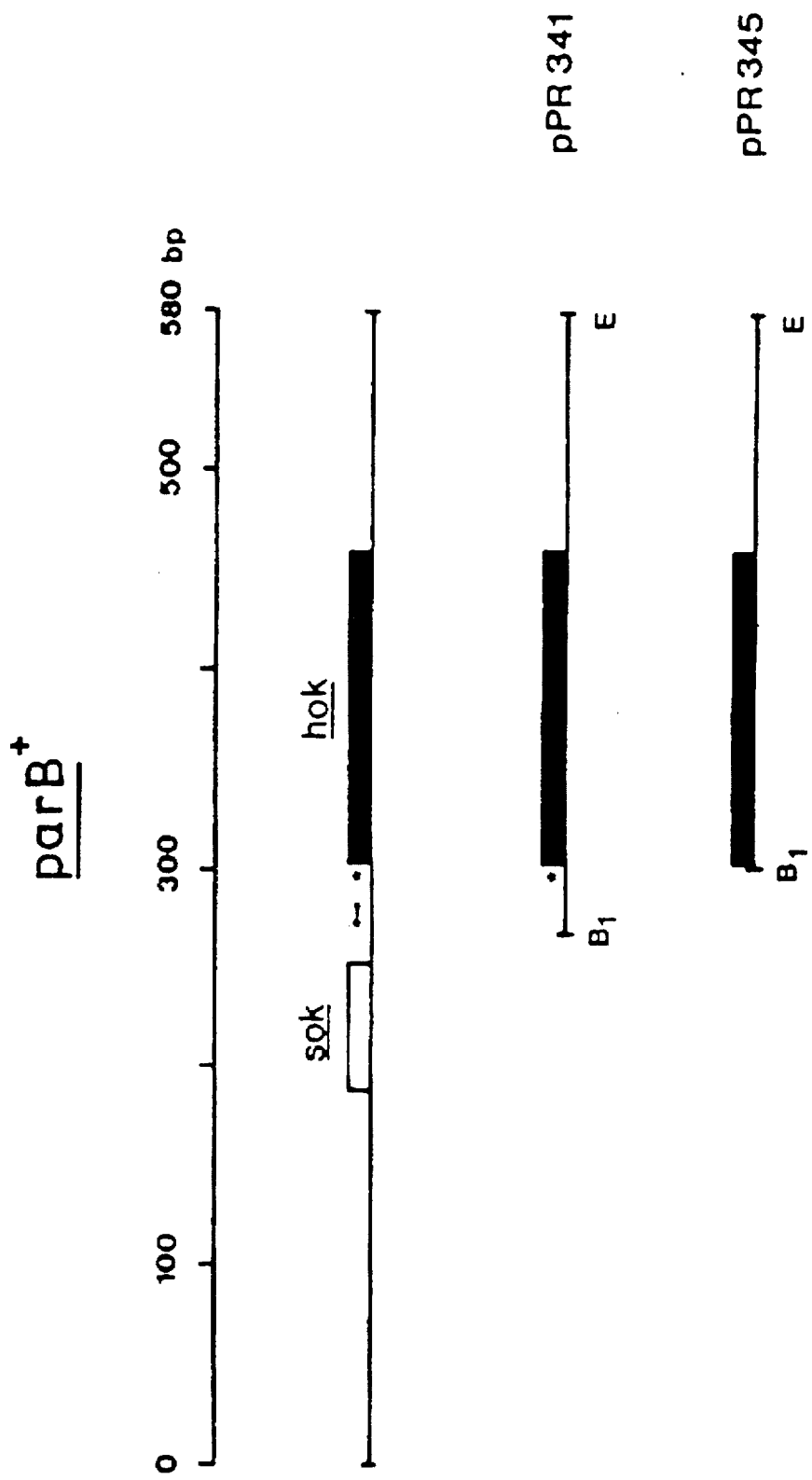

FIG. 16a shows a deletion map of the minimal $parB^+$ region. The numbering is in accordance with the coordinates of the $parB^+$ region shown in FIG. 1. The hok and sok genes within the region are indicated with filled-in and open areas, respectively. The presume sok promoter is indicated as ← and the putative hok Shine-Dalgarno sequence is shown as *. The plasmids pPR341 and pPR345 are pBR322 derivatives, which contain the parB region from +268 to +580 and +303 to +580, respectively. The plasmid pPR341 carries the hok Shine-Dalgarno sequence and the hok reading frame, whereas pPR345 only carries the hok reading frame. Both plasmids are devoid of the sok gene. Restriction enzyme sites are shown as $B_1$ (BamHI) and E (EcoRI).

Figure 16B:
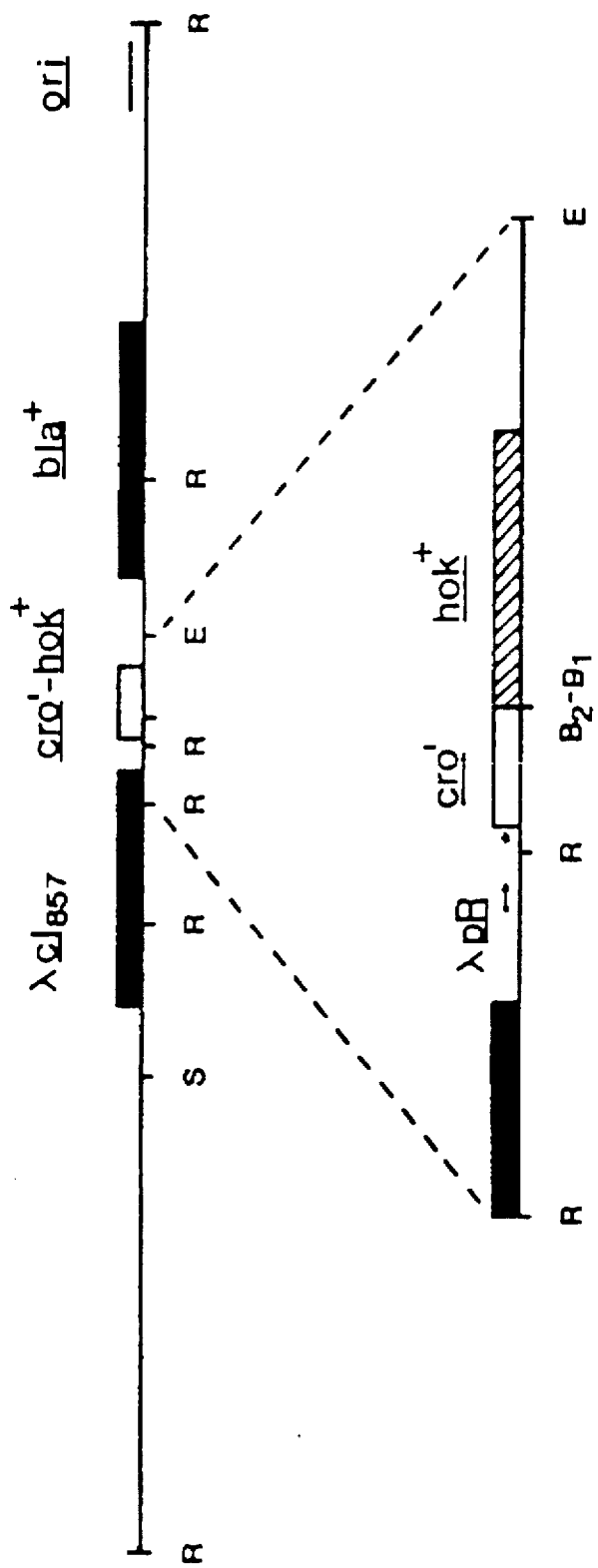

FIG. 16b shows the physical and genetic map of the plasmid pKG345 used for the induction of the cro⁻-hok gene fusion. Plasmid pKG345 is a pPR345 derivative in which a BglII-SalI fragment containing the λpR promoter and the cI857 allele of the λ repressor gene was inserted into pPR345 restricted with BamHI and SalI. This construction placed the transcription and translation of the hok gene under the control of the λpR promoter and cro Shine-Dalgarno sequence, respectively. The gene fusion is indicated as an open area for the cro⁻ gene and as a cross-hatched area for hok. The bla gene, the λ repressor (filled-in areas) and the origin of replication are also indicated. The λpR promoter is shown as ← and the cro Shine-Dalgarno sequence as *. Restriction enzyme sites are shown as R (RsaI), S (SalI), E (EcoRI), B (BamHI) and $B_2$ (BglII).

Figure 17:
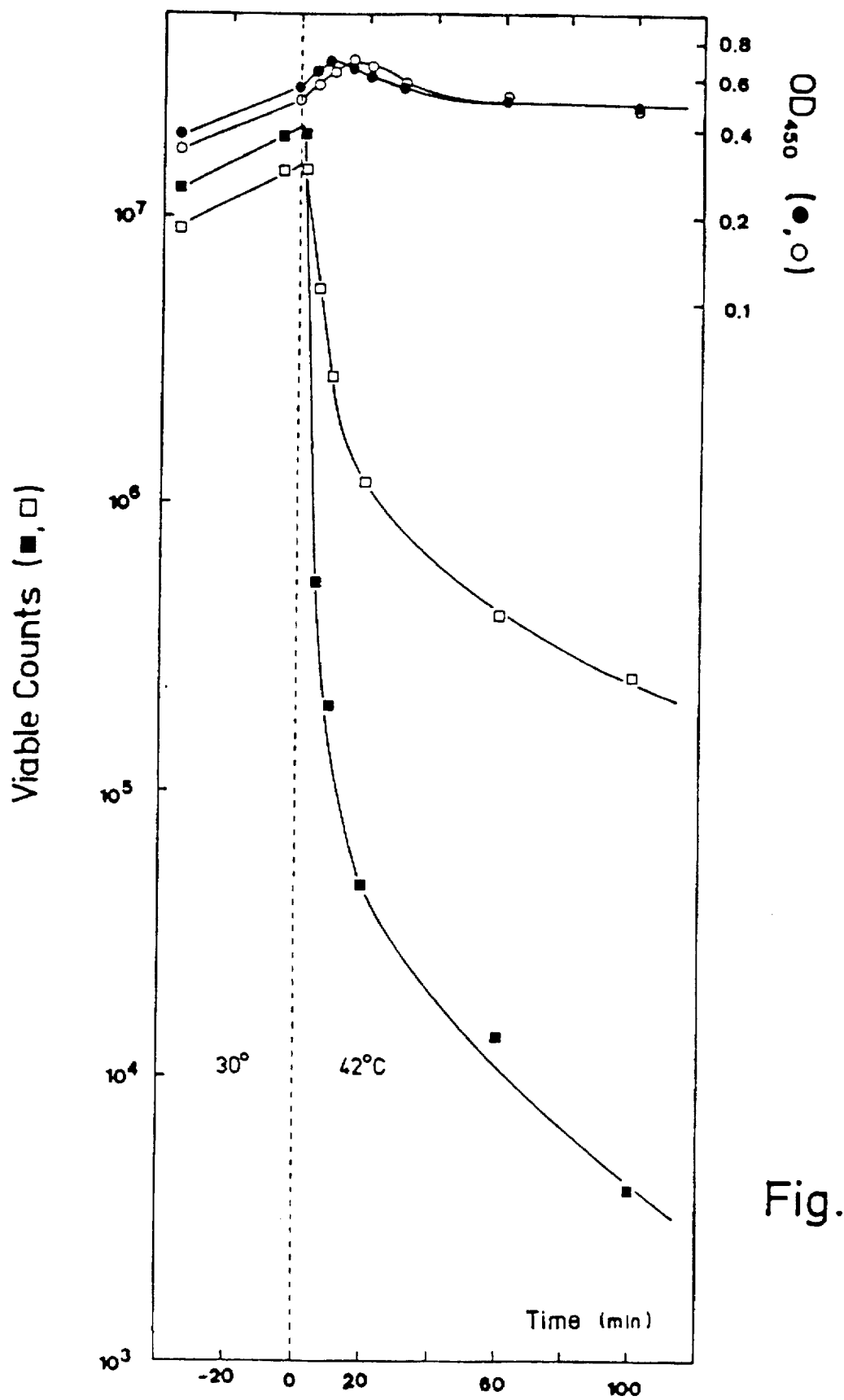

FIG. 17 shows host cell killing after λpR induced expression of the hok gene and the cro⁻-hok⁺ gene fusion. *E. coli* strain MC1000 was grown exponentially in A+B minimal medium supplemented with 0.2% glucose and 1% casamino acids at 30° C. containing either pKG341 (open symbols) or pKC345 (filled-in symbols). At time zero, the temperature was shifted to 42° C. and growth of the cultures was followed as $OD_{450}$ and viable counts on selective medium (LB plates containing 100 μg/ml ampicillin).

Figure 18:
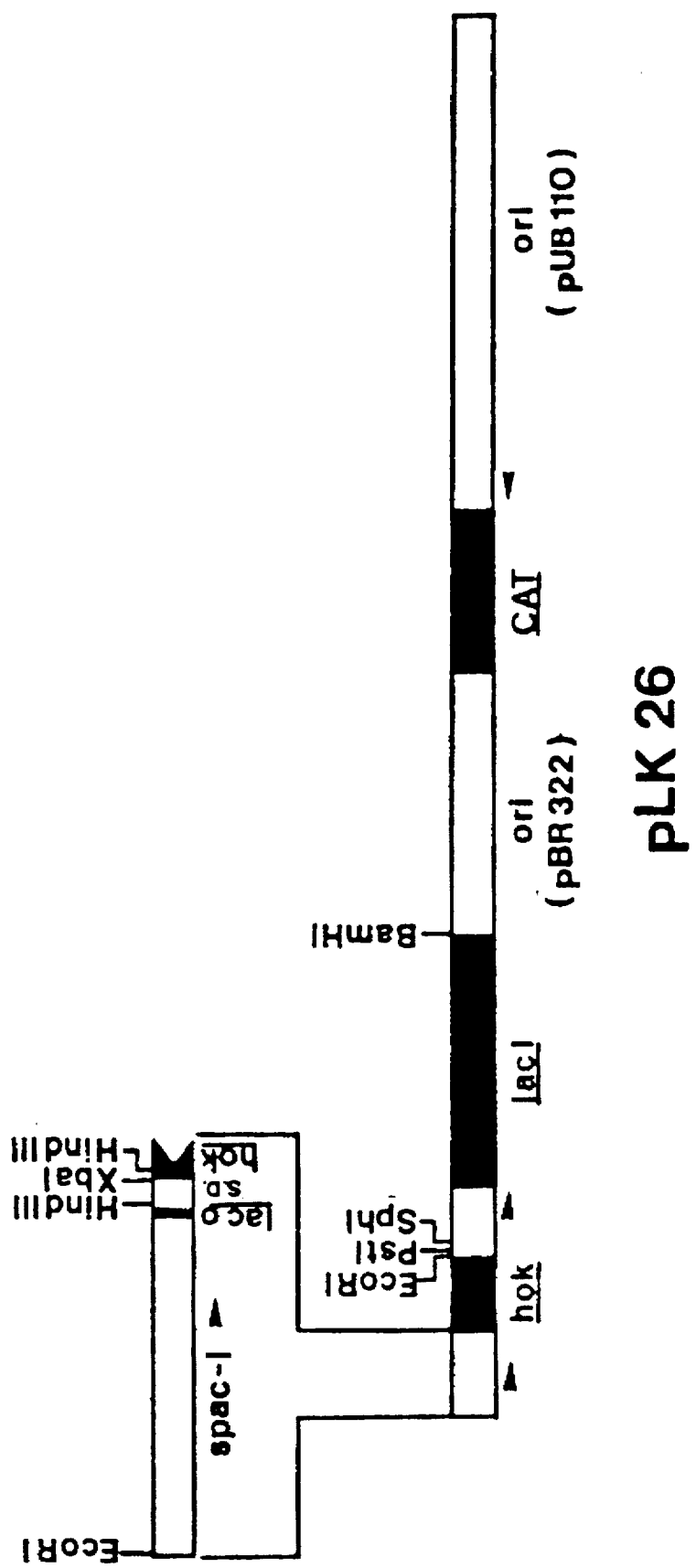

FIG. 18 is a map of plasmid pLK26. The filled-in areas denote structural genes; the insert shows the spacI promoter followed by a synthetic ribosomal binding site and a polylinker; ori denotes the origin of replication from pBR322 and pUB110, respectively; lac o denotes the lac operator.

Figure 19:
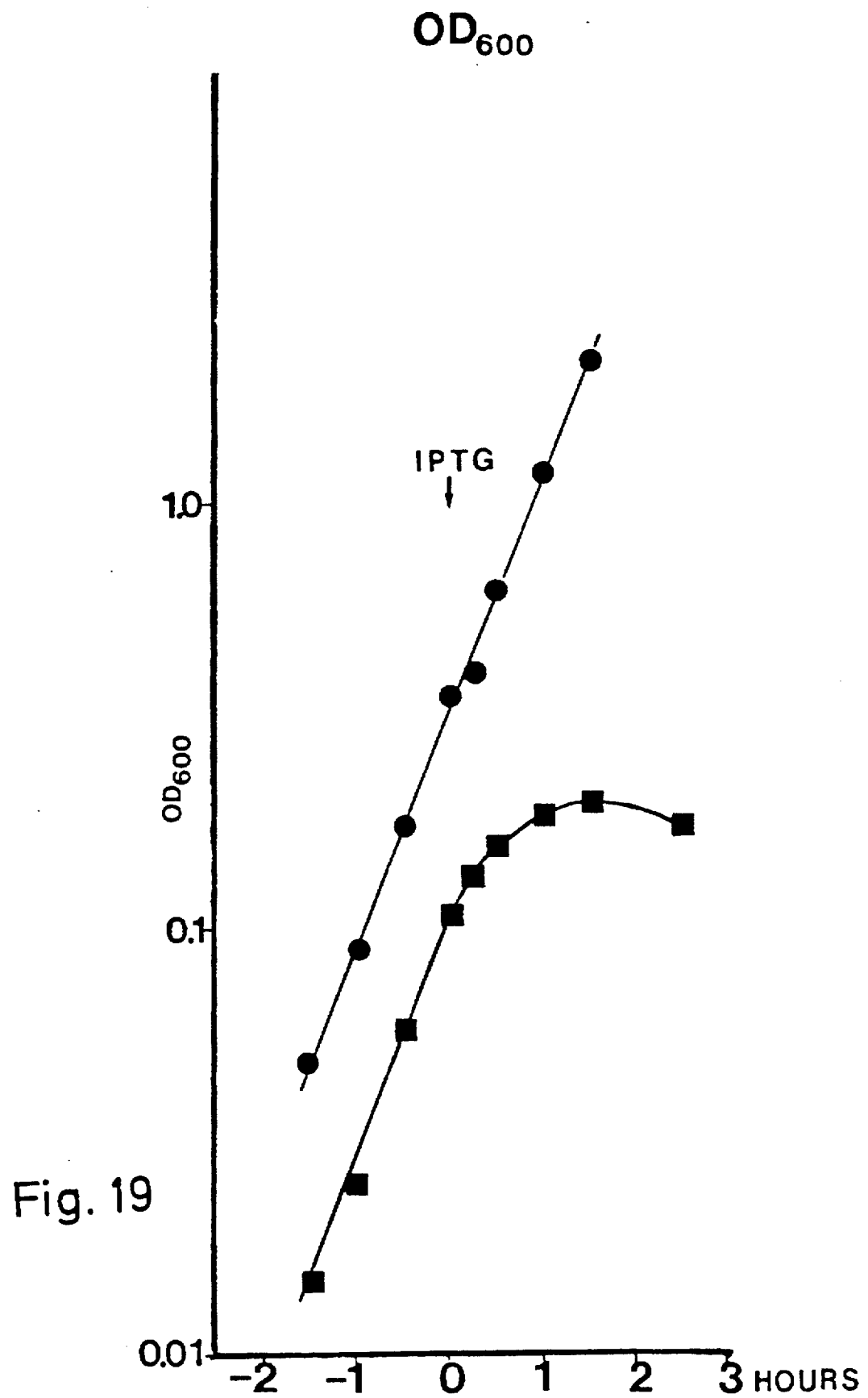

FIG. 19 is a graph showing viable counts ($OD_{600}$) of *B. subtilis* BD170 containing pSI-1 (circles) or pLK26 (squares), as a function of time. The cells were grown exponentially in LB medium with 5 μg/ml chloramphenicol at 37° C.

Figure 20:
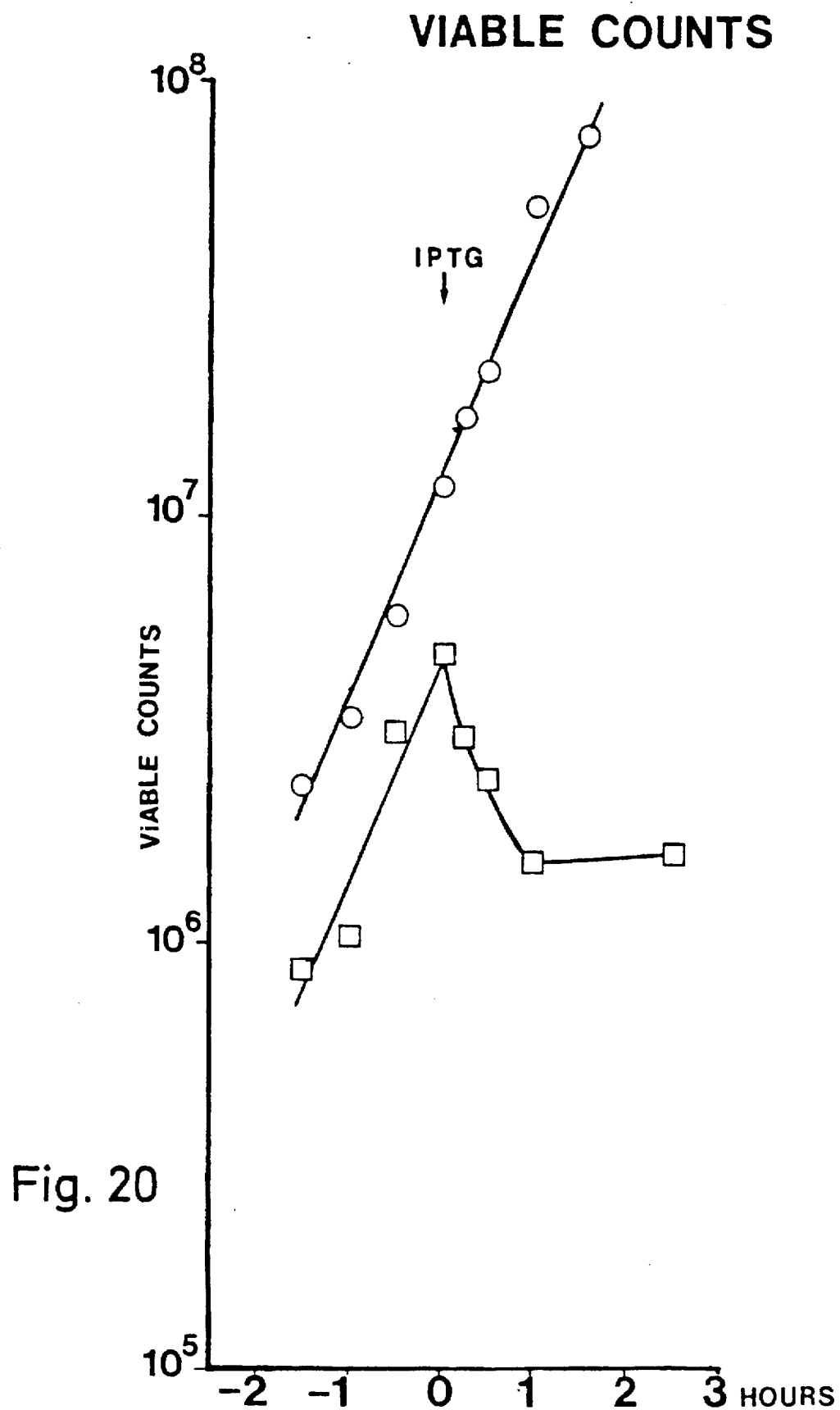

FIG. 20 is a graph showing the killing kinetics after induction of hok with 2 mM IPTG. *B. subtilis* BD170 containing pSI-1 (circles) or pLK26 (squares) were grown in LB medium with 5 μg/ml chloramphenicol. Viable counts were monitored on LB plates with 5 μg/ml chloramphenicol.

Figure 21:
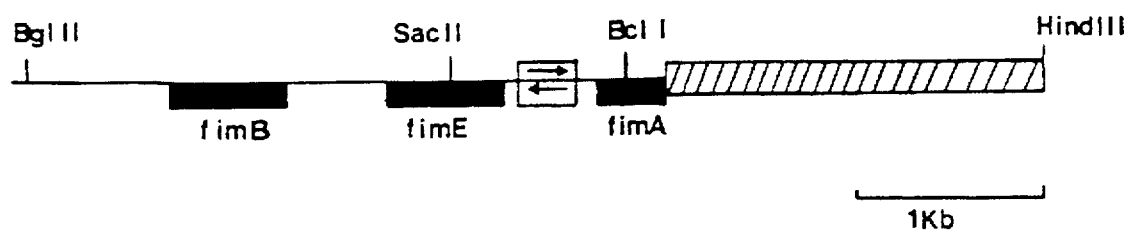

FIG. 21 shows a map of plasmid pPKL8 (5.5 kb). The position of the fimB, fimE and the truncated fimA gene is indicated. The box with double arrows denotes the invertible 300 bp region containing the promoter of the fimA gene. The hatched area indicates pBR322 DNA.

Figure 22:
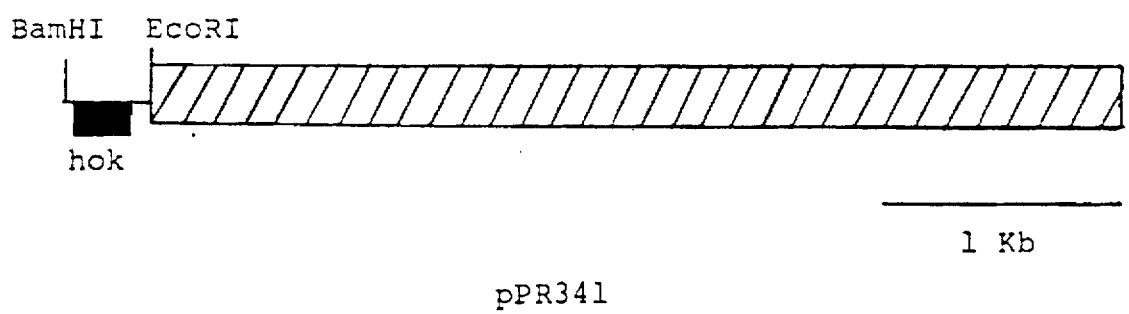

FIG. 22 shows a map of plasmid pPR341 (4.3 kb). The hatched area indicates pBR322 DNA.

Figure 23:
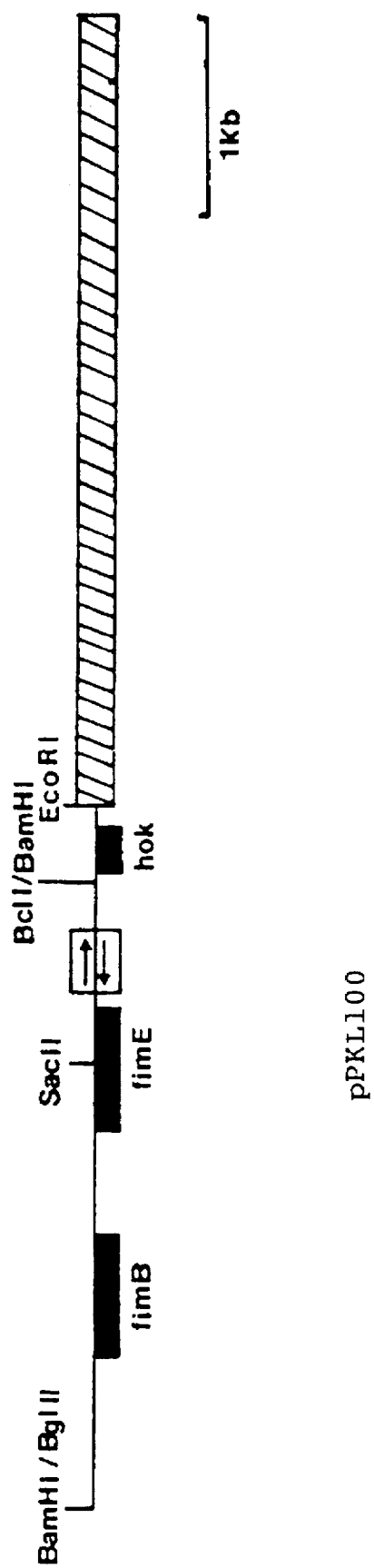

FIG. 23 shows a map of plasmid pPKL100 (7.5 kb). See FIGS. 14 and 15 for details.

Figure 24A:
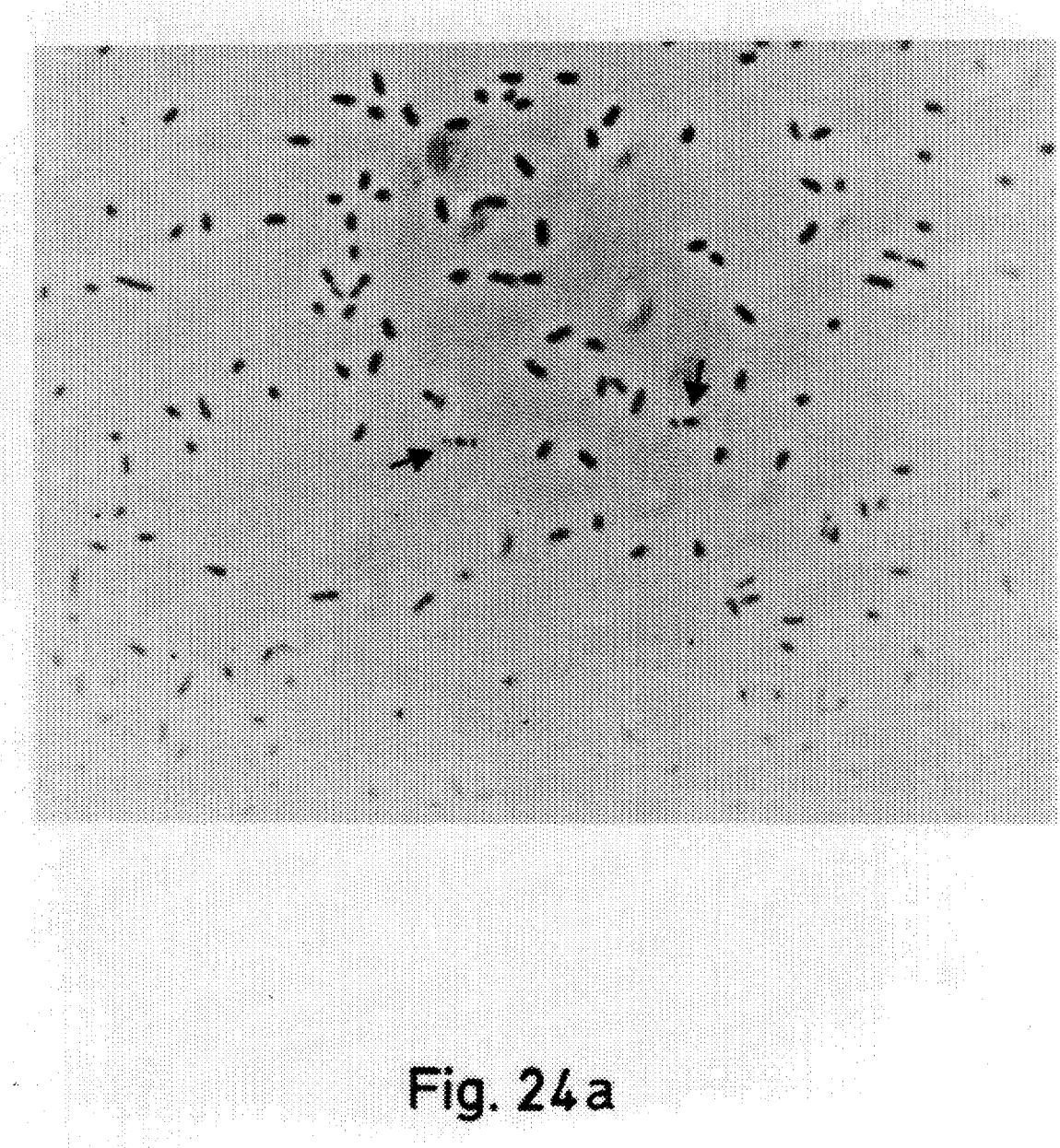
Figure 24B:
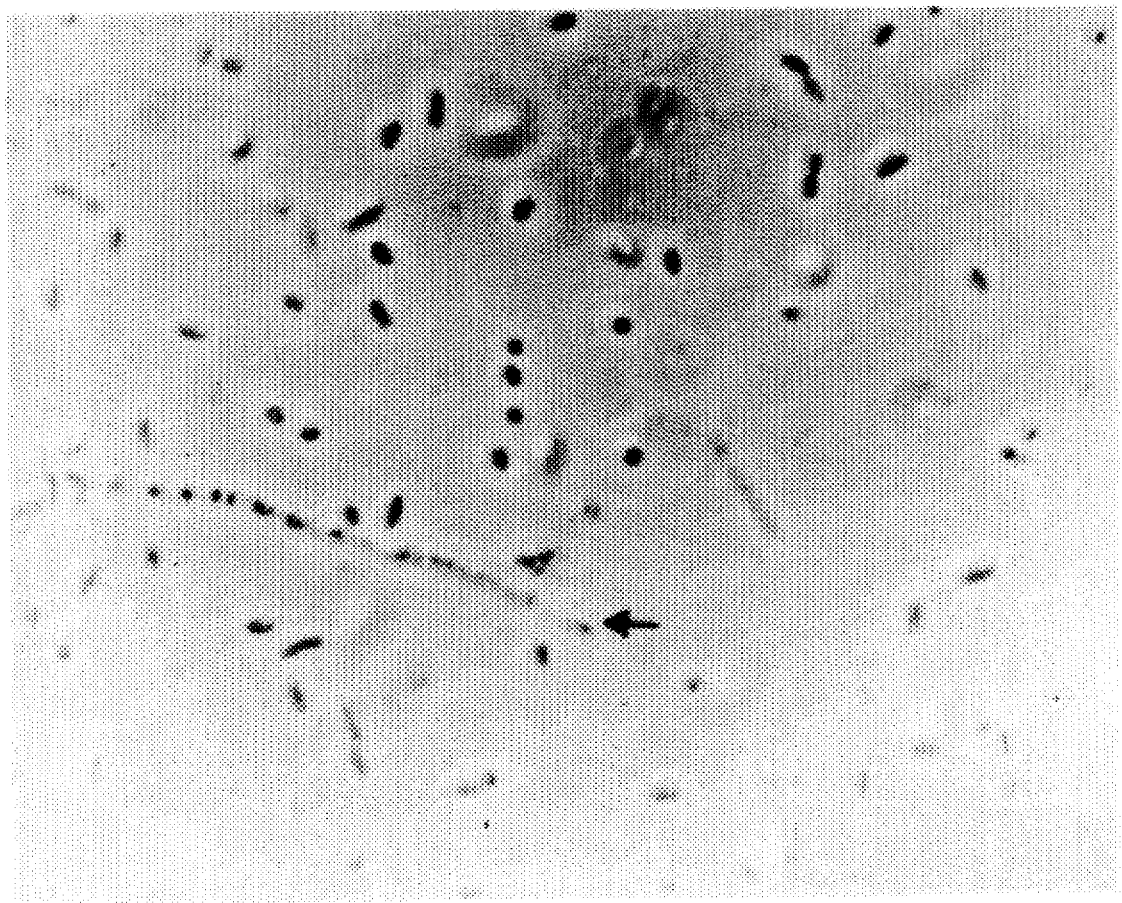

FIGS. 24a and 24b show microphotographs of *E. coli* K-12 strain MC1000 cells harbouring plasmid pPKL100. The arrows indicate killed ghost cells.

Figure 25:
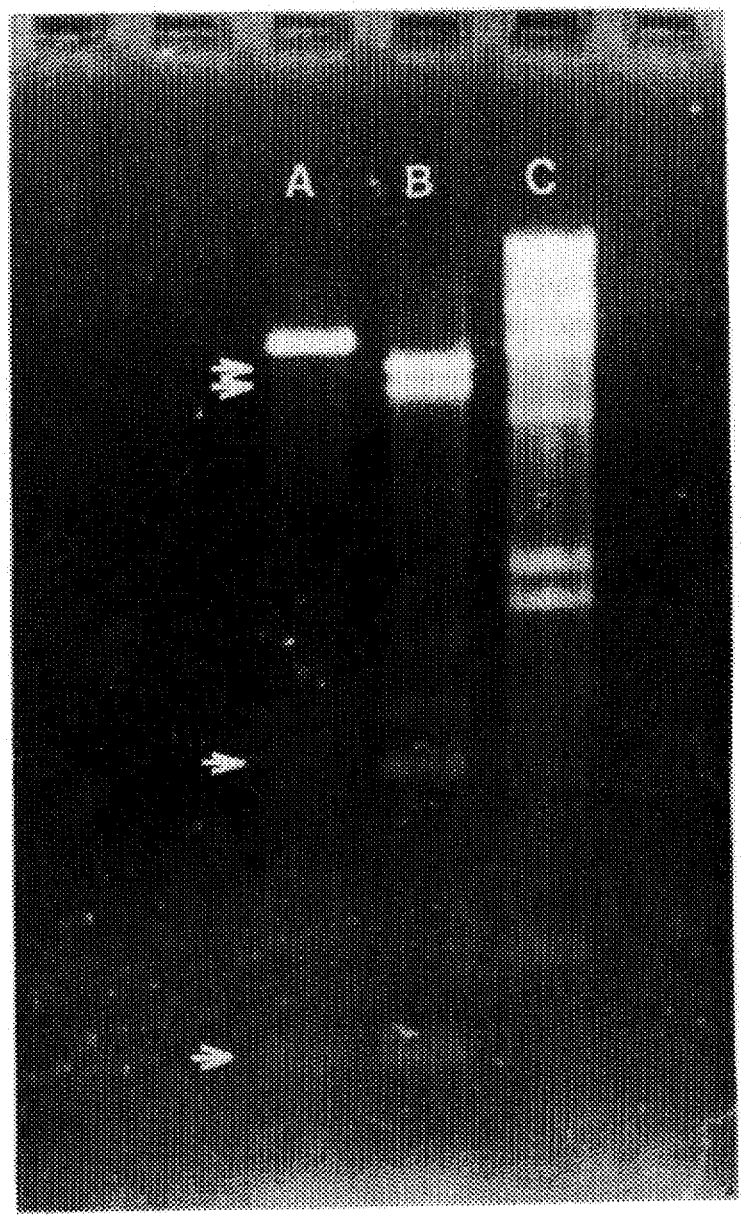

FIG. 25 shows digestions with SacII and SnaBI of plasmids pPKL100 (lane A) and pPKL8 (lane B). Lane C is a HindIII digest of bacteriophage lambda used as a molecular weight marker showing the following sizes: 23.1 kb, 9.4 kb, 6.6 kb, 4.4 kb, 2.3 kb, 2.0 kb and 0.56 kb. The arrows indicate fragments affected by the inversion of the 300 bp segment.

Figure 26A:
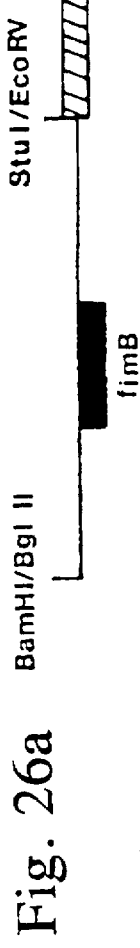
Figure 26B:
Figure 26C:
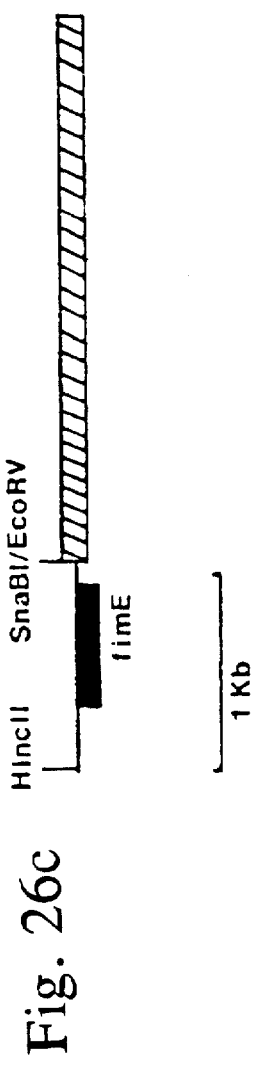

FIG. 26 shows maps of plasmids pLP4 (=A), pLP5 (=B) and pLP6 (=C). The hatched boxes represent pACYC184 DNA. Relevant restriction sites as well as the positions of the fimB and fimE genes are shown.

MATERIALS AND METHODS

Bacterial Strains and Plasmids

The bacteria and plasmids are listed in Table 1.

The experimental techniques used were standard techniques employed in the fields of microbial genetics (J. Miller: *Experiments in Molecular Genetics*, Cold Spring Harbor, N.Y., 1972) and genetic manipulation (Davis, Bothstein and Roth: *A Manual for Generic Engineering; Advanced Bacterial Generics*, Cold Spring Harbor, N.Y., 1980, and Maniatis, Fritsch and Sambrook: *Molecular Cloning*, Cold Spring Harbor, N.Y., 1982.

All cells were grown in LB medium (Bertani, *J. Bact* 62, 1951, p. 293) with 0.2% of glucose and 1 μg/ml of thiamin, or A+B minimal medium (Clark and Maaløe, *J. Mol. Biol.* 23, 1967, p. 99) supplemented with 0.2% of glucose and 1% casamino acids. The plates used were LA plates containing LB medium and 1.5% of agar.

Clear lysates were prepared according to the method described by Clewell and Helinski, *Proc. Natl. Acad. Sci. USA* 62, 1969, pp. 1159–66.

Small scale preparation of plasmid DNA was performed by the method of Birnboim et al., *Nucl. Acids Res.* 7, 1979, pp. 1513–23.

Large-scale preparation and analysis of plasmid DNA was performed using dye boyant density gradient centrifugation according to Stougaard and Molin, *Anal. Biochem.* 118, 1981, p. 181.

The restriction endonucleases were used in accordance with the prescriptions provided by the manufacturer (Boehringer, Mannheim or Biolabs, New England) at 37° C. Double and triple digests were performed by starting with the enzyme requiring the lowest salt concentration and then adjusting with additional buffer before adding the next enzyme.

Treatment with the exonuclease Bal31 was performed as follows: 0.1 unit of Bal31 was added to 50 μg linear DNA and samples were taken out at 1', 2', 4', 8', 16', 32' and 60' to 60 mM EDTA, extracted with phenol, ethanol precipitated and resuspended in 20 μl TE buffer. Half of the 20 μl was digested with the appropriate restriction enzyme subjected to agarose gel electrophoresis to determine the average size of the deleted DNA deletions. To the other half, the appropriate linker was added and the mixture ligated for 48 hours with an excess of T4 DNA ligase.

Figure 1:
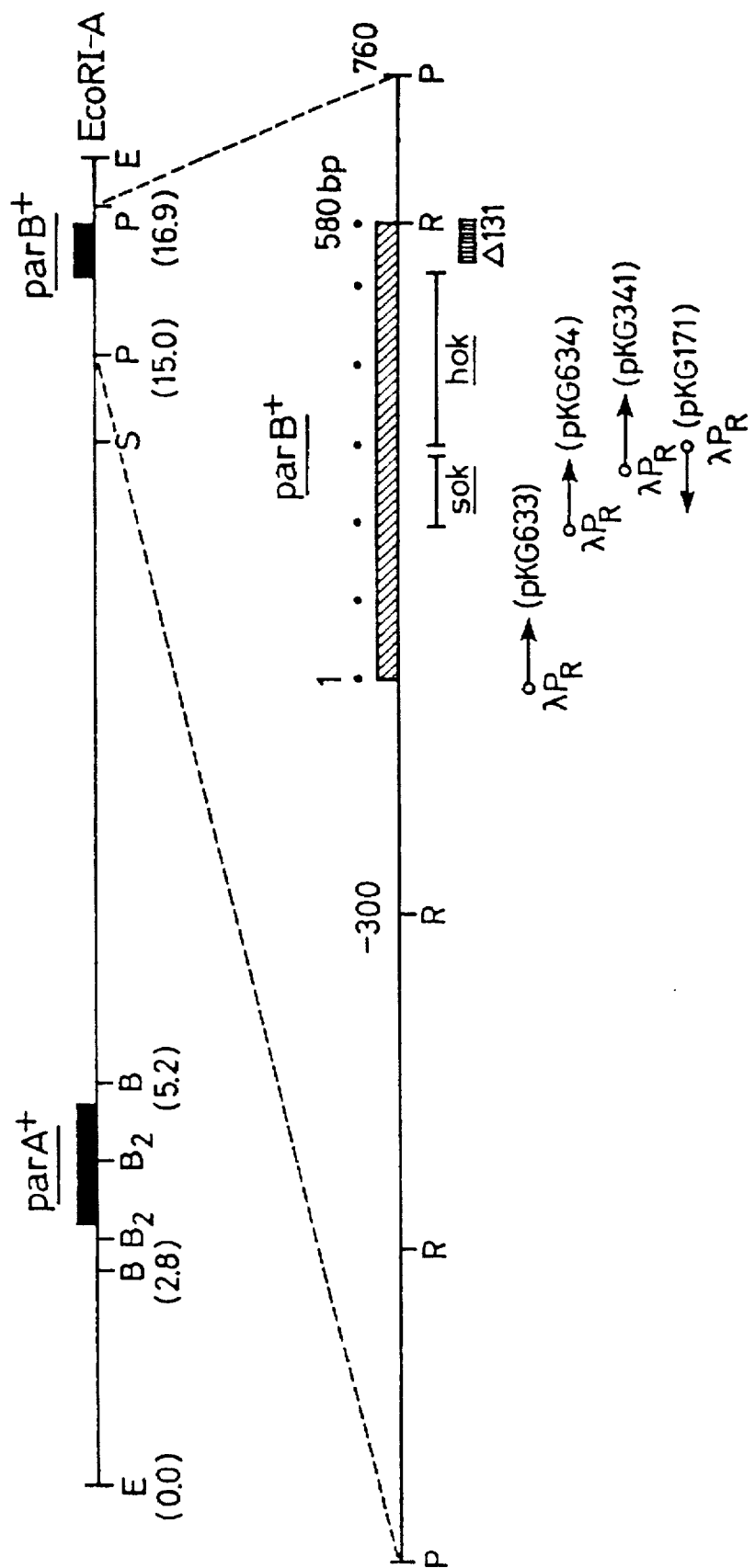
FIG. 1 shows a deletion mapping of the parB$^+$ region. The localization of the parA$^+$ region and the parB$^+$ region within the EcoRI-A fragment of plasmid R1 are shown as black boxes. Restriction enzyme sites in the EcoRI-A fragment are as described in International Patent Application No. PCT/DK83/00086, Publication No. WO 84/01172. The parB$^+$ region is located within the 1.9 kb PstI fragment bordered by coordinates 15.0 to 16.9. The parB$^+$ region was further mapped to the right-hand 580 bp of an 880 bp RsaI fragment. The cross-hatched region indicates the minimal parB$^+$ region. The position of the hok and sok genes within the 580 bp parB$^+$ region is also shown. A BglII-SalI fragment containing the λpR promoter and the cI857 allele of the λ repressor gene was inserted into pBR322 derivatives carrying various parts of the parB fragment. The position of the inserted fragments and the direction of transcription from λpR are shown below the map of the parB$^+$ region (arrows). The λpR promoters in pKG633, pKG634 and pKG341 read from left to right into the parB$^+$ region whereas the λpR promoter in pKG171 reads from right to left. Restriction enzyme sites are shown as E (EcoRI), B (BalI), B$_2$ (BglII), S (SalI), R (RsaI), and P (PstI).

Ligation of restricted plasmid DNA was performed as recommended by the manufacturer with the exception of blunt end ligation, where an excess of T4 DNA ligase and ATP was added.

pKG633: The SalI-BglII fragment of pOU82 containing the cI857 temperature sensitive allele of the λ repressor gene and the λpR promoter was inserted into pPR633 in front of the parB+ region so that the λpR promoter reads into the region from left to right (FIG. 1). In an analogous way, the SalI-BglII fragment of pOU82 was inserted into pPR634 and pPR341, which are Bal31 deletion derivatives of pPR633, resulting in pKG634 and pKG341. pKG171: In pPR171, the SalI-BglII fragment of pOU82 was inserted in the opposite orientation, resulting in pKG171. The positions and orientations of the inserted λpR promoters relative to the hok and sok genes are shown in FIG. 1. pF634: The EcoRI-SalI fragment of pKG634 containing the right 390 bp of the parB+ region and the λ cI857-pR inducible promoter system was inserted into the unique SalI site in the kanamycin resistance (aphA+) fragment of pML31 by blunt end ligation (S1 nuclease was used to make the restricted DNA fragments blunt-ended).

The DNA was cleaved with the appropriate restriction endonucleases according to the recommendations given by the manufacturers. For cellular DNA, 10 units per microgram of DNA was used. The incubation time was 3 hours at 37° C. The generated DNA fragments were separated by electrophoresis through 0.7% or 1% agarose gels in a Tris-acetate buffer at 0.8 volt per cm for 18 hours and visualized by ethidium bromide staining.

Mobilization of Plasmids

*E. coli* S 17.1 is capable of mobilizing plasmids like RSF1010 due to an inserted conjugative plasmid (RP1 derivative) in the chromosome. The plasmids in question were transformed to S 17.1 which then represented the donors.

One drop of donor cells and recipient cells were mixed on an LB plate (no selection) and incubated overnight. From the resulting cell mass, a liquid suspension was made from which dilutions were spread on double-selection plates.

TABLE 1

| Bacteria and plasmids | |
|---|---|
| Bacterium | Relevant phenotype |
| *E. coli* K-12, MC1000[1] | Leu−, Lac−, Str$^R$ |
| *E. coli* K-12, S 17.1[2] | Pro−, Str$^R$, Mob+ |
| *E. coli* K-12, 1005[3] | Met−, Nal$^R$ |
| *Serratia marcescens* | Tc$^R$ |
| *Pseudomonas putida* | Rif$^R$ |
| *Bacillus subtilis* BD170[4] | trpC2, thr-5 |

| Plasmid | Relevant phenotype | Coordinates of parB insert (cf. FIG. 1) |
|---|---|---|
| R1drd-19 | | |
| pSGS8[5] | pBR322−, Trp+, Ap$^R$ | |
| pBOE93 | RSF1010, Kan$^R$ | |
| pPR95 | R1, + (hok+, sok+) | −300→+580 |
| pPR311 | R1, + (hok+, sok+) | +1→+580 |
| pPR633 | pBR322, + (hok+, sok+) | +1→+580 |
| pPR634 | pBR322, − (hok+) | +194→+580 |
| pPR341 | pBR322, − (hok+) | +268→+580 |
| pPR171 | pBR322, − | −300→+288 |
| pPR154 | pBR322, − (sok+) | −300→+330 |
| pKG634 | pBR322, − (hok+) | +194→+580 |
| pKG341 | pBR322, − (hok+) | +268→+580 |
| pKG171 | pBR322, | −300→+288 |
| pPKL100 | pBR322, Ap$^R$, Tet$^r$ | +268→+580 |
| pPKL8 | pBR322, Ap$^R$ | |
| pJK3-1[6] | pBC16, pBR322, Tet | |
| pSI-1[7] | pUB110, pBR322, Cat | |

[1] M. J. Casabadan, S. N. Cohen, *J. Molec. Biol.* 138, 1980, p. 179.
[2] R. Simon, *Biotechnology*, November 1983.
[3] J. Grinsted, J. R. Saunders, L. C. Ingram, R. B. Sykes, M. N. Richmond, *J. Bacteriol.* 110, 1972, p. 529.
[4] Dubnan & Cirigliano, *J. Bacteriol.* 117, 1974, p. 488
[5] G. Skogman, J. Nilsson, P. Gustafsson, *Gene* 23, 1983, p. 105.
[6] Kreft et al., in Molecular Cloning and Gene Regulation in Bacilli, eds. A. T. Ganesan et al., Academic Press, 1982, p. 145.
[7] A slight modification of pAIQ25 described in Yansura and Henner, *Proc. Natl. Acad. Sci.* 81, 1984, p. 439; obtained from Henner.

Purification of Chromosomal DNA

Total DNA was extracted from bacteria as follows. Cells were harvested by centrifugation, washed twice in 1×TEN buffer (TEN=10 mM TRIS (pH 7.5), 1 mM EDTA, 0.1M NaCl) and resuspended in ⅒th volume of TEN containing 1 mg/ml lysozyme. Following incubation at 37° C. for 30 minutes, the protoplasts were lysed by addition of sodium dodecyl sulphate to a final concentration of 1%, and proteinase K was added to 0.25 mg/ml. The lysate was incubated at 37° C. for 2 hours and subsequently extracted twice with buffered phenol and three times with chloroform. Sodium acetate was added to 0.3M and the DNA was precipitated by addition of 1 volume isopropanol. The precipitate was washed several times in 96% and 80% ethanol. Finally, the DNA was dissolved in 1 mM TRIS, 1 mM EDTA.

Total DNA from *Tetrahymena thermophila* BVII was prepared according to Nielsen, M. and Engberg, J.: *Biochim.*

Biophys. Acta 825, 1985, pp. 30–38.Macronuclei from *Tetrahymena thermophila* BVII were isolated (Cech, T. R. et al.: Cell 27, 1981, pp. 487–496) and DNA extracted (Maniatis et al., 1982, op.cit., pp. 280–281). rDNA from *Tetrahymena thermophila* BVII was prepared as described by Engberg, J. et al.: *J. Mol. Biol.* 104, 1976, pp. 455–470.

Chloroplast DNA from *Pisum sativum* was isolated according to Bookjans, G. et al.: *Analyt. Biochem.* 141, 1984, pp. 244–247.

Embryonic liver tissue from a 7-weeks legal abortion was minced in physiological saline and the DNA was prepared according to Maniatis et al., 1982, op.cit., pp. 280–281. In a similar manner, DNA was isolated from a tumor biopsy from a case of neuroblastoma; the isolated DNA was found to contain a several hundred-fold amplified chromosomal region and, correspondingly, the tumor cells were found to contain numerous extrachromosomal mini-chromosomes by microscopy of mitotic cells.

Isolation of DNA Fragments for Radioactive Labelling 100 micrograms of pPR95 and pBD2724 DNA were digested with EcoRI and EcoRI and HindIII, respectively. The fragments were separated by electrophoresis through a 1% agarose gel in Tris-borate buffer at 5 volts per cm for 3 hours. The desired fragments were isolated by electroelution onto an NA45 membrane (Schleicher & Schüll) according to the manufacturer's recommendations. Following recovery of the fragments by elution of the filter in 1.5M NaCl at 65° C., the fragments were again subjected to purification by agarose gel electrophoresis and NA45 membrane recovery from the gel.

Agarose Gel Electrophoresis

The DNA was cleaved with the appropriate restriction endonucleases according to the recommendations given by the manufacturers. For cellular DNA, 10 units per microgram of DNA was used. The incubation time was 3 hours at 37° C. The generated DNA fragments were separated by electrophoresis through 0.7% or 1% agarose gels in a Tris-acetate buffer at 0.8 volt per cm for 18 hours and visualized by ethidium bromide staining.

A molecular weight marker was prepared as follows: wt λ DNA was restricted with HindIII and end-labelled by means of the Klenow polymerase from Boehringer, Mannheim, as recommended by the manufacturer, in the presence of α-32P-dCTP plus non-radioactive dATP and dGTP. When used as a molecular weight marker, an amount of Tetrahymena macronuclear DNA was added corresponding to the DNA load of the test lanes.

Transfer of DNA Fragments from Gel to Nitrocellulose Filter

Following partial depurination in 0.25N HCl for 15 minutes at room temperature, denaturation of DNA in the gel, neutralization and subsequent transfer of DNA from gel to a BA85 (Schleicher & Schüll) nitrocellulose filter was carried out as described in Maniatis et al., 1982, op.cit., pp. 280–281. Completeness of transfer was assured by ethidium bromide staining of the gel after transfer.

Preparation of Radioactively Labelled Probe 0.3 microgram of the 900 bp parB fragment and 0.3 microgram of the 300 bp relB-orf3 fragment were radioactively labelled by nick-translation (Maniatis et al., 1982, op.cit.) using 0.25 micromolar α-32P-deoxycytidine triphosphate (3000 Ci per mmol). The unincorporated radioactive precursor was removed by means of repeated ethanol precipitations. To each preparation were added 100 micrograms of *E. coli* tRNA as carrier.

The specific activities of the probes were $2-3 \times 10^8$ and $4-5 \times 10^7$ dpm per microgram of parB and relB-orf3 fragment, respectively.

Hybridization

Filters containing DNA transferred from agarose gels were preincubated in plastic bags with the hybridization solution (10 ml per 120 cm$^2$) for 18 hours at 37° C. with constant shaking. The hybridization solution was modified from Wahl et al., *Proc. Natl. Acad. Sci.* 76, 1979, pp. 3683–3687 and contained 38% deionized formamide, 0.75M NaCl, 50 mM sodium phosphate and 10×Denhardt's solution (50×Denhardt's solution is 0.2% bovine serum albumin, 0.2% polyvinylpyrrolidone and 0.2% Ficoll).

Following preincubation, the denatured radioactively labelled probes were added to appropriate filters. In experiments employing the parB probe, the concentration of fragment during hybridization was 3 ng/ml while the relB-orf3 probe was used at a concentration of 1.3 ng/ml to obtain equimolar concentrations of complementary sequences in the two situations.

Hybridization was carried out at 37° C. with gentle shaking for 19 hours.

The hybridized filters were washed once for 20 minutes at room temperature in 0.4× washing buffer, and finally twice for 30 minutes at 60° C. in 4× washing buffer. The washing buffer contained 0.6M NaCl, 0.1% SDS, 0.1% sodium pyrophosphate, 50 mM sodium phosphate, pH 6.5. Autoradiography was performed using X-ray films and intensifying screens. Exposure times are indicated in the description of the figures.

The term "filter hybridization analysis" is used in the Examples to denote the following sequence of operations: agarose gel electrophoresis of DNA fragments, transfer of the fragments to nitrocellulose filters, hybridization with the appropriate radioactively labelled probe, filter washing, and autoradiography of the filter following washing. The data shown in the Examples represent autoradiograms obtained by filter hybridization analysis.

The term homology is used here to denote the presence of any degree of complementarity between a given probe and the nucleic acid species being analyzed.

The degree of homology is expressed as the fraction of complementary bases in a duplex nucleic acid molecule formed between a given probe and the nucleic acid species being analyzed.

The minimum degree of homology which is detectable is a function of the experimental conditions exployed during hybridization and of characteristics of the probe and the nucleic acid species being analyzed.

The degree of homology between the probe DNA and a filter-bound DNA species was estimated from the intensity of the actual hybridization signal compared to the signal intensity observed for a 100% homologous filter-bound sequence under the same conditions.

The intensity of the hybridization signal depends primarily on the rate of hybridization and the number of filter-bound DNA molecules present in the specifically hybridizing band. The rate of hybridization is mainly determined by the concentration of complementary sequences during hybridization, the ionic conditions, the temperature and the degree of homology between the probe DNA and the filter-bound molecules. The rate of hybridization decreases by the presence of non-complementary sequences (Bonner, T. I. et al., *J. Mol. Biol.* 81, 1973, p. 123) which decreases the thermal stability of the duplex DNA; 1% mismatch between probe and filter-bound DNA results in a decrease in thermal stability of 1 degree (Maniatis et al., 1982, op.cit., p. 388). The hybridization conditions therefore determine which level of mismatch will still yield a detectable signal. It should be noted that the conditions employed in the present work did not lead to saturation of the filter-bound DNA with probe.

The present set of conditions for hybridization and filter subjects DNA duplexes to a temperature which is 40° C. below the mean melting temperature of perfectly matched duplex DNA in the same ionic environment, i.e. the conditions allow the detection of signals from duplexes containing a high degree of non-pairing bases. The formula used in these calculations is discussed in Beltz, G. A. et al., *Meth. Enzymol.* 100, 1983, pp. 266–285.

It is estimated that the conditions employed detect 100% of the maximum hybridization signal obtained from duplexes with from 100% down to 80% homology while the signal from a 60% homologous duplex is 50% of the above maximum intensity, cf. above. Duplexes with lower homology than 60% will yield still weaker signals.

For duplexes with extensive mismatch, a signal may be detectable if the exposure time of the autoradiogram can be prolonged or if the number of copies of filter-bound complementary molecules can be increased.

EXAMPLE 1

Deletion Mapping of the parB Region (cf. FIG. 1)

Figure 2:
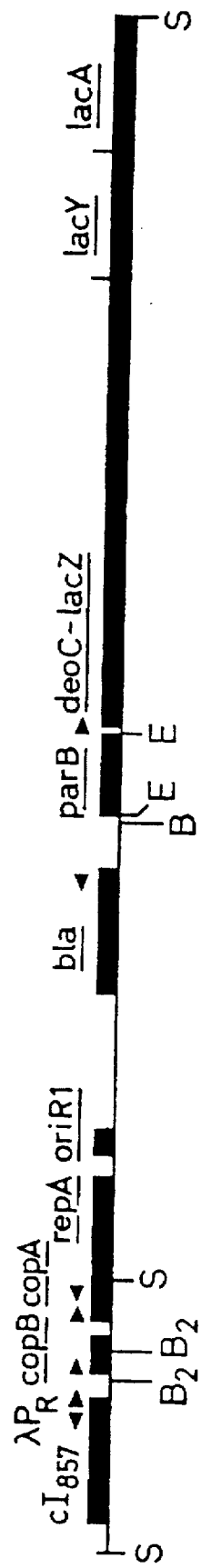
FIG. 2 shows a map of plasmid pPR95 (13 kb). copA, copB represents replication control genes of plasmid R1; repA represents a gene required for R1 replication; ori is the origin of replication; bla denotes a gene conferring ampicillin resistance on plasmid-carrying cells; parB represents the R1 derived maintenance function encoding the hok and sok genes; deo-lacZ$^-$ denotes a translational fusion between the deoC gene and the lacZ gene. lacZ,Y,A represent the lac operon; cI857 represents a gene which codes for a temperature sensitive λ repressor controlling λpR promoter activity. Arrows denote direction of transcription. The black bars denote the extension of the various genes. Restriction enzyme sites are shown as SalI (S), BglII (B$_2$), BamHI (B) and EcoRI (E).

Construction of pPR95 (FIG. 2)

The construction of pPR95 was done in the following way: plasmid pOU93 (Gerdes et al., *J. Bacteriol.* 161, 1985, pp. 292–98) is a pBR322 derivative containing the parB PstI fragment derived from the EcoRI-A fragment of plasmid R1 (FIG. 1). The PstI fragment is conveniently divided into smaller fragments by the restriction enzyme RsaI as shown in FIG. 1. By conventional cloning procedures, the largest RsaI fragment (880 bp) was inserted into the SmaI site of the pBR322 derived cloning vector pHP34 (Prentki et al., *Gene* 17, 1982, pp. 189–96), resulting in pPR13. The SmaI site of pHP34 is flanked by two EcoRI sites and therefore the inserted 880 bp RsaI fragment was converted to a 900 bp EcoRI fragment. The so generated 900 bp EcoRI fragment of pPR13 was cloned into the unique EcoRI site of the miniR1 derivative pOU82 (International Patent Application No. PCT/DK83/00086, Publication No. WO 84/01172), resulting in pPR95. A drawing of pPR95 is presented in FIG. 2.

Plasmid pOU82 is unstably inherited due to the lack of any partitioning function (International Patent Application No. PCT/DK83/00086, Publication No. WO 84/01172), and has a loss frequency on the order of $10^{-2}$ per cell per generation.

On the other hand, pPR95 is very rarely lost and is characterized by having a loss frequency of less than $10^{-4}$ per cell per generation (measured as described in International Patent Application No. PCT/DK83/00086, Publication No. WO 84/01172), which is the characteristic loss frequency of parB$^+$ miniR1 derivatives. Thus, it may be concluded that the complete parB region is located on the 880 bp RsaI fragment as judged by the ability of the fragment to stabilize miniR1 replicons.

The fine mapping of the parB region was carried out as follows: pPR95 was restricted with BamHI, treated with exonuclease Bal31, and ligated. Before ligation, BamHI oligonucleotide linkers were added. This treatment resulted in a series of deletion derivatives covering the left-hand part of the parB region. The extension of the deletions was determined by size fractionation of DNA fragments on agarose gels after the DNA had been treated with the restriction enzymes EcoRI and BamHI. Subsequently, the precise insertion of the BamHI oligonucleotide linkers was determined by nucleotide sequencing as described by Maxam and Gilbert (*Meth. Enzymol.* 65, 1980, pp. 499–566). In this way, a very detailed mapping of the region was obtained. Furthermore, the ParB phenotype (determined as described in Materials and Methods) for each plasmid derivative was analyzed. Deletion from pPR95 of the sequence extending from –320 to 0 (cf. FIG. 1) resulting in pPR311 did not change the ParB$^+$ phenotype. Thus, the remaining 580 bp BamHI-EcoRI fragment in pPR311 must contain the complete parB region. Deletion from left further into the region completely abolishes the stabilizing activity.

Deletions into the right part of the 580 bp parB$^+$ fragment of pPR311 (cf. FIG. 1) resulted in loss of ParB$^+$ phenotype, so the parB region extends to a position close to this end of the fragment.

EXAMPLE 2

Figure 3A:
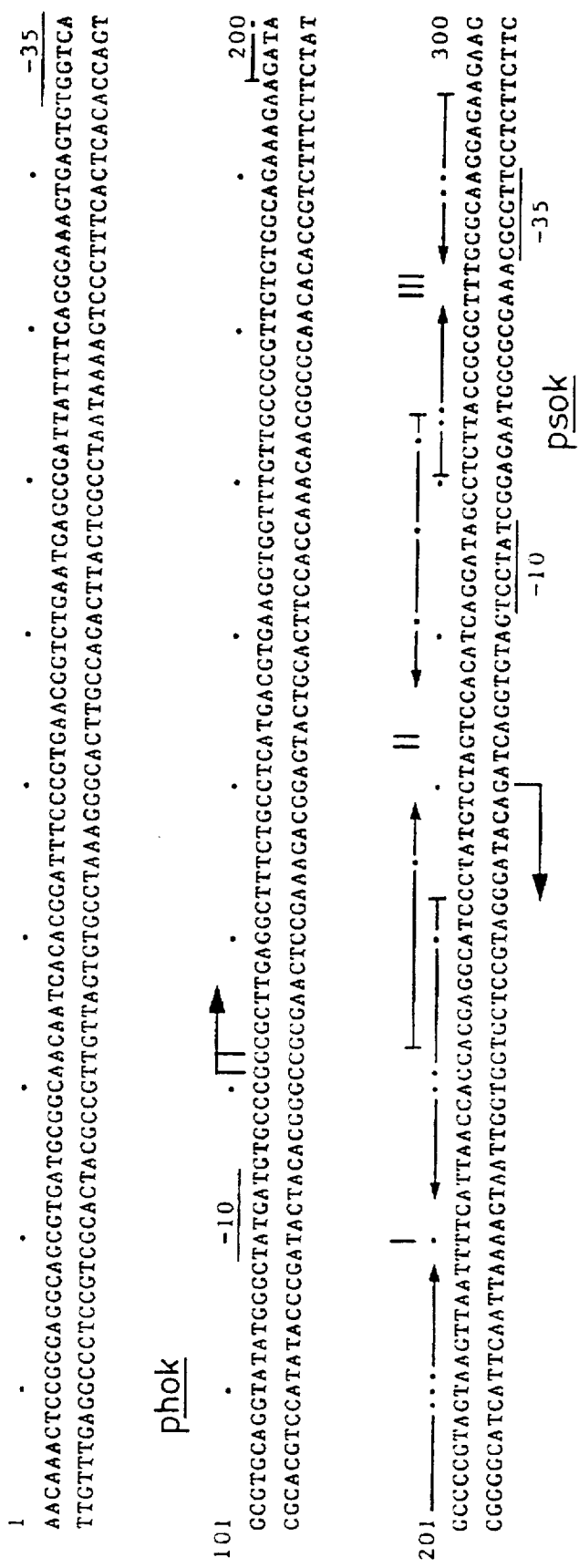

Nucleotide Sequence of the parB Region (cf. FIG. 3)

The nucleotide sequence of the minimal parB region, which is presented in FIG. 3, was obtained using the chemical degradation method as described by Maxam and Gilbert (*Meth. Enzymol.* 65, 1980, pp. 499–566). In the following, a detailed description of the essential biological information in the nucleotide sequence of the parB region is presented.

The sequence of the minimal parB region of 580 bp as defined in Example 1 (cf. FIG. 1) is depicted in FIG. 3. The central and left-hand parts of the region are very rich in dyad symmetries. The 580 bp contains three open reading frames consisting of more than 50 codons. The start and stop codons of these reading frames are indicated in FIG. 3. The reading frame starting at position +304 and ending at +460 is preceded by a DNA sequence (5'-AGGA-3') resembling the *E. coli* ribosome binding site (Shine and Dalgarno, *Nature* (*London*) 254, 1975, pp. 34–38), which is known to act as recognition site for ribosomes initiating translation of mRNA. The polypeptide product of this reading frame is shown below the DNA sequence in FIG. 3.

EXAMPLE 3

Figure 4:
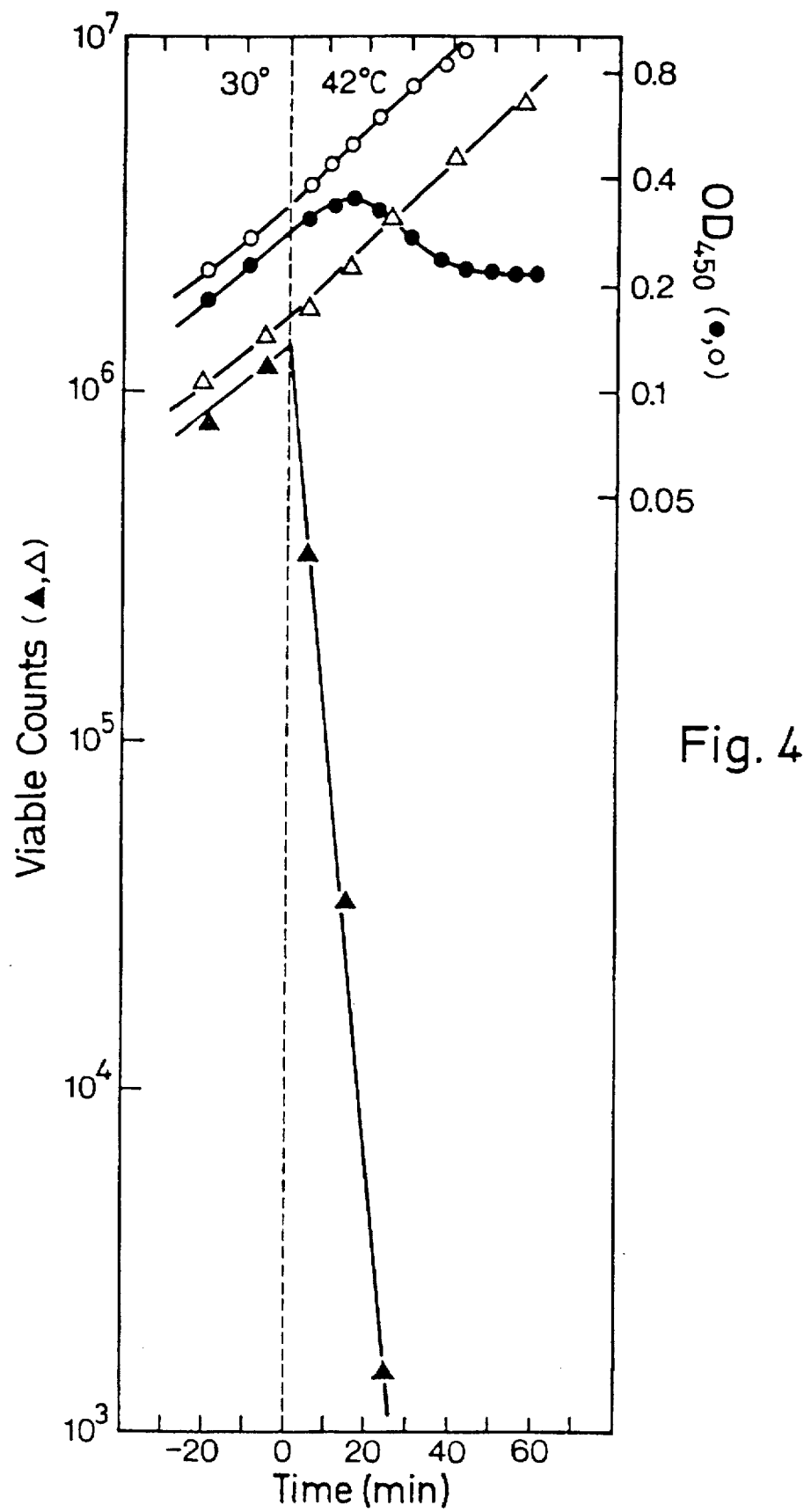
FIG. 4. shows host cell killing after λpR induced activation of the hok gene. Strain JC411 containing either pKG634 (closed symbols) or pKG171 (open symbols) was grown exponentially in A+B minimal medium supplemented with casamino acids at 30° C. At time zero, the temperature was shifted to 42° C. and growth of the cultures was followed as OD$_{450}$ and viable counts on selective medium (LB plates containing 50 µg/ml ampicillin).
Figure 5:
FIG. 5 is a photograph of cells sampled 1 hour after shift of strain JC411 (pKG634) to 42° C. Arrows point at cells with clearly changed morphology. Cells with a normal morphology are also seen. Magnification ×2000.

Functions Expressed from the parB Region (cf. FIGS. 4 and 5)

A series of plasmids was constructed from which conditional expression of the putative genes (as indicated from the sequence) in the parB$^+$ region was obtained through insertion of a fragment carrying the λpR promoter and the λcI857 gene. The positions of these insertions are indicated in FIG. 1. The λpR temperature inducible promoter system was chosen because the regulator gene for the λpR promoter (the cI857 gene) as well as λpR are located on a single BglII-SalI restriction fragment; furthermore, the cI857 allele of the λ repressor gene makes the inserted promoter inducible at high temperature (42° C.), but silent or near silent at low temperature (30° C.). The BglII-SalI fragment of pOU82 was inserted into plasmids pPR634 and pPR341 by conventional cloning procedures yielding plasmids pKG634 and pKG341, respectively (cf. Materials and Methods).

At 30° C., cells harbouring pKG634 and pKG341 grow normally; however, induction of λpR (at 42° C.) results in rapid killing of the host cells.

FIG. 4 shows the killing kinetics (viable counts) and growth measured as OD450 after a shift to 42° C. of strain JC411(pKG634). Viable counts decrease rapidly (half life of 2.5 minutes) and the increase of OD450 stops. The presence of a λpR promoter transcribing the parB region in the opposite direction (pKG171) has no effect on cell growth and viability (FIG. 4, control).

Microscopic examination (phase contrast) of the cells (JC411/pKG634) after heat induction of the λPR promoter showed that the cells changed morphology: Most of the material apparently condensed in zones, leaving the rest of the cell transparent. An illustration of this is shown in FIG. 5, in which both normal and changed cells are present. The cells having the characteristic parB induced appearance are termed "ghost" cells in the following.

Since the λpR-promoter fragment was inserted immediately upstream of the start of a 52 amino acids open reading frame (cf. Example 2), this strongly suggests that the 52 amino acids polypeptide encoded by the open reading frame starting at position +304 (FIG. 3) is responsible for the cell killing, and consequently, this gene is termed hok (host killing) in the following.

EXAMPLE 4

Figure 6:
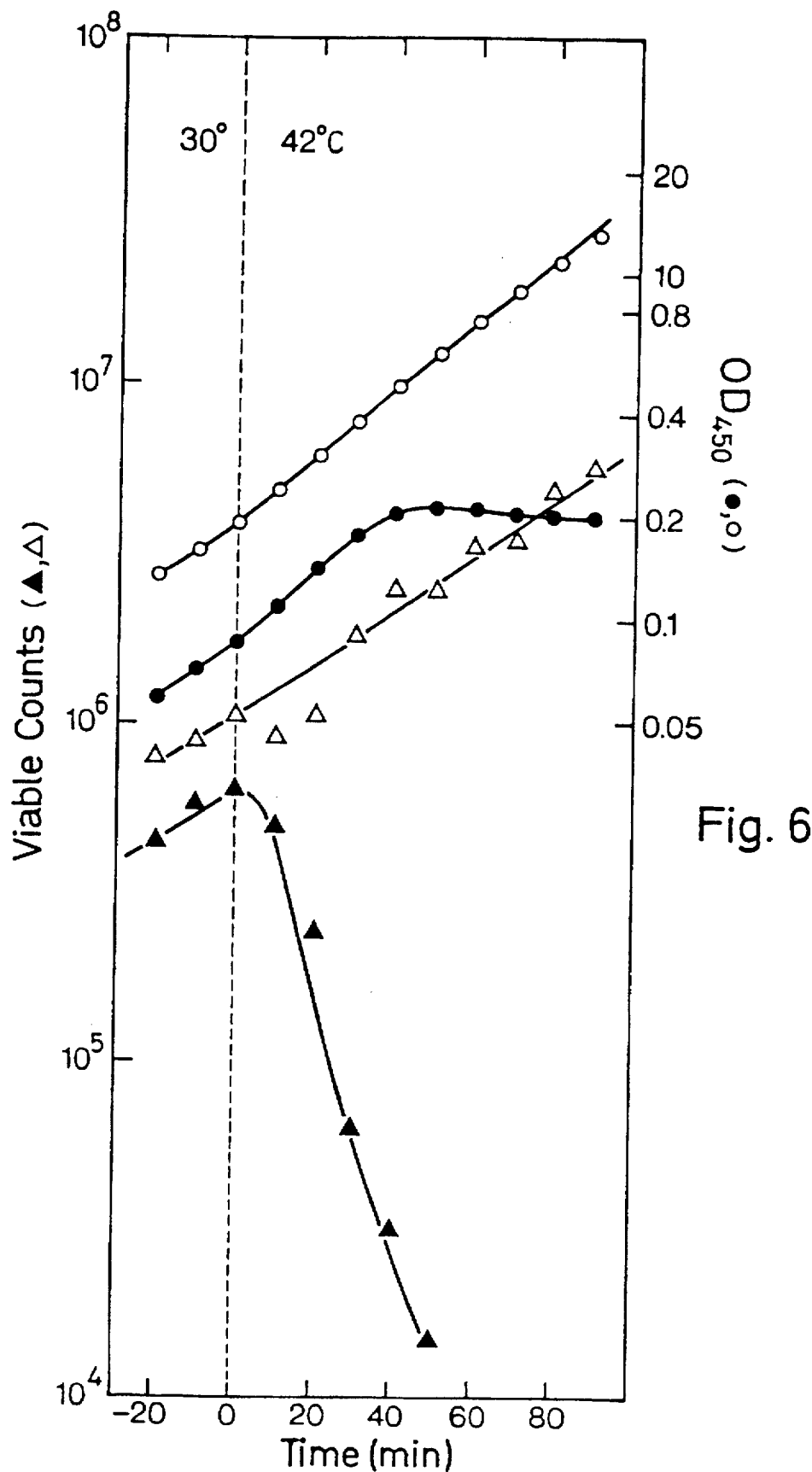
FIG. 6 shows the suppression of host cell killing. Strain JC411 containing either pF634 alone (closed symbols) or pF634 plus pPR633 (open symbols) was grown exponentially in A+B minimal medium supplemented with casamino acids at 30° C. At time zero, the temperature was shifted to 42° C. and growth of the cultures was followed by measuring the optical density (OD$_{450}$) and viable counts on selective medium (LB plates containing 100 µg/ml kanamycin).

Suppression of the Host Killing Effect Expressed by Hok (cf. FIG. 6)

A gene from which a highly toxic product is expressed must obviously be regulated. Therefore, it was assumed that the regulator of hok was also encoded by the parB$^+$ region. In a first attempt to characterize this regulatory loop, the fragment of pKG634 containing λcI857 upstream of the hok gene was inserted into a mini-F plasmid, resulting in pF634. FIG. 6 represents the induction of killing of JC411 (pF634) which shows that the killing occurs somewhat slower and less efficiently than in the case of pKG634 in accordance with the low copy number of F compared to pBR322.

A second parB$^+$ plasmid (pPR633) was subsequently transformed into strain JC411 (pF634) and the induction experiment repeated with this double plasmid strain. As seen in FIG. 6, the parB$^+$ region present in trans fully suppresses the transcriptional activation of the hok gene. Thus, the parB$^+$ region encodes a suppressor of host killing (the sok gene).

Employing this experimental design as an assay, the sok gene was mapped in the following way: Double plasmid strains containing pF634 and one of the deletion derivatives pPR634, pPR341, pPR154, or pPR171, respectively, were constructed, and by following the growth pattern of these strains at 42° C., the Sok phenotype of the deletion derivatives was determined by measuring growth after the temperature shift. The analysis of these deletion derivatives showed that the plasmids pPR634 and pPR154 express Sok activity, whereas the plasmids pPR341 and pPR171 express non-detectable levels of Sok activity.

The plasmids were also tested for the incompability phenotype characteristic for parB$^+$ (cf. International Patent Application No. PCT/DK83/00086, Publication No. WO 84/01172), and it was found that plasmids expressing Sok activity also exert parB specific incompatibility, whereas plasmids which are Sok$^-$ as described above do not exert incompatibility. Thus, the parB incompatibility reaction represents an assay for Sok activity.

In a manner similar to that described for the hok gene, the region required for sok gene activity has been further narrowed down. One of the sok$^-$ derivatives used in the mapping procedure, pPR171, contains the parB$^+$ region extending from coordinate −300 to +288 (FIGS. 1 and 3). A restriction fragment containing the λcI857 and λpR was inserted into pPR171 in such a way that the λpR promoter reads into the sok region of the plasmid, resulting in pKG171 (cf. Materials and Methods).

Plasmid pKG171 was transformed to strain CSH50 containing pOU94. Plasmid pOU94 is a lac$^+$ parB$^+$ p15 derivative which is completely stably inherited due to the presence of the parB$^+$ region on the plasmid. Introduction of other parB$^+$ plasmids into that strain results in destabilization of pOU94 due to the incompatibility expressed from parB$^+$. At 30° C., the presence of pKG171 did not result in destabilization of pOU94 to any significant extent, whereas a clear destabilization was detected at 42° C. Therefore, transcription from right to left into the parB$^+$ region of pKG171 results in activation of the incB region (i.e., the sok gene).

The results described here further narrows down the sok gene which must therefore be located between +194 (pPR634) and +288 (pPR171). Also, it is indicated that the sok gene promoter reads from right to left (opposite of hok gene transcription) and is located at least partly in the region between +288 (pPR171) and +336 (pPR154). A putative −10 sequence (TATCCT) is located at position +262 and a −35 sequence (TTGGGC) is located at position +285 (FIG. 3) (Hawley and McClure, Nucleic Acids Res. 11, 1983, pp. 2237–2255). It is assumed that these sequences constitute the promoter of the sok gene.

EXAMPLE 5

Figure 8A:
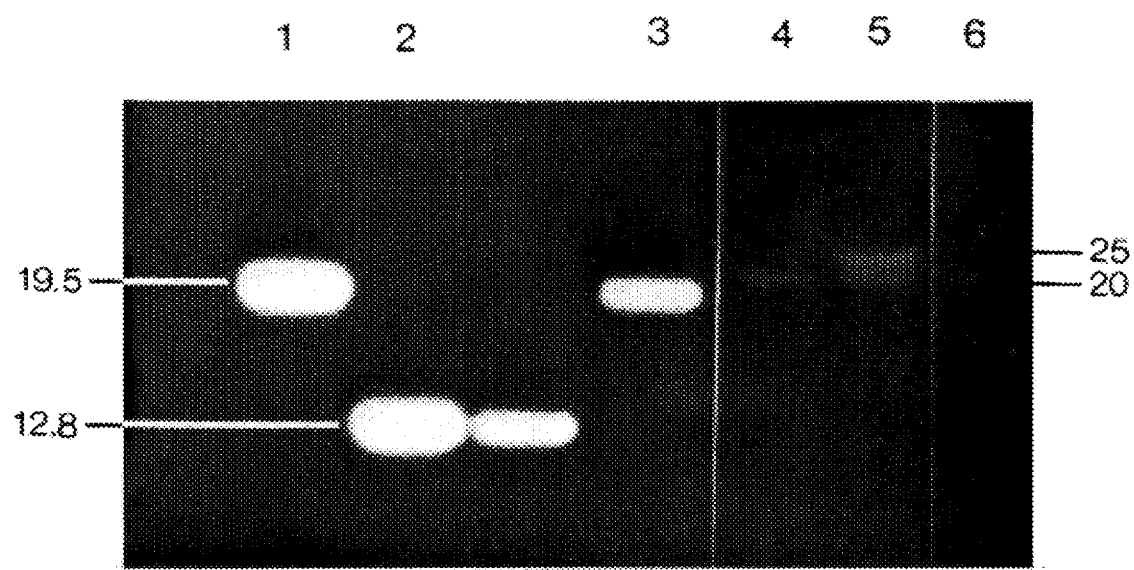
FIG. 8a shows 0.75 µg of EcoRI-restricted total DNA from strains of E. coli analyzed by filter hybridization using the R1 parB probe. Lane 1: R1drd-19; lane 2: R100; lane 3: R386. These lanes were exposed for 30 minutes. Lane 4: RP1; lane 5: R6-K; lane 6: plasmid-free E. coli. These lanes were exposed for 5 hours. Sizes of relevant fragments are given in kilobases.

Discovery of an *E. coli* Chromosomal Homologue of R1 parB (cf. FIG. 8a)

Since plasmid evolution has involved an extensive exchange of genetic information between bacterial chromosomes and freely replicating DNA molecules, the chromosomal DNA of *E. coli* was analyzed for possible ancestral sequences to the R1 parB sequences.

In lane 6 in FIG. 8a, total EcoRI-restricted DNA from plasmid-free *E. coli* JC411 was analyzed by filter hybridization to a parB probe, cf. Materials and Methods. A fragment of 20 kb is seen to yield a rather weak, but definite signal which can also be detected in other lanes containing *E. coli* DNA if exposed for the same time (lanes 4, 5). The chromosomal sequence is estimated to be approximately 55% homologous to parB. The chromosomal sequence is named parl in the following.

A major question is of course to which extent the finding of homology at the level of the nucleotide sequence also reflects similarity in function of the products encoded by the homologous regions, an aspect which will be further dealt with in Example 6.

EXAMPLE 6

Generic Organization of an *E. coli* Chromosomal Homologue of R1 parB and its Functional Relationship to R1 parB (cf. FIG. 7)

The hok gene of plasmid R1, defined in Example 3, codes for a polypeptide of 52 amino acids. The amino acid sequence of the hok gene product was compared to a large number of known protein sequences. Surprisingly, a polypeptide of 51 amino acids encoded by the relB-orf3 gene of the *E. coli* relB operon (Bech et al., *The EMBO Journal* 4, 1985, pp. 1059–1066) showed significant homology to the hok product. The amino acid sequences of the two homologous proteins are presented in FIG. 7, which shows that 42% (22) of the amino acids are identical in the two proteins. For 17% (9) of the amino acids the changes are conservative, meaning that one amino acid has been replaced with an amino acid of similar chemical characteristics (i.e. hydrophobicity, charge, etc.), resulting in an overall homology of 61%. Especially the charged amino acids are well conserved as are the cysteine residues at positions 16 and 31 (FIG. 7).

The DNA sequences of the hok gene and of relB-orf3 were also compared as shown in FIG. 7. The coordinates used in the following are parB$^+$ sequence coordinates as in FIG. 3. From coordinates +290 to +460, there is 55% homology between the two sequences. It appears from FIG. 7 that the conserved region includes nucleotides upstream and downstream of the protein coding sequence located from +304 to +460. The conservation of bases outside the coding region indicates that regulatory features of the two genes have also been at least partly conserved.

To show that the sequence homology reflects similarity in function, a plasmid carrying the fpR promoter fragment upstream of the relB-orf3 gene was constructed (cf. the description of an analogous type of construction used in mapping the hok gene in Example 3).

When λpR mediated transcription into relB-orf3 is induced, a rapid killing of the cells is observed with a kinetics similar to that observed for bacteria containing plasmid pKG341 as described in Example 3. Simultaneously, all the cells in the culture are transformed into the hok characteristic "ghost" cells (cf. FIG. 5).

Thus, there is a striking homology between the hok gene of plasmid R1 and the relB-orf3 of the *E. coli* relB operon both at the structural and functional level.

EXAMPLE 7 parB Homologous Sequences on Various Plasmids (cf. FIG. 8a)

Filter hybridization analysis of total, EcoRI-restricted DNA from a number of strains of *E. coli* harbouring various plasmids was carried out using the parB probe (lanes 1–5 in FIG. 8a).

The plasmid R1drd-19 is a member of the R1 plasmid family from which the parB probe was originally cloned. R1drd-19 is present at two copies per bacterial genome. EcoRI-restricted total DNA from *E. coli* 1005/R1drd-19 is analyzed in lane 1. A strongly hybridizing fragment of 19.5 kb is seen, the size of which is consistent with the genetic mapping of the parB function to the 19.5 kb R1 plasmid (International Patent Application No. PCT/DK83/00086, Publication No. WO 84/01172).

The plasmid R100 is closely related to R1 carrying a transposable element, Tn10, within the region equivalent to the 19.5 kb EcoRI-A fragment of R1. The transposon contains the recognition sequence for EcoRI and, consequently, a further EcoRI site is introduced into the R1-like EcoRI-A fragment splitting this into the two EcoRI-A and EcoRI-D fragments of R100 (Miki et al., *J. Bacteriol.* 144, 1980, pp. 87–99). These two EcoRI fragments of R100 both contain sequences found by heteroduplex mapping to be homologous to sequences present of the F factor (Sharp et al., *J. Mol. Biol.* 75, 1973, p. 235). A strongly hybridizing fragment of 12.8 kb is seen in lane 2, FIG. 8a, thereby mapping the parB region of R100 to the EcoRI-D fragment of R100, within the center of the region of homology between R1 and R100, and F.

This localization of parB within the F homology region of R100 prompted the search for parB-like sequences on plasmids belonging to the incompatibility group, IncFI.

EcoRI-restricted, total DNA from B210/R386, an *E. coli* strain harbouring the IncFI plasmid R386, was analyzed by filter hybridization using the parB probe (lane 3, FIG. 8a).

The plasmid R386 which belongs to the same incompatibility group as F was found to give a parB hybridization signal corresponding to an EcoRI fragment of 19.5 kb. Since this plasmid is present at 0.5–1 copies per genome, the finding of a signal of approximately one third of the R100 signal (lane 2, FIG. 8a) suggests that the degree of homology between R1 parB and the R386 parB-like sequences is 55–60%.

The search for parB-related sequences was extended to other incompatibility groups. The plasmid RP1, which belongs to the incompatibility group IncP, was analyzed.

With the parB probe, total, EcoRI-restricted DNA from 1005 (RP1) yields a hybridization signal corresponding to the EcoRI-linearized plasmid (lane 4, FIG. 8a). In addition, a hybridizing band of 20 kb corresponding to parI is seen, which was discussed in Example 5.

Since RP1 is adapted to stable maintenance in a broad range of gramnegative bacterial hosts, the finding of parB-related sequences on RP1 opens the possibility that maintenance systems analogous to the R1 parB system, which is operative in *E. coli* as well as in *Pseudomonas putida* (Example 11), may function in a multitude of bacterial hosts.

Yet another plasmid, R6-K (IncX incompatibility group), was found to carry sequences with approximately the same hybridization characteristics as RP1 as evidenced by the presence of a 25 kb EcoRI fragment of R6-K hybridizing the parB probe (lane 5, FIG. 8a).

The low copy number plasmid F has been analysed in some detail in order to determine whether the presence of R1 parB hybridizing sequences reflect the existence of a stabilization mechanism related to that of R1 parB.

Two plasmid stabilization functions have been identified within the genome of F and the corresponding genes (sop (Ogura and Hiraga, *Cell* 32, 1983, pp. 351–360) and ccd (Ogura and Hiraga, *Proc. Natl. Acad. Sci. USA* 80, 1983, pp. 4784–4788)) have been located to the EcoRI fragment spanning the map positions 40.3 to 49.5.

Filter hybridization analysis of total DNA from *E. coli* 1005 harbouring F showed that R1 parB-related sequences were present on a 10.7 kb EcoRI fragment of F (map position 49.5 to 60.2) and further hybridization analyses of 1005(F) DNA digested with EcoRI and/or BamHI mapped these sequences to a 4.5 kb BamHI-EcoRI fragment extending from map position 55.7 to 60.2. This indicates the existence of a third plasmid stabilizing function within F.

The region of F hybridizing the R1 parB probe was subsequently cloned into a bacteriophage λ vector. EcoRI-digested DNA from 1005(F) was size-fractionated by preparative agarose gel electrophoresis and fragments of 9.5 to 12 kb were recovered by electroelution from the gel. The fragments were ligated to the EcoRI sites of the left and right arms of λL147 and packaged in vitro to yield infectious phages (cf. Maniatis et al., *Molecular Cloning*, Cold Spring Harbor, N.Y., 1982, p. 256) which were then used to infect *E. coli* LE392. Recombinant phages carrying the R1 parB-related sequences were identified by plaque hybridization.

From a recombinant phage carrying the 10.7 kb EcoRI fragment which includes the R1 parB-related sequences, the fragment was isolated and inserted into pUC8 at the EcoRI site. In one resulting plasmid, pNL1, the insert is so oriented that cleavage of pNL1 DNA with BamHI results in excision of a 4.5 kb fragment carrying the R1 parB hybridizing sequences.

The 4.5 kb BamHI fragment from pNL1 was isolated and the region hybridizing the R1 parB probe was mapped to an RsaI fragment of 870 bp by filter hybridization analysis. The 870 bp RsaI fragment was isolated and inserted into the SmaI site of M13mp9. A number of recombinant phages carrying the R1 parB related sequences on a 870 bp insert was identified by plaque hybridization. The nucleotide sequence of the inserted DNA was analysed according to Sanger et al., *Proc. Natl. Acad. Sci. USA* 74, pp. 5463–5467.

The nucleotide sequence of part of one of the recombinant phages, mpNL12, comprises 402 bases extending from the RsaI site and this sequence is 90% homologous to the region from +178 to +580 of the R1 parB sequence (FIG. 3). All essential features of the R1 parB region are also found in the F-derived sequence: (1) an open reading frame encoding a protein of 50 amino acids is present corresponding to the R1 hok gene, (2) the ribosome binding site of R1 hok is conserved, (3) the region corresponding to the 3' non-translated part of R1 parB mRNA, which is believed to be essential for hok mRNA stability, is highly conserved (90% homology), and (4) the putative −10 and −35 regions of R1 sok are also conserved.

The open reading frame within the F-derived sequence codes for a protein of 50 amino acids which differs only slightly from the R1-specified hok protein. Firstly, two codons in R1 hok have been deleted, namely val-15 and ser-29. Secondly, two conservative substitutions have occurred, namely leu-16 to val and his-39 to tyr.

Evidently, the R1 hok gene and the related sequences on F derive from a common ancestral sequence and, furthermore, the conservation of a coding region corresponding to R1 hok strongly suggests that the encoded protein is involved in the stabilization of F.

To test for plasmid stabilizing properties of the F-derived sequence, the 4.5 kb BamHI fragment from pNL1 which carries the F hok-like sequences was inserted into pJEL82, a low copy number plasmid with a loss frequency of $10^{-2}$ per generation (cf. PCT/DK83/00084, Publication No. WO84/01171). The resulting plasmid, pJEL82/F, as well as pJEL82 was transformed into *E. coli* HB101. Cultures of the two strains were grown for 16 hours without selection pressure and the fraction of plasmid-containing cells ($Ap^R$) was determined. The result was as follows:

| plasmid | % $Ap^R$ cells |
| --- | --- |
| pJEL82 | 36.5 |
| pJEL82/F | 98.4 |

It was therefore concluded that the 4.5 kb BamHI fragment carrying R1 parB related sequences exerts a plasmid stabilizing effect. If the stabilization is due to the presence of the hok-like gene within the F fragment, the emergence of ghost cells would be expected in cultures of cells harbouring pJEL82/F grown without selection pressure, cf. Example 3. An overnight culture of cells containing pJEL82/F was found to contain approx. 5% ghost cells indistinguishable from R1 hok induced ghost cells.

In case of F, the demonstration of sequences related to R1 parB by filter hybridization thus reflects the existence of a functionally similar plasmid stabilization mechanism.

EXAMPLE 8

Figure 8B:
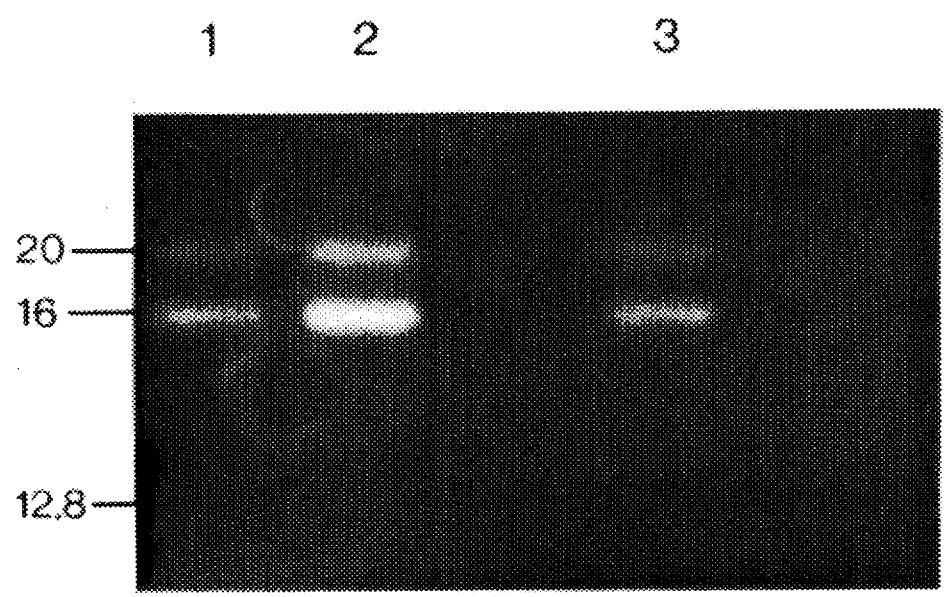
FIG. 8b shows 0.75 µg of EcoRI-restricted total DNA from strains of E. coli analyzed by filter hybridization using the relB-orf3 probe. Lane 1: R100; lane 2: R386; lane 3: plasmid-free E. coli. Time of exposure: 3.5 hours. Sizes of relevant fragments are given in kilobases.

Stepwise Hybridization as a Strategy for the Detection of Replicon Stabilizing Sequences Homologous to parB Related Sequences (cf. FIG. 8b)

The conditions of hybridization determine the level of homology between a probe and a filter-bound DNA species required to yield a detectable signal, cf. the discussion in Materials and Methods. Consequently, filter-bound sequences may exist which remain undetectable with the given probe under the given set of hybridization conditions but which may nevertheless encode a hok-like activity, cf. the discussion of homology versus function in Materials and Methods. This is illustrated in the following experiment.

As described in Example 6, the relB-orf3 represents a chromosomal homologue of R1 parB based on the sequence comparison data and the functional similarity of hok and relB-orf3. The relB-orf3 and flanking sequences, as present in plasmid pBD2724, was used as probe in a filter hybridization analysis of *E. coli* chromosomal DNA.

Plasmid pBD2724 is a pBR322 derivative containing a HincII-MluI fragment from the relB operon of *E. coli* comprising the relB-orf3 coding sequence (coordinates 1070–1350 according to Bech et al., op. cit.).

In lane 3, FIG. 8b, total EcoRI-restricted DNA from plasmid-free *E. coli* is analyzed by filter hybridization using the relB-orf3 probe. In addition to the 20 kb hybridizing fragment likely to represent the above-identified par1 sequence (Example 6), yet another hybridizing fragment of 16 kb is detected. Since the intensity of the latter is greater than the intensity of the 20 kb signal, the 16 kb EcoRI fragment must span the *E. coli* relB-orf3 gene used as hybridization probe, i.e. the intensity of the 16 kb signal provides a reference from which degrees of homology can be estimated. The intensity of the par1 hybridization signal, which is approximately ¾ of the relB-orf3 signal, suggests that par1 is approximately 65–70% homologous to relB-orf3. Since the 16 kb relB-orf3-carrying fragment is not detected with the parB probe (lane 6, FIG. 8a), R1 parB is 50% or less homologous to relB-orf3.

In Example 5 it was found that the parB probe detects the 20 kbp chromosomal homologue but not the 16 kbp homologue representing the relB-orf3 according to the above data. Since, as described in Example 6, the latter exerts hok-like activity when expressed, it can be assumed that the par1 will also express hok-like activity or sok-like activity and/or both activities when properly expressed.

The relB-orf3 fragment was used as a probe in filter hybridization analysis of *E. coli* harbouring plasmid R100, and R386, both of which contain R1 parB-like sequences (FIG. 8a, lanes 1 and 2). Under the present set of hybridization conditions, the relB-orf3 probe did not detect these sequences (FIG. 8b, lanes 1 and 2) since only the 20 kb par1 and the 16 kb relB-orf3 carrying fragment are seen to hybridize the probe, thereby indicating that the absence of hybridization between a probe from a region expressing hok or hok-like activity and a given DNA-species does not preclude that the DNA-species in question can exert hok-like activity if properly expressed. Consequently, the finding of homology between the DNA-species in question and a region expressing hok or hok-like activity strongly suggests that the DNA-species in question will exert hok or hok-like activity if properly expressed.

The above data therefore reveal a useful strategy in searching for regions exerting hok/sok-like activities: A probe representing a region of nucleic acid comprising hok or hok-like genes (e.g. R1 parB) is used to detect homologous sequences (e.g. par1) within the genome in question (e.g. chromosomal or plasmid DNA) which are subsequently tested for hok or hok-like activity (as done for the relB-orf3 region) in the proper experimental settings, and if shown to encode such activity or activities are next used themselves as probes in a second round of hybridizations to define novel homologous sequences which may or may not be related to the probes used in the first round of hybridizations (e.g. R1 parB). This stepwise procedure combining nucleic acid hybridization and functional assays of the isolated nucleic acid sequences may be adapted as a general strategy to search for genes expressing hok or hok-like activities in genomes increasingly separated from E. coli on the evolutionary scale.

EXAMPLE 9

Figure 9B:
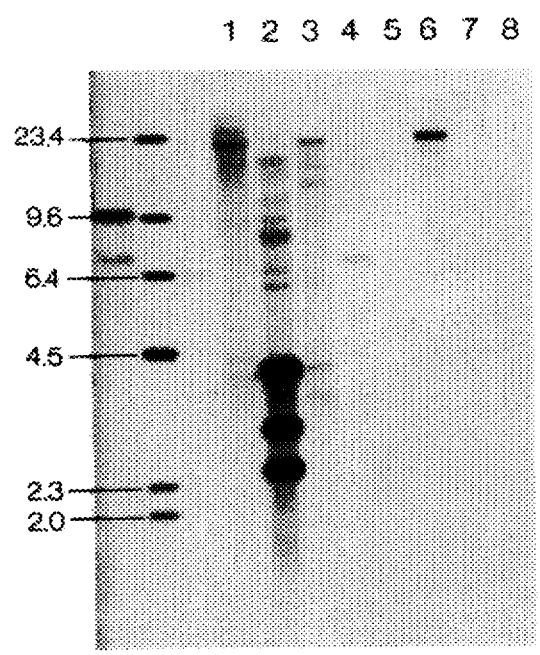
FIG. 9 shows 0.5–0.75 µg of EcoRI-restricted total DNA from various bacteria analyzed by filter hybridization using the R1 parB probe. The autoradiogram was exposed for 17 hours. Two different photographic exposures of the same autoradiogram are shown: Lane 1: *Salmonella typhimurium* (not discussed in the text); lane 2: *Serratia marcescens*; lane 3: *Pseudomonas fluorescens*; lane 4: *Pseudomonas putida*; lane 5: *Proteus vulgaris* (not discussed in the text); lane 6.
Figure 9A:
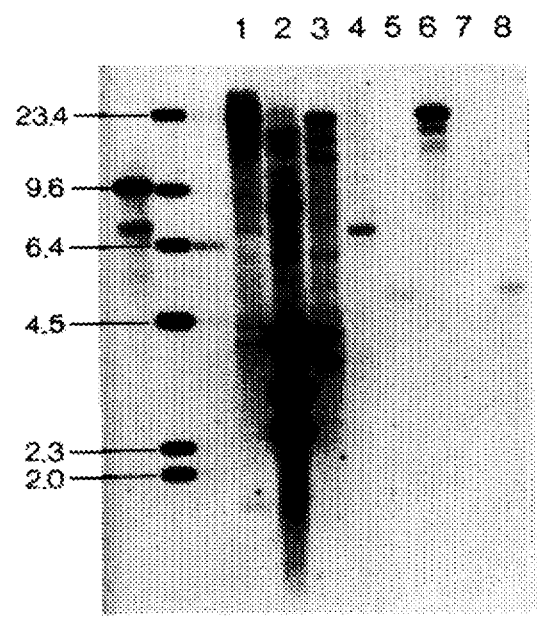

Detection of parB Related Sequences in Bacteria (cf. FIGS. 9 and 10)

In the previous Examples, it was demonstrated 1) that sequences related to R1 parB are widely distributed among bacterial plasmids isolated from gram-negative bacteria, and 2) that sequences related to R1 parB are present in the chromosomal DNA of E. coli. These findings prompted a search for sequences related to either R1 parB or one of the chromosomal counterparts (E. coli relB-orf3) in DNA from a variety of bacteria, as part of either their chromosomal DNA or of plasmids naturally present in these organisms.

Filter hybridization analysis of EcoRI-restricted DNA from Serratia marcescens with the R1 parB probe shows intense hybridization to 3 fragments of 4.1, 2.9 and 2.5 kb (lane 2, FIG. 9). Only the 4.1 kb fragment also hybridizes the relB-orf3 probe (lane 1, FIG. 10). The parB probe hybridizes an additional 6 fragments. Two of these signals are stronger than the parB signal derived from the relB-orf3-carrying 16 kb fragment in E. coli DNA (lane 6, FIG. 9). Hybridization of Serratia marcescens DNA with the E. coli relB-orf3 probe yields a number of weak hybridization signals. It is possible that the strongly hybridizing bands of 2.5, 2.9 and 4.1 kb are derived from plasmid(s) although the agarose gel electrophoresis did not reveal any high copy number plasmids.

Pseudomonas fluorescens was analyzed as a plasmid-free member of this species. Hybridization of DNA from Pseudomonas fluorescens with R1 parB (lane 3, FIG. 9) shows 8–10 hybridizing fragments, 4 of which exhibit signals with intensities of approximately 33% of the chromosomal counterpart of R1 parB (lane 6, FIG. 9). A single of these fragments, of approximately 13 kb, probably also hybridizes the E. coli relB-orf3 probe (lane 2, FIG. 10). In addition, the relB-orf3 probe identifies 5 fragments specifically, although at low signal intensity: two of these, of 5.5 and 5.6 kb, are also seen in DNA from Pseudomonas putida when this DNA is analyzed using the relB-orf3 probe (lane 3, FIG. 10). The relB-orf3 probe hybridizes to an additional 5 fragments in Pseudomonas putida DNA, but none of these fragments are recognized by the R1 parB probe (lane 4, FIG. 9). In Pseudomonas putida DNA, the parB probe detects approximately 10 fragments of low signal intensity and a single quite strongly hybridizing fragment of approximately 7.3 kb.

Among gram-positive bacteria, B. subtilis, B. circulans PL236 and two strains of Lactobacillus were analyzed for the presence of sequences related to either R1 parB or E. coli relB-orf3.

In case of the parB probe, a single quite strongly hybridizing fragment of 5.2 kb was found in DNA from B. circulans (lane 8, FIG. 9). Very weak signals were obtained from a few additional fragments of B. circulans DNA. With the relB-orf3 probe, a limited number of hybridizing fragments was seen in DNA from B. subtilis (lane 4, FIG. 10), B. circulans (lane 5, FIG. 10), and Lactobacillus (lanes 6 and 7, FIG. 10). The number of relB-orf3-hybridizing fragments ranged from 6 to 11, and all have approximately the same signal intensity. In the Lacrobacilli, agarose gel electrophoresis has demonstrated the presence of plasmids suggesting the possibility that at least some of the hybridizing sequences are of plasmid origin. A search for plasmids in B. circulans PL 236 has been negative suggesting that the sequence of B. circulans DNA hybridizing the R1 parB probe (lane 8, FIG. 9) may be of chromosomal origin.

The above experiments indicate that sequences related to R1 parB and/or to E. coli relB-orf3 are widely distributed among bacterial species, not only the Enterobacteriaceae from which the probes were derived, but also the gram-positive bacteria.

EXAMPLE 10

Detection of parB Related Sequences in Eukaryotic Cells (cf. FIG. 11)

A unicellular organism was investigated, namely the ciliate protozoan Tetrahymena thermophila, FIG. 11. This organism is characterized by 1) a high number of mitochondrial DNA molecules per cell and 2) approximately 12,000 copies of ribosomal RNA genes located on self-replicating rDNA molecules. Neither the R1 parB probe nor the E. coli relB-orf3 probe detect any fragments in DNA prepared from isolated macronuclei (lane 1, FIG. 11). Nor did the probes hybridize to the two EcoRI fragments of isolated rDNA (lane 3, FIG. 11). Total EcoRI-restricted DNA from Tetrahymena thermophila, which includes mitochondrial DNA, showed two hybridizing fragments, of 6.6 kb and 3.3 kb (lane 2, FIG. 11), with the relB-orf3 probe while the parB probe did not yield any signals. The hybridizing fragments co-migrated with two EcoRI fragments of mitochondrial DNA that were readily detectable by ethidium bromide staining of the gel prior to DNA transfer.

Chloroplast DNA from pea (Pisum sativum) was cleaved with the restriction endonuclease PstI, and 0.125 microgram was analyzed by filter hybridization using the parB and the relB-orf3 probes (lane 4, FIG. 11). The latter probe hybridizes to a fragment of approximately 16 kb.

Finally, two samples of human cellular DNA were analyzed by filter hybridization following EcoRI restriction. The R1 parB probe yielded a (weak) hybridization signal to the neuroblastoma DNA (lane 5, FIG. 11) as well as to the embryonic liver DNA (lane 6, FIG. 11). The high mitochondrial content of liver tissue may indicate that the observed signal in lane 6, FIG. 11, is derived from human mitochondria. The neuroblastoma DNA was analyzed since other hybridization analyses had indicated selective amplification of a small chromosomal region leading to the presence of extrachromosomal mini-chromosomes ("double minutes"); the origin of the hybridization signal in lane 5, FIG. 11, is unknown.

Simultaneously, all the cells in the culture are transformed into the hok characteristic "ghost" cells (cf. FIG. 5).

Thus, there is a striking homology between the hok gene of plasmid R1 and the relB-orf3 of the *E. coli* relB operon both at the structural and functional level.

EXAMPLE 11

Construction of a Trp-Hok Fusion

Plasmid pPR341 carries the hok$^+$ gene from the parB region without its natural promoter (cf. Table 1 and FIG. 3). Plasmid pSGS8 carries the trp operon on an EcoRI fragment inserted in pBR322. An XhoI-EcoRV fragment (ca. 700 bp) from pSGS8 carrying the trp promoter was inserted by ligation in pPR341 digested first with BamHI (this site was made blunt-ended through a filling-in reaction with Klenow polymerase) and then with SalI. This insertion placed the trp promoter fragment in such an orientation that transcription would enter the hok gene. After transformation to MC1000 colonies were selected on LB plates containing ampicillin and subsequently, the colonies were tested for growth on A+B minimal plates containing leucine and ampicillin. In the absence of tryptophan, the trp promoter is induced, and transcription into the hok gene was assumed to be lethal. Therefore, screening was for clones that did not grow on the minimal plates. One such clone harbouring a plasmid, p341-1, which was shown by restriction enzyme mapping to have the correct insertion, was chosen for further analysis (cf. FIG. 12).

EXAMPLE 12

Growth of Cells Harbouring p341-1

MC1000 (p341-1) was grown in A+B minimal medium supplied with 0.2% glucose and 1% casamino acids. Casamino acids contain very little tryptophan, so it was expected that at a certain cell density, the medium would be depleted of tryptophan. This situation mimics growth in a natural environment with a limited supply of tryptophan which is a rare amino acid. As seen in FIG. 13, the initial growth rate of the plasmid carrying strain (hok$^+$) is identical to that of a plasmid-free MC1000 strain. However, at a cell density of approximately $OD_{450}=0.8$, growth of MC1000 (p341-1) stops abruptly, indicating induction of the hok gene (verified by microscopic examination of the cells, cf. FIG. 5), whereas the plasmid-free strain keeps growing. Viable counts from MC1000 (p341-1) at this point and one hour later show a dramatic reduction in viability (less than $10^{-4}$). In conclusion, the presence of p341-1 in an *E. coli* K-12 strain makes growth and viability dependent on the presence of tryptophan in the growth medium. When this amino acid is exhausted from the environment, growth stops immediately and the cells are killed.

EXAMPLE 13

Use of an R1 Hok Homologue in the Construction of a Biological Containment System The F hok gene (cf. Example 7) and the trp promoter were combined to generate a biological containment system. From pNL1 described in Example 7, the 850 bp RsaI fragment hybridizing the R1 parB probe was cloned into SmaI-restricted M13mp11. A recombinant, mpNL4, was identified in which the ribosomal binding site of F hok as well as the coding region of F hok could be excised as an approximately 300 bp FspI-EcoRI fragment. This approximately 300 bp fragment, the 550 bp EcoRV-XhoI fragment of pSGS8 containing the trp promoter as well as the initial portion of trpE, and the 3.7 kb SalI-EcoRI fragment of pBR322 carrying the bla gene were ligated to generate pNL7. In this construct, the trp promoter will transcribe into F hok. The plasmid pNL7 has the correct restriction enzyme pattern, and *E. coli* HB101 cells transformed with pNL7 show growth inhibition on plates without tryptophan as described for p341-1 transformants in Example 12.

The maximum inducible cell death caused by the expression of the F hok gene on pNL7 was determined for *E. coli* HB101 transformed with pNL7, HB101(pNL7). The cells were grown in Modified A+B (MA+B) which comprises A+B medium supplemented with thiamine, leucine, proline, 0.4% glucose, 1% casamino acids, and ampicillin (50 µg/ml) with further addition of tryptophan at varying concentrations (0–200 µg/ml). The cells were grown to the early exponential phase at which time 100 µg/ml of indolyl acrylic acid (IAA) was added which substance competes with tryptophan for binding to the repressor, thus leading to inactivation of the repressor. The number of viable cells per ml was determined by plating samples of the IAA-treated cultures onto LB plates with 50 µg/ml ampicillin at 30 minutes following IAA induction. *E. coli* HB101(pBR322) served as a control in these experiments. The maximum killing effect on IAA addition was observed at 5–10 µg/ml tryptophan, the surviving fraction of HB101(pNL7) being $1.4 \times 10^{-4}$. The control cells were unaffected by IAA addition.

The kinetics of IAA-induced killing of HB101(pNL7) grown in the above medium with 5 µg/ml tryptophan is bipbasic with an exponential component from 0 to 15 minutes at which time the surviving fraction comprises less than $10^{-3}$, and a second linear phase extending beyond 90 minutes which further reduces the surviving fraction by a factor of 10 or more.

Simulated release experiments were carried out by growing *E. coli* HB101(pNL7) under conditions leading to depletion of tryptophan and hence to activation of the trp promoter. The cells were grown in MA+B medium with either no added tryptophan or supplemented with 5 µg/ml tryptophan. $OD_{600}$ and viable cells per ml was followed. The control was HB101(pBR322).

In one experiment, no tryptophan was present in the growth medium, and as shown in FIG. 14, the $OD_{600}$ of HB101(pNL7) increased exponentially for several hours, albeit at a slower rate than the control culture, but no corresponding increase in cell number was seen. Microscopically, the cell size of pNL7-transformed cells increased during this phase. Since viable counts did not drop, it is assumed that a low, but tolerable expression of F hok took place. Upon depletion of tryptophan, killing of HB101(pNL7) was observed, the surviving fraction being $2 \times 10^{-3}$.

In a second experiment, HB101(pNL7) and HB101 (pBR322) were grown in MA+B supplemented with 5 µg/ml tryptophan. As appears from FIG. 15, the two strains had identical generation times during the first phase of the experiment as determined by $OD_{600}$, and in this experiment the increase in $OD_{600}$ in the HB101(pNL7) culture reflected an exponential increase in cell number. Thus, the mere presence of the F hok system within *E. coli* does not affect cell growth as long as tryptophan is present in the growth medium. At the time of tryptophan depletion, the F hok is expressed due to derepression of the trp promoter resulting in killing of the cells so that the surviving fraction is reduced to $10^{-3}$ within one hour.

41

Using the above construction with F hok, a substantial fraction of cells survive induction of expression of the killing function. This might in principle be due to one or a combination of several factors: structural instability of pNL7, adaptation of HB101(pNL7) to the toxic effect of the hok protein, selection of plasmid-free cells in the population, or insufficient expression of F hok in individual cells due to the combined effect of a relatively low level of transcription even in the induced state as the trp attenuator is present and selection of cells with low copy numbers.

To approach this question, *E. coli* HB101(pNL7) surviving either 90 minutes of IAA induced F hok expression or induction of hok expression due to tryptophan depletion following growth with or without exogenously added tryptophan was analysed. The survivors from the depletion experiments were sampled 1 hour following the deflection of the $OD_{600}$ curves in FIGS. 14 and 15. In these three cases, all surviving colonies tested were resistant to 50 µg/ml ampicillin, but survivors from the depletion experiment in which no exogenous tryptophan had been added (FIG. 14) showed a 50% decrease in cells resistant to 500 µg/ml ampicillin. Thus, a continued low-level expression of a hok protein may lead to selection of cells with a low plasmid copy number. 12 ampicillin-resistant colonies from each of the three induction experiments were grown in LB medium with 50 µg/ml ampicillin to the early exponential phase at which time IAA was added to 100 µg/ml. The number of viable cells per ml was determined 90 minutes after IAA addition. In all 36 experiments, the expected killing was observed, the surviving fraction varying between $10^{-3}$ and $10^{-4}$. It is therefore concluded that the survival of HB101 (pNL7) on induction of the F hok system is due to selection of cells in which the level of expression of hok protein does not exceed a threshold value, e.g. due to selection of cells with a low plasmid copy number. The efficiency of hok-based biological containment systems may therefore be further improved by substituting a stronger promoter and/or by increasing the translational efficiency of the hok mRNA.

EXAMPLE 14

The Effect of a $\lambda P_R$ Promoter on the Expression of the Hok Gene

Treatment of pPR633 with the exonuclease Bal31 resulted in a series of deletions in the 5' end of the coding strand of the parB region, two of which are shown in FIG. 16a. The plasmid pPR341 is described in Example 3. Plasmid pPR345 covers the +303–+580 region of parB, which only contains the reading frame of the hok gene (see FIG. 3). The deletion offers neither a promoter nor a Shine-Dalgarno sequence to express the hok gene. Cloning of the BglII-SalI fragment containing the $\lambda P_R$ promoter and the λ repressor (cI857) into pPR345 restricted with SalI and BamHI resulted in plasmid pKG345 (FIG. 16b). Induction of $\lambda P_R$ (at 42° C.) resulted in rapid host killing, which showed that pKG345 showed the hok⁺ phenotype when induced, and that the effect was increased compared with previous constructions.

On closer analysis, the construction showed that the cro⁻ gene of the λ fragment had fused to the hok gene. This resulted in a fusion in which the hok gene was expressed from the $\lambda P_R$ promoter and the cro⁻ Shine-Dalgarno sequence. The increased host killing effect is therefore due to a more efficient translation from the cro⁻ Shine-Dalgarno compared with the natural ribosomal binding site of hok.

FIG. 17 shows the increased killing effect expressed by the cro⁻-hok fusion. The killing kinetics (viable counts) and growth ($OD_{450}$) is shown after a shift to 42° C. of *E. coli* strain MC1000 containing either pKG341 or pKG345. Increase in $OD_{450}$ stops and viable counts decrease rapidly in both cultures, but the host killing effect of the cro⁻-hok fusion is more distinct compared with hok alone (half life for pKG345 of 1 minute).

EXAMPLE 15

Biological Containment of a Plasmid Carrying the Trp-Hok Containment System

Plasmid transfer in natural environments is a highly uncertain risk factor in connection with recombinant DNA applications. Plasmids would therefore be safer to use if they carried functions that after transfer would induce killing of the new host cell. In an attempt to investigate the potential of the hok gene product as a killing factor for other bacterial species, a fusion plasmid of p341-1 and a kanamycin resistant derivative of the mobilizable broad-host-range plasmid RSF1010, pBOE93, was constructed. This hybrid (EcoRI-EcoRI fusion) was transformed to *E. coli* S 17.1, which harbours a conjugative plasmid RP1 derivative inserted in the chromosome. In a series of mobilization experiments, p341-1-RSF1010 was transferred from S 17.1 to *E. coli* 1005, *Serratia marcescens* and *Pseudomonas putida*, respectively. Transfers of pBOE93 and pBOE93 fused with pBR322 were performed as controls.

The results indicated in Table 2 show that all plasmids were transferred with equal frequencies from S 17.1 to 1005 (it was shown that the 1005 (p341-1-RSF1010) transconjugants were killed in the absence of tryptophan).

The vector plasmids were transferred to *S. marcescens* and *P. putida* with very high frequencies, whereas p341-1-RSF1010 was transferred with less than a $10^4$ fold lower frequency to both of these bacteria, even if tryptophan was present all the time. Thus, the hok gene product is lethal even for the very distantly related *P. putida* species, and in both organisms, the *E. coli* regulatory system for the trp promoter is missing, although *S. marcescens* is closely related to *E. coli*. This makes it likely that the great majority of bacteria in the natural environment which have a possibility of receiving *E. coli* plasmids will be killed independently of the external concentration of tryptophan when the trp-hok fusion is present.

TABLE 2

Transfer of p341-trp RSF1010

| Donor | Recipient | Selection | Transfer frequency |
|---|---|---|---|
| S 17.1 (pBOE93) (control) | *E. coli* 1005 | Kan + Nal | >10⁻¹ |
|  | *S. marcescens* | Kan + Tc | >10⁻¹ |
|  | *P. putida* | Kan + Rif | >10⁻¹ |
| S 17.1 (p341-trp RSF1010) | *E. coli* 1005 | Kan + Nal | >10⁻¹ |
|  | *S. marcescens* | Kan + Tc | <10⁻⁵ |
|  | *P. putida* | Kan + Rif | <10⁻⁵ |

EXAMPLE 16

Construction of Biological Containment Systems for Grampositive Bacteria: Identification of Hok as a Suitable Killing Function In the previous Examples, the use of R1 hok as well as homologous genes for the construction of containment systems has been described for a wide range of gramnegative bacteria. However, the widespread use of grampositive bacteria in fermentation and the indications that grampositive bacteria have a potential use in deliberate release productions call for the development of biological containment systems for grampositive bacteria. A prerequisite for constructing containment systems similar to those described above for gramnegative bacteria is that a cell killing function affecting grampositive bacteria can be identified. Since the K1 Hok protein is toxic in a wide range of gramnegative bacteria, possible toxic effects of the Hok protein in grampositive bacteria were investigated.

Preliminary experiments showed that the native promoter and ribosomal binding site from the R1 hok gene does not promote the expression of hok in *B. subtilis*.

In order to obtain expression of hok in *B. subtilis*, the coding sequence for Hok was inserted into an expression vector containing a promoter as well as a ribosomal binding site known to be functional in *B. subtilis*. The plasmid pSI-1 is a modification of pAIQ25 (Yanzura and Henner, *Proc. Natl. Acad. Sci. USA* 81, January 1984, pp. 439–443) in which the $P_{pac-I}$ promoter and the penicillase gene have been replaced by a spac-I promoter followed by a synthetic ribosomal binding site (AAGGAGGTGATC) and a polylinker. A gene inserted into the polylinker of pSI-1 will be expressed if IPTG is added to the growth medium due to the present of the lac operator and the lacI gene on the plasmid (Yanzura and Henner, op.cit.). Before cloning R1 hok into the pSI-1 vector, the hok gene was modified as follows. A double-stranded oligonucleotide corresponding to the N-terminal Hok coding region and with overhangs corresponding to XbaI (5') and SauIIIA (3') cleavages was synthesized by means of a Cyclone™ DNA synthesizer (available from Biosearch Inc., New Brunswick, USA) using the β-LINK cyanoethyl phosphoramidite synthesis method. The oligonucleotide differed from the R1 hok sequences at three positions, one effect being the formation of a HindIII recognition site.

A ligation reaction consisting of the oligonucleotide, a 250 bp SauIIIA-PstI fragment corresponding to the C-terminal portion of the Hok coding sequence (derived from a pUC9 recombinant from which the hok gene can be excised with various restriction enzymes), and pUC18 restricted with XbaI and PstI was used to transform *E. coli* DH5a (available from Bethesda Research Laboratories, USA), selecting on LB plates containing 50 µg/ml ampicillin, 0.004% X-Gal and 1 mM IPTG. From one of the white colonies, the plasmid pLK24 was isolated. This plasmid has the expected physical map as determined by restriction enzyme analysis. The region of pLK24 derived from the synthetic oligonucleotide was sequenced in order to verify the reestablishment of the coding region of the hok gene.

To insert the modified hok gene into pSI-1, the 300 bp hok-carrying XbaI-PstI fragment from pLK24 was isolated and ligated to XbaI and PstI restricted pSI-1, and the ligation reaction was used to transform competent *B. subtilis* BD170 cells according to the procedure described in Sadaie and Kada, *J. Bact.* 153, February 1983, pp. 813–821, with subsequent selection on LB plates containing chloramphenicol (5 µg/ml). Since this construction positions the ATG start codon of hok at a distance of 11 bp from the synthetic ribosomal binding site of pSI-1, chloramphenicol-resistant colonies were further analysed for inhibition of growth, the expected phenotype if hok is active in *B. subtilis*, by plating the transformants on LB plates containing 1 mM IPTG. Growth inhibition was observed for approximately half of the transformants tested. One such transformant, BD170 (pLK26), was further analysed.

Plasmid DNA isolated from BD170(pLK26) showed the expected physical map (FIG. 18) and thus appeared to be structurally stable.

In order to test the toxicity of the R1 hok gene product in *B. subtilis*, BD170(pLK26) and BD170(pSI-1) were grown in LB medium to the early exponential phase ($OD_{600}$) at which time IPTG was added to 2 mM. This induces the spac-I promoter of pSI-1. The $OD_{600}$ and viable cells per ml were determined during the experiment. As can be seen from FIG. 19, the growth rates of the two cultures were identical prior to the addition of IPTG, i.e. the mere presence of the hok gene within *B. subtilis* does not affect cell growth. Following addition of IPTG, the $OD_{600}$ of the BD170 (pLK26) culture was doubled during the first hour of IPTG treatment followed by a period with no increase in $OD_{600}$; this corresponds to the pattern observed for the Hok effect in *E. coli*. Viable counts decreased immediately upon addition of IPTG to the BD170(pLK26) culture (FIG. 20), the surviving fraction being 0.25. No effect of IPTG addition was seen on the control culture. Phase contrast microscopy of BD170(pLK26) one hour after the addition of IPTG showed the appearance of approximately 5% of ghost cells.

Cells surviving 1.5 hours of IPTG induction of hok expression were tested for their sensitivity to re-induction with IPTG. All 25 colonies from surviving cells showed growth inhibition on LB plates containing 1 mM IPTG.

It is concluded from these results that the hok gene product is toxic to grampositive bacteria, and hence it can be used to design biological containment systems according to the principles described in the present specification. The finding that the surviving fraction constitutes 0.25 does not invalidate this statement since survival seems to be due mainly to insufficient expression of the hok gene, a feature which may be modified by, for instance, using a stronger promoter or other standard procedures.

EXAMPLE 17

A Stochastic Killing Effect Obtained by Combination of the Fim and Hok Systems

A stochastic killing effect in *E. coli* K-12 was obtained by a recombinant plasmid which carried the hok gene in connection with the part of the fim gene cluster that specifies the periodic expression of type 1 fimbriae in *E. coli*.

Plasmid pPKL8 (FIG. 21) carries the 300 bp invertible DNA fragment which harbours the promoter for the fimA gene. The plasmid further contains the two regulatory genes fimB and fimE (the "on" and "off" genes, respectively, cf. Klemm et al., *Mol. Gen. Genet.* 199, 1985, pp. 410–414; Klemm, *Embo J.* 5, 1986, pp. 1389–1393). Plasmid pPR341 (FIG. 22) has previously been described (Gerdes et al., *Proc. Natl. Acad. Sci. USA* 83, 1986, pp. 3116–3120).

pPKL8 was restricted with BglII and BclI. The 3.3 kb BglII-BclI fragment containing the fimB and fimE genes and the invertible promoter region was inserted into the BamHI site of pPR341 resulting in plasmid pPKL100 (FIG. 23) which was transformed to *E. coli* K-12 strain MC1000. *E. coli* K-12 cells harbouring this construct grew normally in LB-medium. However, cultures of such cells showed the presence of 1–2% of ghost cells, many of which were abnormally long (FIGS. 24a and b). This is indicative of a periodic transcription of the hok gene with ensuing killing of the host.

In order to determine the orientation of the invertible promoter segment, plasmid pPKL100 was digested with the restriction enzymes SnaBI and SacII. The invertible promoter segment contains a unique site for SnaBI, and by studying the sizes of the resulting fragments, the configuration of the promoter-containing segment was estimated: A 650 bp SacII-SnaBI fragment results from the "on" configuration and a 350 bp fragment indicates the "off" configuration (see FIG. 23). In the absence of selection pressure, a 50/50 distribution of plasmids containing the segment in the "on" and "off" configuration, respectively, is to be expected as exemplified by pPKL8 (lane B in FIG. 25). However, the same pattern was not seen in the case of plasmid pPKL100 where only the "off" configuration was evident (lane A in FIG. 25). This indicates that cells containing plasmid pPKL100 in which the inversional switch is in the "on" configuration are not viable.

EXAMPLE 18

Biological Containment Based on Competition Between Cells With and Without a FimA-Hok Containment System In order further to elucidate whether the invertible DNA segment in plasmid pPKL100 (cf. Example 17) could be influenced in trans by the gene dosage of fimB and fimE, the following constructs were made to complement this plasmid in trans: since plasmid pPKL100 was based on the pBR322 replicon, three plasmids based on the compatible vector pACYC184 were constructed, pLP5 carrying the fimB and fimE genes, pLP4 containing the fimB gene only, and pLP6 containing the fimE gene only.

Plasmid pLP4 was constructed by inserting a 2300 bp BglII-StuI fragment from pPKL10 (Klemm, 1986, op.cit.) into BamHI and EcoRV digested plasmid pACYC184 (see FIG. 26). Plasmid pLP5 was constructed by inserting a 2650 bp BglII-SnabI fragment into BamHI and EcoRV digested plasmid pACYC184. Plasmid pLP6 was a HincII deletion derivative of pLP5 (see FIG. 26).

Plasmids pLP4, pLP5 and pLP6 were transformed into E. coli MC1000 host cells already containing pPKL100, which were grown on 0.2% glycerol A+B medium supplemented with 10 µg/ml proline, threonine, isoleucine and leucine, 20 µg/ml chloramphenicol and 100 µg/ml ampicillin. The growth rates, as measured by the increase in the optical density of the three combinations, were as shown in Table 3. The copy number ratio of pBR322 to pACYC184 is roughly 4:1, and consequently hosts harbouring the plasmid combination pLP4+pPKL100 have a corresponding 25% increase in the gene dosage of fimb (which mediates an "off" to "on" configuration of the invertible DNA fragment containing the fimA promoter in pPKL100), as compared to cells harbouring pPKL100 only. On the other hand, cells containing the plasmid combination pLP6+pPKL100 have a roughly 25% increase in the amount of the fimE gene (which mediates an "on" to "off" configuration of the invertible DNA fragment).

A clear indication of a more frequent activation of the fimA promoter and ensuing killing of the host in the case of the pLP4+pPKL100 combination appeared from a generation time of 140 minutes for the corresponding host as compared to 110 minutes for hosts containing the pLP6+pPKL100 combination (Table 3). Furthermore, the former showed the presence of approximately 12% of ghost cells and the latter to have virtually none, when the cells were inspected microscopically.

TABLE 3

| Plasmids | Generation time (population doubling time) |
|---|---|
| pPKL100 + pLP4 | 140 min. |
| pPKL100 + pLP5 | 120 min. |
| pPKL100 + pLP6 | 110 min. |

Deposit of Microorganisms

Pursuant to the provisions of the Budapest Treaty on the International Recognition of Microorganisms for the Purposes of Patent Procedures, samples of the following microorganisms were deposited on Mar. 25, 1987, in Deutsche Sammlung von Mikroorganismen, Grisebachstrasse 8, 3400 Göttingen, Federal Republic of Germany:

| Strain | Accession No. |
|---|---|
| B. subtilis BD170 (pLK26) | DSM 4037 |
| E. coli HB101 (pNL7) | DSM 4034 |
| E. coli K-12 MC1000 (pKG345) | DSM 4036 |
| E. coli K-12 MC1000 (pPKL100) | DSM 4035 |
| E. coli K-12 MC1000 (pPKL100 + pLP4) | DSM 4031 |
| E. coli K-12 MC1000 (pPKL100 + pLP5) | DSM 4032 |
| E. coli K-12 MC1000 (pPKL100 + pLP6) | DSM 4033 |

We claim:

1. A recombinant replicon which comprises a first gene, whose expression results in the formation of a toxic product which has a toxic effect on Enterobacteriaceae cells in which said replicon can replicate, and an invertible promoter which regulates the expression of said first gene, whereby, when said replicon is introduced into host Enterobacteriaceae cells in which said promoter is functional, under suitable conditions of expression said invertible promoter is repeatedly inverted, leading to stochastic expression of the first gene and to formation of said toxic product, thereby stochastically limiting the life of said replicon-bearing host cell, where said first gene comprises a coding sequence which encodes a polypeptide having an amino acid sequence wherein at least about 60% of the residues are identical to or conservative modifications of the corresponding residues of the amino acid sequence of the R1 Hok and/or F Hok polypeptides and/or the polypeptide encoded by relB-orf3.

2. The replicon of claim 1 wherein the invertible promoter is the promoter of the fimA gene or a functional homologue thereof.

3. The replicon of claim 1, wherein the invertible promoter is operably linked to said first gene but not natively associated therewith.

4. The replicon of claim 1, said promoter having a phase switch responsive to "on" and "off" gene products, being caused to transcribe said first gene by an "on" gene product and caused not to transcribe said first gene by an "off" gene product, whereby the frequency of expression of said first gene may be controlled by modulating the relative levels of expression of said "on" and "off" gene products.

5. The replicon of claim 4, further comprising a gene encoding an "on" gene product which directs the phase switch of said invertible promoter into the "on" position.

6. The replicon of claim 4, further comprising a gene encoding an "off" gene product which directs the phase switch of said invertible promoter into the "off" position.

7. The replicon of claim 5 wherein the "on" product encoding gene is the fimB gene or a functional homologue thereof.

47

8. The replicon of claim 5 wherein the "off" product encoding gene is the fimE gene or a functional homologue thereof.

9. The replicon of claim 1 wherein said coding sequence encodes a polypeptide in which the Cys residues at amino acid positions 16 and 31 of the R1 Hok or F Hok sequence are conserved.

10. The replicon of claim 1 in which said coding sequence encodes a polypeptide in which at least about 60% of the charged amino acid residues of R1 Hok are conserved.

11. The replicon of claim 1 wherein said coding sequence encodes a polypeptide selected from the group consisting of the gene products of R1 hok, F hok, and relB-orf3.

12. A transformed bacterial cell population comprising Enterobacteriaceae cells harboring the replicon of claim 1, said replicon being capable of replicating in said cells, said invertible promoter being functional in said cells, the expression of said first gene having a toxic effect on said cells.

13. The cell population of claim 12 where the first gene is the R1 hok or F hok gene.

14. The cell population of claim 12 where the cells are *E. coli* cells.

15. The cell population of claim 12 wherein the invertible transcriptional promoter is the promoter of the fimA gene.

16. The transformed cell population of claim 12 wherein said replicon further comprises a gene expressing a fusion protein, said fusion protein comprising an outer surface protein of said cell and an epitope of interest not native to said cell, whereby said fusion protein serves as a means for transporting the epitope, when expressed, to the outer surface of the cell.

17. A method of stochastically limiting an Enterobacteriaceae cell population which comprises transforming the cells of said cell population with a replicon according to claim 1, said replicon being capable of replicating in said cells, the expression of said first gene having a toxic effect on said cells, the frequency of the inversion of said invertible promoter in said cells being such as to stochastically limit the survival of said cell population.

18. The method of claim 17 wherein the invertible promoter is a fimA promoter.

19. The method of claim 17, wherein said toxic effect is such that if said promoter remained "on", at least about 99.9% of the cells would be killed.

20. The method of claim 17 wherein said toxic effect is such that at least 99.9% of the cells are killed in one hour if said promoter remains "on".

21. The method of claim 17 wherein the invertible promoter has substantially the same inversion frequency as the fimA promoter.

22. The method of claim 17 wherein one of the manifestations of said toxic effect is the transformation of at least some of the bacterial cells into ghost cells.

23. The method of claim 17 wherein the first gene encodes a polypeptide which is expressed in nature in Enterobacteriaceae, Pseudomonadaceae, or Bacillaceae cells.

24. A transformed bacterial cell of a first kind of cell, said transformed cell comprising:

(a) a recombinant extrachromosomal replicon comprising a first gene, expressed under the control of a regulatable promoter, whose expression results in formation of a toxic product which has a lethal effect on both cells of said first kind and on bacterial cells of a second kind with which said first kind of cells is capable of naturally exchanging genetic information; and

48

(b) a second replicon comprising a second gene which encodes a gene product which inhibits expression of such first gene, said second gene being lacking in cells of said second kind, said first and second kinds of cells both being selected from the group consisting of Enterobacteriaceae, Pseudomonadaceae, and Bacillaceae cells, where said first gene comprises a coding sequence which encodes a polypeptide having an amino acid sequence wherein at least about 60% of the residues are identical to or conservative modifications of the corresponding residues of the amino acid sequence of the R1 Hok and/or F Hok polypeptides and/or the polypeptide encoded by relB-orf3.

25. The transformed cell of claim 24, wherein the second gene encodes a repressor polypeptide which inhibits transcription of said first gene.

26. The transformed cell of claim 25 wherein the second gene encodes trp repressor and the first gene is operably linked to a trp promoter including the operator site for trp repressor.

27. The transformed cell of claim 24 in which the second replicon is a recombinant chromosomal replicon.

28. A method of containing an extrachromosomal recombinant replicon to a first kind of bacterial cells, where said replicon could be naturally transferred to a second kind of bacterial cells, which comprises providing on the recombinant extrachromosomal replicon a first gene, expressed under the control of a regulatable promoter which is functional in both kinds of cells, whose expression results in formation of a toxic product which has a lethal effect on the first and second kind of cells, said first kind of cells having or being modified to have a second replicon comprising a second gene which encodes a gene product which inhibits the expression of said first gene and thereby protects said first kind of cells, said second gene being lacking in said second kind of cells, whereby if a cell of the second kind receives said extrachromosomal recombinant replicon said first gene is expressed and said toxic product is formed, which has a toxic effect thereon said first and second kinds of cells both being selected from the group consisting of Enterobacteriaceae, Pseudomonadaceae, and Bacillaceae cells, where said first gene comprises a coding sequence which encodes a polypeptide having an amino acid sequence wherein at least about 60% of the residues are identical to or conservative modifications of the corresponding residues of the amino acid sequence of the R1 Hok and/or F Hok polypeptides and/or the polypeptide encoded by relB-orf3.

29. The method of claim 28 in which said second replicon is a chromosomal replicon.

30. The method of claim 28, wherein said second gene encodes a repressor polypeptide which inhibits transcription of said first gene.

31. The method of claim 30, wherein said repressor polypeptide is the trp repressor and said first gene is operably linked to a trp promoter including the operator site for said trp repressor.

32. The method of claim 29 wherein the chromosomal replicon is recombinant and the second gene is not natively associated with said chromosomal replicon.

33. The method of claim 28 wherein said lethal effect is such that at least 99.9% of the cells are killed in one hour if not protected by said inhibitory gene product.

34. The method of claim 28 wherein the cells are gram-negative bacterial cells.

35. The method of claim 28 wherein one of the manifestations of said toxic effect is the transformation of at least some of the bacterial cells into ghost cells.

36. The method of claim 28 wherein the cells are Enterobacteriaceae cells.

37. The method of claim 28 wherein the first gene encodes a polypeptide which is expressed in nature in Enterobacteriaceae, Pseudomonadaceae, or Bacillaceae cells.

38. The method of claim 28, wherein the first gene is the R1 hok or F hok gene.

39. The method of claim 28 wherein said coding sequence encodes a polypeptide in which the Cys residues at amino acid positions 16 and 31 of the R1 Hok or F Hok sequence are conserved.

40. The method of claim 28 in which said coding sequence encodes a polypeptide in which at least about 60% of the charged amino acid residues of R1 Hok are conserved.

41. The method of claim 28 wherein said coding sequence encodes a polypeptide selected from the group consisting of the gene products of R1 hok, F hok, and relB-orf3.

42. The transformed bacterial cell of claim 24 wherein said coding sequence encodes a polypeptide in which the Cys residues at amino acid positions 16 and 31 of the R1 Hok or F Hok sequence are conserved.

43. The transformed bacterial cell of claim 24 in which said coding sequences encodes a polypeptide in which at least about 60% of the charged amino acid residues of R1 Hok are conserved.

44. The transferred bacterial cell of claim 24 wherein said coding sequence encodes a polypeptide selected from the group consisting of the gene products of R1 hok, F hok, and relB-orf3.

45. A method of biologically containing bacterial cells growing in a first, controllable environment, which cells could escape to a second and physically distinct environment, which comprises:
   a) providing in said cell a recombinant replicon, said replicon comprising a first gene, expressed under the control of a regulatable promoter which is functional in said cells, whose expression results in formation of a toxic product which has a toxic effect on said cells, said cells natively containing or being modified to contain a second gene whose product inhibits expression of said first gene, said inhibition being regulatable by an environmental factor, the level of said environmental factor in the second environment being such that said first gene is expressed and said toxic product is formed, whereby cells in the second environment which harbor said replicon are killed, and
   b) manipulating the first environment such that the level of the environmental factor therein is such that expression of said first gene is inhibited, whereby cells bearing said replicon are able to grow in said first environment but not in said second environment, the toxic effect being such that at least 99.9% of the cells are killed in said second environment, which but for said effect is an environment in which said cells can grow where said bacterial cells are selected from the group consisting of Enterobacteriaceae, Pseudomonadaceae, and Bacillaceae cells, where said first gene comprises a coding sequence which encodes a polypeptide having an amino acid sequence wherein at least about 60% of the residues are identical to or conservative modifications of the corresponding residues of the amino acid sequence of the R1 Hok and/or F Hok polypeptides and/or the polypeptide encoded by relB-orf3.

46. The method of claim 45, wherein the environmental factor is temperature.

47. The method of claim 45, wherein the environmental factor is the concentration of a regulator chemical.

48. The method of claim 45, wherein said second gene expresses a repressor polypeptide which inhibits transcription of said first gene.

49. The method of claim 47, wherein the environmental factor is the concentration of tryptophan, the promoter is the trp promoter, the second gene is the trp repressor gene, and sufficient tryptophan is added to said first environment to provide an inhibitory concentration thereof.

50. The method of claim 45, wherein the second gene is located on the same replicon as said first gene.

51. The method of claim 45, wherein the second gene is located on a chromosomal replicon and the first gene on an extrachromosomal replicon.

52. The method of claim 45, wherein the toxic effect is such that at least 99.9% of the cells are killed within one hour of excape into the second environment.

53. The method of claim 45 wherein the cells are gram-negative bacterial cells.

54. The method of claim 45 wherein one of the manifestations of said toxic effect is the transformation of at least some of the bacterial cells into ghost cells.

55. The method of claim 45 wherein the cells are Enterobacteriaceae cells.

56. The method of claim 45 wherein the first gene encodes a polypeptide which is expressed in nature in Enterobacteriaceae, Pseudomonadaceae, or Bacillaceae cells.

57. The method of claim 45 wherein said coding sequence encodes a polypeptide in which the Cys residues at amino acid positions 16 and 31 of the R1 Hok or F Hok sequence are conserved.

58. The method of claim 45 in which said coding sequences encodes a polypeptide in which at least about 60% of the charged amino acid residues of R1 Hok are conserved.

59. The method of claim 45 wherein said coding sequence encodes a polypeptide selected from the group consisting of the gene products of R1 hok, F hok, and relB-orf3.

60. A method of biologically containing bacterial cells growing in an initial environment subject to physical or chemical change resulting in a changed environment, so that said cells are able to grow in the initial environment but not in the changed environment, which comprises providing in said cells a recombinant replicon, said replicon comprising a first gene, expressed under the control of a regulatable promoter which is functional in said cells, whose expression results in formation of a toxic product which has a toxic effect on said cells, said cells natively containing or being modified to contain an inhibitory gene whose product inhibits expression of said first gene, said inhibition being regulatable by an environmental factor, the level of said environmental factor in said changed environment being such that said first gene is expressed and said toxic product is formed, whereby said cells in said changed environment which harbor said replicon are killed, the level of environmental factor in said initial environment being such that expression of said first gene is inhibited, whereby cells bearing said replicon are able to grow in the initial environment but not in the changed environment, the toxic effect being such that at least 99.9% of the cells are killed in said changed environment, which but for said effect is an environment in which said cells can grow, said cells being selected from the group consisting of Entero-bacteriaceae, Pseudomonadaceae, and Bacillaceae cells, where said first gene comprises a coding sequence which encodes a polypeptide having an amino acid sequence wherein at least about 60% of the residues are identical to or conservative modifications of the corresponding residues of the amino acid sequence of the R1 Hok and/or F Hok polypeptides and/or the polypeptide encoded by relB-orf3.

61. The method of claim 60 wherein the environmental factor is the concentration of a chemical in the environment.

62. The method of claim 60, wherein the toxic effect is such that at least 99.9% of the cells are killed within one hour of said physical or chemical change in the environment.

63. The method of claim 60 wherein the cells are gram-negative bacterial cells.

64. The method of claim 60 wherein one of the manifestations of said toxic effect is the transformation of at least some of the bacterial cells into ghost cells.

65. The method of claim 60 wherein the cells are Enterobacteriaceae cells.

66. The method of claim 60 wherein the first gene encodes a polypeptide which is expressed in nature in Enterobacteriaceae, Pseudomonadaceae, or Bacillaceae cells.

67. The method of claim 60 wherein said coding sequence encodes a polypeptide in which the Cys residues at amino acid positions 16 and 31 of the R1 Hok or F Hok sequence are conserved.

68. The method of claim 60 in which said coding sequences encodes a polypeptide in which at least about 60% of the charged amino acid residues of R1 Hok are conserved.

69. The method of claim 60 wherein said coding sequence encodes a polypeptide selected from the group consisting of the gene products of R1 hok, F hok, and relB-orf3.

* * * * *